(12) United States Patent
Dikovsky et al.

(10) Patent No.: US 12,303,392 B2
(45) Date of Patent: *May 20, 2025

(54) METHOD AND SYSTEM FOR FABRICATING OBJECT FEATURING PROPERTIES OF A HARD TISSUE

(71) Applicant: Stratasys Ltd., Rehovot (IL)

(72) Inventors: Daniel Dikovsky, Ariel (IL); Blake Zachary Courter, Reading, MA (US); Ben Klein, Tel-Aviv (IL)

(73) Assignee: Stratasys Ltd., Rehovot (IL)

( * ) Notice: Subject to any disclaimer, the term of this patent is extended or adjusted under 35 U.S.C. 154(b) by 13 days.

This patent is subject to a terminal disclaimer.

(21) Appl. No.: 18/195,441

(22) Filed: May 10, 2023

(65) Prior Publication Data

US 2023/0277322 A1     Sep. 7, 2023

Related U.S. Application Data

(63) Continuation of application No. 16/632,548, filed as application No. PCT/IL2018/050843 on Jul. 27, 2018, now Pat. No. 11,696,832.

(Continued)

(51) Int. Cl.
*B29C 64/393* (2017.01)
*A61F 2/30* (2006.01)
(Continued)

(52) U.S. Cl.
CPC .......... *A61F 2/3094* (2013.01); *B29C 64/112* (2017.08); *B29C 64/336* (2017.08);
(Continued)

(58) Field of Classification Search
CPC .......... A61F 2/3094; A61F 2002/30985; A61F 2/30942; A61F 2002/30014;
(Continued)

(56) References Cited

U.S. PATENT DOCUMENTS 3,425,418 A    2/1969   Chvapil et al.
5,110,834 A    5/1992   Horn et al.
(Continued)

FOREIGN PATENT DOCUMENTS

CH     641541      2/1984
CN     1654028     8/2005
(Continued)

OTHER PUBLICATIONS

Morrow et al. "Transversely isotropic tensile material properties of skeletal muscle tissue" from "Journal of the Mechanical Biomedical Materials 3 (2010) 124-129" (Year: 2010).*

(Continued)

*Primary Examiner* — Yuhui R Pan

(57) ABSTRACT

A method of additive manufacturing an object featuring properties of a hard bodily tissue, comprises: dispensing and solidifying a plurality of non-biological material formulations to sequentially form a plurality of hardened layers in a configured pattern corresponding to a shape of the object. The method forms voxel elements containing different material formulations at interlaced locations to provide a three-dimensional textured region spanning over the portion. The material formulations and the interlaced locations are selected such that the textured region exhibits, once hardened, a stress variation of at most ±20% over a strain range of from about 0.1% to about 0.3%.

18 Claims, 31 Drawing Sheets

Related U.S. Application Data

(60) Provisional application No. 62/538,026, filed on Jul. 28, 2017.

(51) Int. Cl.
  B29C 64/112 (2017.01)
  B29C 64/336 (2017.01)
  B33Y 50/02 (2015.01)
  B33Y 10/00 (2015.01)
  B33Y 30/00 (2015.01)
  B33Y 70/00 (2020.01)
  B33Y 80/00 (2015.01)

(52) U.S. Cl.
  CPC .. B29C 64/393 (2017.08); A61F 2002/30985 (2013.01); B33Y 10/00 (2014.12); B33Y 30/00 (2014.12); B33Y 50/02 (2014.12); B33Y 70/00 (2014.12); B33Y 80/00 (2014.12)

(58) Field of Classification Search
  CPC ......... A61F 2002/30016; B29C 64/112; B29C 64/336; B29C 64/393; B29C 70/24; B33Y 10/00; B33Y 30/00; B33Y 50/02; B33Y 70/00; B33Y 80/00; B33Y 40/00
  See application file for complete search history.

(56) References Cited

U.S. PATENT DOCUMENTS

| | | | |
|---|---|---|---|
| 6,228,923 B1 | 5/2001 | Lombardi et al. | |
| 6,259,962 B1 | 7/2001 | Gothait | |
| 6,569,373 B2 | 5/2003 | Napadensky | |
| 6,658,314 B1 | 12/2003 | Gothait | |
| 6,850,334 B1 | 2/2005 | Gothait | |
| 7,183,335 B2 | 2/2007 | Napadensky | |
| 7,209,797 B2 | 4/2007 | Kritchman et al. | |
| 7,225,045 B2 | 5/2007 | Gothait et al. | |
| 7,255,825 B2 | 8/2007 | Nielsen et al. | |
| 7,285,237 B2 | 10/2007 | Newell et al. | |
| 7,300,619 B2 | 11/2007 | Napadensky et al. | |
| 7,479,510 B2 | 1/2009 | Napadensky et al. | |
| 7,500,846 B2 | 3/2009 | Eshed et al. | |
| 7,962,237 B2 | 6/2011 | Kritchman | |
| 9,031,680 B2 | 5/2015 | Napadensky | |
| 9,156,999 B2 | 10/2015 | Ng et al. | |
| 9,227,365 B2 | 1/2016 | Dikovsky et al. | |
| 9,805,624 B2 | 10/2017 | Reihsen et al. | |
| 2004/0000046 A1 | 1/2004 | Stinson | |
| 2004/0175686 A1* | 9/2004 | Ono | B33Y 80/00 434/274 |
| 2004/0183226 A1 | 9/2004 | Newell et al. | |
| 2005/0069784 A1* | 3/2005 | Gothait | B33Y 10/00 700/98 |
| 2005/0131662 A1 | 6/2005 | Ascenzi | |
| 2005/0249400 A1 | 11/2005 | Fukumoto | |
| 2007/0168815 A1 | 7/2007 | Napadensky et al. | |
| 2009/0024152 A1 | 1/2009 | Boyden et al. | |
| 2010/0191360 A1 | 7/2010 | Napadensky et al. | |
| 2013/0040091 A1* | 2/2013 | Dikovsky | B29C 64/112 428/68 |
| 2014/0052285 A1 | 2/2014 | Butcher et al. | |
| 2014/0163445 A1 | 6/2014 | Pallari et al. | |
| 2014/0180397 A1 | 6/2014 | Gerberding et al. | |
| 2014/0312535 A1* | 10/2014 | Dikovsky | B33Y 50/00 264/401 |
| 2015/0210010 A1 | 7/2015 | Napadensky | |
| 2015/0282963 A1 | 10/2015 | Gounis et al. | |
| 2015/0353750 A1 | 12/2015 | Titterington et al. | |
| 2016/0009029 A1 | 1/2016 | Cohen et al. | |
| 2016/0145452 A1 | 5/2016 | Fong et al. | |
| 2016/0167306 A1* | 6/2016 | Vidimce | G06F 30/00 425/166 |
| 2016/0302911 A1 | 10/2016 | Soletti | |
| 2016/0332382 A1 | 11/2016 | Coward et al. | |
| 2017/0015850 A1 | 1/2017 | Yoshino et al. | |
| 2017/0121542 A1 | 5/2017 | Xu et al. | |
| 2017/0169733 A1 | 6/2017 | Peterson et al. | |
| 2017/0190859 A1 | 7/2017 | Liu et al. | |
| 2018/0036953 A1 | 2/2018 | Gottschalk-Gaudig | |
| 2018/0193152 A1* | 7/2018 | Bauer | A61F 2/34 |
| 2018/0207863 A1 | 7/2018 | Porter et al. | |
| 2018/0244831 A1 | 8/2018 | Hirata et al. | |
| 2018/0281295 A1 | 10/2018 | Tibbits et al. | |
| 2018/0296343 A1 | 10/2018 | Wei | |
| 2019/0136079 A1 | 5/2019 | Moussa | |
| 2020/0155321 A1 | 5/2020 | Dikovsky et al. | |
| 2020/0164109 A1 | 5/2020 | Kroll et al. | |
| 2020/0171739 A1 | 6/2020 | Dikovsky et al. | |
| 2020/0172748 A1 | 6/2020 | Moussa | |
| 2020/0231803 A1 | 7/2020 | Amiel-Levy et al. | |
| 2020/0368009 A1 | 11/2020 | Dikovsky et al. | |
| 2020/0384680 A1 | 12/2020 | Dikovsky et al. | |
| 2021/0155722 A1 | 5/2021 | Vaughn et al. | |
| 2023/0103463 A1 | 4/2023 | Amiel-Levy et al. | |
| 2023/0126854 A1 | 4/2023 | Dikovsky | |
| 2024/0263006 A1 | 8/2024 | Amicl-Levy et al. | |

FOREIGN PATENT DOCUMENTS

| | | |
|---|---|---|
| CN | 1759139 | 4/2006 |
| CN | 101219461 | 7/2008 |
| CN | 102626347 | 8/2012 |
| CN | 103025506 | 4/2013 |
| CN | 103189187 | 7/2013 |
| CN | 104136199 | 11/2014 |
| CN | 104490489 | 4/2015 |
| CN | 105479751 | 4/2016 |
| CN | 105873954 | 8/2016 |
| CN | 106214296 | 12/2016 |
| CN | 106414039 | 2/2017 |
| CN | 106491241 | 3/2017 |
| CN | 106626423 | 5/2017 |
| DE | 102015214883 | 2/2017 |
| EP | 0442256 | 8/1991 |
| EP | 2466380 | 6/2012 |
| EP | 2636511 | 9/2013 |
| EP | 2780154 | 9/2014 |
| EP | 3015251 | 5/2016 |
| EP | 2780154 B1 | 3/2018 |
| GB | 1044680 | 10/1966 |
| GB | 2515348 | 12/2014 |
| JP | 07-313382 | 12/1995 |
| JP | 2003-011237 | 1/2003 |
| JP | 2004-202126 | 7/2004 |
| JP | 2004-255839 | 9/2004 |
| JP | 2012-111226 | 6/2012 |
| JP | 2013-522453 | 6/2013 |
| JP | 2014-148174 | 8/2014 |
| JP | 2014-533613 | 12/2014 |
| JP | 2015-009495 | 1/2015 |
| JP | 2015-136915 | 7/2015 |
| JP | 2015-219371 | 12/2015 |
| JP | 2016-088944 | 5/2016 |
| JP | 2016-113518 | 6/2016 |
| JP | 2016-198897 | 12/2016 |
| JP | 2016-540502 | 12/2016 |
| JP | 2017-048288 | 3/2017 |
| JP | 2018-521710 | 8/2018 |
| WO | WO 03/030964 | 4/2003 |
| WO | WO 2004/081311 | 9/2004 |
| WO | WO 2005/037529 | 4/2005 |
| WO | WO 2005/038751 | 4/2005 |
| WO | WO 2010/030013 | 3/2010 |
| WO | WO 2011/119828 | 9/2011 |
| WO | WO 2013/072644 | 5/2013 |
| WO | WO 2013/072874 | 5/2013 |
| WO | WO 2015/069619 | 5/2015 |
| WO | WO 2015/107333 | 7/2015 |
| WO | WO 2016/142947 | 9/2016 |
| WO | WO 2016/153711 | 9/2016 |
| WO | WO 2016/161944 | 10/2016 |
| WO | WO 2016/179242 | 11/2016 |
| WO | WO 2016/199131 | 12/2016 |

(56) References Cited

FOREIGN PATENT DOCUMENTS

| WO | WO 2017/020971 | 2/2017 |
|---|---|---|
| WO | WO 2017/029657 | 2/2017 |
| WO | WO 2017/208238 | 12/2017 |
| WO | WO 2017/222602 | 12/2017 |
| WO | WO 2018/007579 | 1/2018 |
| WO | WO 2019/021291 | 1/2019 |
| WO | WO 2019/021292 | 1/2019 |
| WO | WO 2019/021292 A9 | 1/2019 |
| WO | WO 2019/021293 | 1/2019 |
| WO | WO 2019/021294 | 1/2019 |
| WO | WO 2019/021295 | 1/2019 |

OTHER PUBLICATIONS

Raviv et al. "Active Printed Materials for Complex Self-Evolving Deformations" from Scientific Reports | (2014) (Year: 2014).*
Office Action Dated Nov. 28, 2023 From the Israel Patent Office Re. Application No. 272315. (5 Pages).
Interview Summary Dated Aug. 28, 2023 From the US Patent and Trademark Office Re. U.S. Appl. No. 16/634,171. (2 Pages).
Notice of Reason(s) for Rejection Dated Mar. 8, 2024 From the Japan Patent Office Re. Application No. 2023-96676 and Its Translation Into English. (5 Pages).
Notification of Office Action and Search Report Dated Apr. 30, 2023 From the State Intellectual Property Office of the People's Republic of China Re. Application No. 201880056260.7 and Its Summary Into English. (8 Pages).
Notice of Allowance Dated Jun. 14, 2023 from the US Patent and Trademark Office Re. U.S. Appl. No. 16/634,582. (24 pages).
Invitation Pursuant to Rule 137(4) EPC and Article 94(3) EPC Dated Jan. 23, 2024 From the European Patent Office Re. Application No. 18759758.8 (2 Pages).
Notice of Reasons for Rejection Dated Apr. 23, 2024 From the Japan Patent Office Re. Application No. 2023-88306 and its Translation Into English.(8 Pages).
Communication Pursuant to Article 94(3) EPC Dated Feb. 2, 2022 From the European Patent Office Re. Application No. 18762158.6. (8 Pages).
Communication Pursuant to Article 94(3) EPC Dated Mar. 2, 2023 From the European Patent Office Re. Application No. 18759758.8. (6 Pages).
Communication Pursuant to Article 94(3) EPC Dated Feb. 3, 2022 From the European Patent Office Re. Application No. 18758746.4. (7 Pages).
Communication Pursuant to Article 94(3) EPC Dated Nov. 4, 2021 From the European Patent Office Re. Application No. 18759760.4. (8 Pages).
Communication Pursuant to Article 94(3) EPC Dated Feb. 14, 2023 From the European Patent Office Re. Application No. 18762158.6. (4 Pages).
Communication Pursuant to Article 94(3) EPC Dated Feb. 19, 2021 From the European Patent Office Re. Application No. 18759759.6. (4 Pages).
English Summary Dated Feb. 13, 2023 of Decision on Rejection Dated Jan. 20, 2023 From the State Intellectual Property Office of the People's Republic of China Re. Application No. 201880063362.1. (8 pages).
English Translation Dated Apr. 13, 2022 of Notification of Office Action and Search Report Dated Feb. 28, 2022 From the State Intellectual Property Office of the People's Republic of China Re. Application No. 201880063362.1. (15 Pages).
International Preliminary Report on Patentability Dated Feb. 6, 2020 From the International Bureau of WIPO Re. Application No. PCT/IL2018/050839. (8 Pages).
International Preliminary Report on Patentability Dated Feb. 6, 2020 From the International Bureau of WIPO Re. Application No. PCT/IL2018/050840. (8 Pages).
International Preliminary Report on Patentability Dated Feb. 6, 2020 From the International Bureau of WIPO Re. Application No. PCT/IL2018/050841. (8 Pages).
International Preliminary Report on Patentability Dated Feb. 6, 2020 From the International Bureau of WIPO Re. Application No. PCT/IL2018/050842. (8 Pages).
International Preliminary Report on Patentability Dated Feb. 6, 2020 From the International Bureau of WIPO Re. Application No. PCT/IL2018/050843. (9 Pages).
International Search Report and the Written Opinion Dated Dec. 3, 2018 From the International Searching Authority Re. Application No. PCT/IL2018/050841. (14 Pages).
International Search Report and the Written Opinion Dated Dec. 10, 2018 From the International Searching Authority Re. Application No. PCT/IL2018/050839. (14 Pages).
International Search Report and the Written Opinion Dated Dec. 10, 2018 From the International Searching Authority Re. Application No. PCT/IL2018/050842. (14 Pages).
International Search Report and the Written Opinion Dated Nov. 16, 2018 From the International Searching Authority Re. Application No. PCT/IL2018/050843. (16 Pages).
International Search Report and the Written Opinion Dated Nov. 19, 2018 From the International Searching Authority Re. Application No. PCT/IL2018/050840. (13 Pages).
Notice of Allowance Dated Sep. 14, 2022 From the US Patent and Trademark Office Re. U.S. Appl. No. 16/634,185. (39 Pages).
Notice of Allowance Dated Feb. 15, 2023 From the US Patent and Trademark Office Re. U.S. Appl. No. 16/632,548. (6 Pages).
Notice of Allowance Dated Aug. 25, 2022 From the US Patent and Trademark Office Re. U.S. Appl. No. 16/634,173. (76 Pages).
Notice of Reason for Rejection Dated Mar. 10, 2023 From the Japan Patent Offic Re. Application No. 2020-504382 and Its Translation Into English. (7 Pages).
Notice of Reason for Rejection Dated Jun. 21, 2022 From the Japan Patent Office Re. Application No. 2020-504351 and Its Translation Into English. (9 Pages).
Notice of Reason for Rejection Dated Aug. 26, 2022 From the Japan Patent Offic Re. Application No. 2020-504382 and Its Translation Into English. (20 Pages).
Notice of Reason(s) for Rejection Dated Aug. 16, 2022 From the Japan Patent Office Re. Application No. 2020-504356 and Its Translation Into English. (14 Pages).
Notice of Reason(s) for Rejection Dated Jan. 20, 2023 From the Japan Patent Office Re. Application No. 2020-504391 and Its Translation Into English. (11 Pages).
Notice of Reasons for Rejection Dated Jul. 12, 2022 From the Japan Patent Office Re. Application No. 2020-504391 and Its Translation Into English. (8 Pages).
Notice of Reasons for Rejection Dated Feb. 17, 2023 From the Japan Patent Office Re. Application No. 2020-504413 and Its Translation Into English. (4 Pages).
Notice of Reasons for Rejection Dated Apr. 26, 2022 From the Japan Patent Office Re. Application No. 2020-504413 and Its Translation Into English. (6 Pages).
Notice of Rejection Dated Apr. 6, 2022 From the State Intellectual Property Office of the People's Republic of China Re. Application No. 201880063414.5. (5 Pages).
Notification of Office Action Dated Aug. 8, 2022 From the State Intellectual Property Office of the People's Republic of China Re. Application No. 201880063362.1. (14 Pages).
Notification of Office Action and Search Report Dated Jun. 1, 2021 From the State Intellectual Property Office of the People's Republic of China Re. Application No. 201880063414.5 with an English Translation. (8 Pages).
Notification of Office Action and Search Report Dated Jun. 2, 2021 From the State Intellectual Property Office of the People's Republic of China Re. Application No. 201880063362.1 and Its Translation of Office Action Into English. (8 Pages).
Notification of Office Action and Search Report Dated May 8, 2021 From the State Intellectual Property Office of the People's Republic of China Re. Application No. 201880056051.2. (9 Pages).

(56) References Cited

OTHER PUBLICATIONS

Notification of Office Action and Search Report Dated Nov. 11, 2021 From the State Intellectual Property Office of the People's Republic of China Re. Application No. 201880056051.2. (8 Pages).
Notification of Office Action and Search Report Dated Mar. 17, 2022 From the State Intellectual Property Office of the People's Republic of China Re. Application No. 201880063361.7. (5 Pages).
Notification of Office Action and Search Report Dated Feb. 28, 2022 From the State Intellectual Property Office of the People's Republic of China Re. Application No. 201880063362.1. (10 Pages).
Notification of Office Action Dated Jun. 11, 2021 From the State Intellectual Property Office of the People's Republic of China Re. Application No. 201880063361.7. (10 Pages).
Notification of Office Action Dated May 12, 2022 From the State Intellectual Property Office of the People's Republic of China Re. Application No. 201880056051.2 and Its Translation Into English. (9 Pages).
Notification of Office Action Dated Nov. 17, 2021 From the State Intellectual Property Office of the People's Republic of China Re. Application No. 201880063414.5. (7 Pages).
Notification of Office Action Dated Jan. 20, 2023 From the State Intellectual Property Office of the People's Republic of China Re. Application No. 201880063362.1. (8 Pages).
Office Action Dated Mar. 8, 2023 From the Israel Patent Office Re. Application No. 272317. (5 Pages).
Office Action Dated Jul. 10, 2022 From the Israel Patent Office Re. Application No. 272316. (3 Pages).
Office Action Dated Nov. 13, 2022 From the Israel Patent Office Re. Application No. 272315. (3 Pages).
Office Action Dated Mar. 22, 2023 From the Israel Patent Office Re. Application No. 272319. (4 Pages).
Office Action Dated Apr. 23, 2023 From the Israel Patent Office Re. Application No. 272318. (4 Pages).
Official Action Dated Jun. 9, 2022 from US Patent and Trademark Office Re. U.S. Appl. No. 16/632,548. (76 pages).
Official Action Dated Apr. 11, 2022 from US Patent and Trademark Office Re. U.S. Appl. No. 16/634,185. (53 pages).
Official Action Dated Sep. 21, 2022 from US Patent and Trademark Office Re. U.S. Appl. No. 16/632,548. (22 pages).
Official Action Dated Feb. 22, 2023 From the US Patent and Trademark Office Re. U.S. Appl. No. 16/634,582. (96 Pages).
Official Action Dated Nov. 8, 2022 from the US Patent and Trademark Office Re. U.S. Appl. No. 16/634,171. (85 pages).
Restriction Official Action Dated Jun. 2, 2022 from US Patent and Trademark Office Re. U.S. Appl. No. 16/634,173. (11 pages).
Restriction Official Action Dated Jun. 14, 2022 From the US Patent and Trademark Office Re. U.S. Appl. No. 16/634,582. (7 Pages).
Restriction Official Action Dated Jun. 24, 2022 from US Patent and Trademark Office Re. U.S. Appl. No. 16/634,171. (6 pages).
Restriction Official Action Dated Jan. 25, 2022 From the US Patent and Trademark Office Re. U.S. Appl. No. 16/634,185. (8 Pages).
Translation Dated Dec. 1, 2021 of Notification of Office Action and Search Report Dated Nov. 11, 2021 From the State Intellectual Property Office of the People's Republic of China Re. Application No. 201880056051.2. (11 Pages).
Translation Dated Jun. 7, 2021 of Notification of Office Action Dated May 8, 2021 From the State Intellectual Property Office of the People's Republic of China Re. Application No. 201880056051.2. (8 Pages).
Translation Dated Apr. 15, 2022 of Notification of Office Action Dated Mar. 17, 2022 From the State Intellectual Property Office of the People's Republic of China Re. Application No. 201880063361.7. (2 Pages).
Translation Dated Dec. 17, 2021 of Notification of Office Action Dated Nov. 2, 17021From the State Intellectual Property Office of the People's Republic of China Re. Application No. 201880063414.5. (7 Pages).
Translation Dated Jun. 18, 2021 of Notification of Office Action Dated Jun. 1, 2021 From the State Intellectual Property Office of the People's Republic of China Re. Application No. 201880063414.5. (5 Pages).
Translation Dated Jul. 2, 2021 of Notification of Office Action Dated Jul. 11, 2021 From the State Intellectual Property Office of the People's Republic of China Re. Application No. 201880063361.7. (31 Pages).
Translation Dated May 20, 2022 of Notice of Rejection Dated Apr. 6, 2022 From the State Intellectual Property Office of the People's Republic of China Re. Application No. 201880063414.5. (14 Pages).
Gustavson "Simplex Noise Demystified", Linköping University, Sweden, XP055522459, Research Report, p. 1-18, Mar. 22, 2005. p. 1.
Turner et al. "Basic Biomechanical Measurements of Bone: A Tutorial", Bone, XP026431978, 14(4): 595-608, Jul. 1, 1993.
Supplementary European Search Report and the European Search Opinion Dated Oct. 24, 2023 From the European Patent Office Re. Application No. 23191995.2. (8 Pages).
Official Action Dated Jun. 8, 2023 from the US Patent and Trademark Office Re. U.S. Appl. No. 16/634,171. (19 pages).
Supplementary European Search Report Dated Feb. 5, 2024 From the European Patent Office Re. Application No. 23205041.9. (5 Pages).
Notice of Allowance Dated Nov. 8, 2023 from the US Patent and Trademark Office Re. U.S. Appl. No. 18/076,478. (54 pages).
Notice of Reasons for Rejection Dated May 17, 2024 From the Japan Patent Office Re. Application No. 2023-128403 and Its Translation Into English. (6 Pages).
Summary Dated Oct. 30, 2024 of Notification of Office Action and Search Report Dated Oct. 9, 2024 From the State Intellectual Property Office of the People's Republic of China Re. Application No. 202210802362.7. ( 7 pages).
Notice of Allowance Dated Oct. 17, 2024 from the US Patent and Trademark Office Re. U.S. Appl. No. 18/592,619. (27 pages).
Notification of Office Action and Search Report Dated Oct. 9, 2024 From the State Intellectual Property Office of the People's Republic of China Re. Application No. 202210802362.7 together with Its Machine Translation. (21 Pages).
Office Action Dated Dec. 3, 2024 From the Israel Patent Office Re. Application No. 312935. (4 Pages).
Official Action Dated Nov. 21, 2024 from the US Patent and Trademark Office Re. U.S. Appl. No. 16/634,171. (56 pages).

* cited by examiner

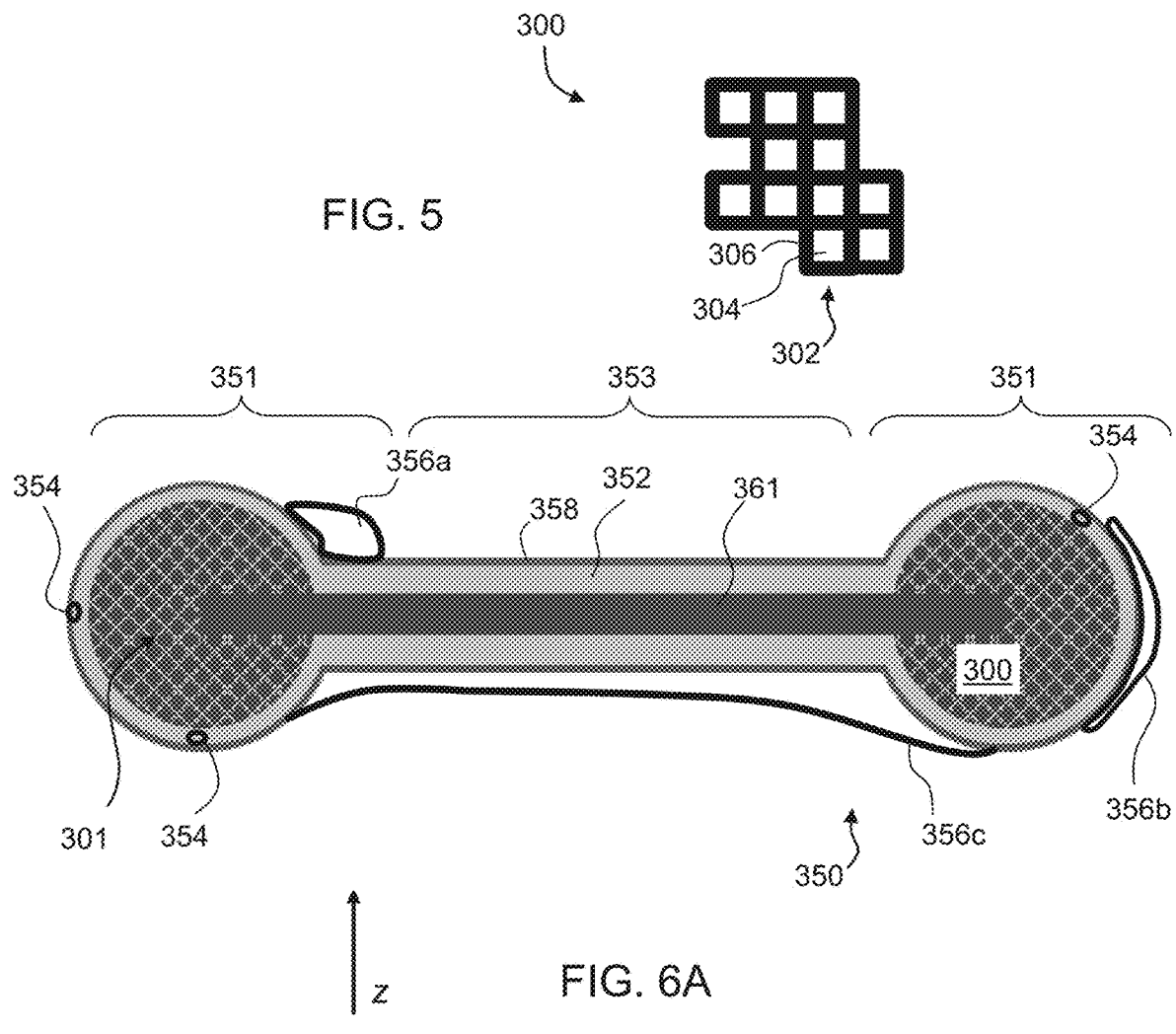
FIG. 5
FIG. 6A
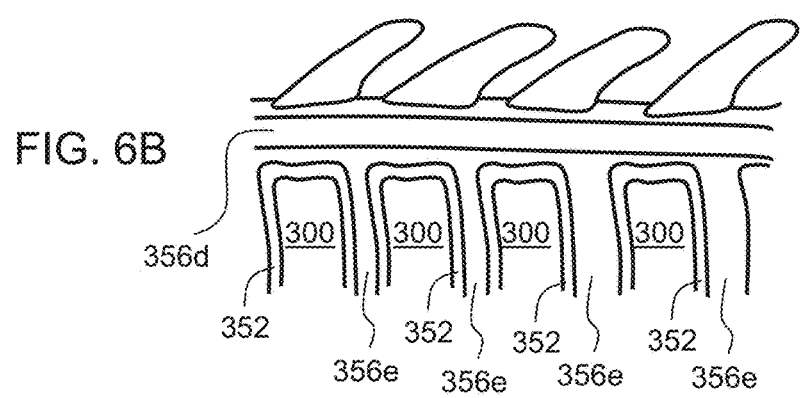
FIG. 6B

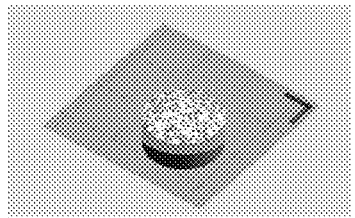
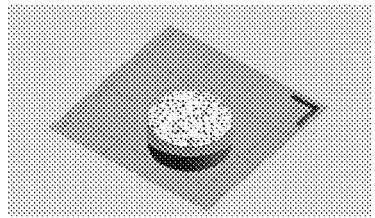
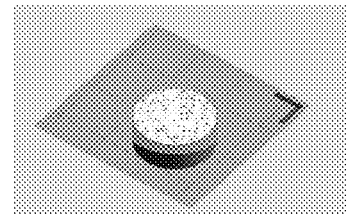
FIG. 25A          FIG. 25B          FIG. 25C
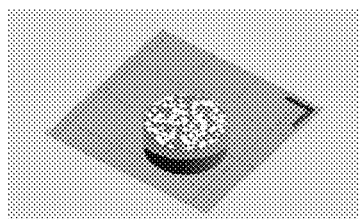
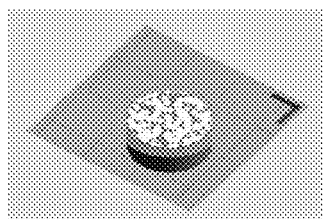
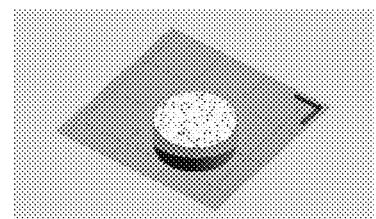
FIG. 25D          FIG. 25E          FIG. 25F
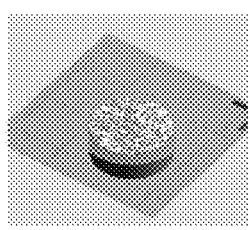
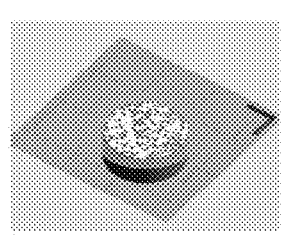
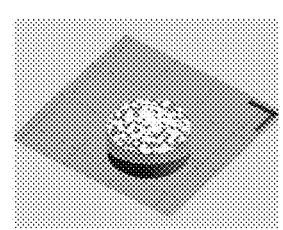
FIG. 26A          FIG. 26B          FIG. 26C

METHOD AND SYSTEM FOR FABRICATING OBJECT FEATURING PROPERTIES OF A HARD TISSUE

RELATED APPLICATIONS

This application is a continuation of U.S. patent application Ser. No. 16/632,548 filed on Jan. 21, 2020, which is a National Phase of PCT Patent Application No. PCT/IL2018/050843 having International Filing Date of Jul. 27, 2018, which claims the benefit of priority under 35 USC § 119(e) of U.S. Provisional Patent Application No. 62/538,026 filed on Jul. 28, 2017, which was co-filed with U.S. Provisional Patent Application Nos. 62/538,003, 62/538,006, 62/538,015 and 62/538,018.

The contents of the above applications are all incorporated by reference as if fully set forth herein in their entirety.

FIELD AND BACKGROUND OF THE INVENTION

The present invention, in some embodiments thereof, relates to additive manufacturing and, more particularly, but not exclusively, to a method and system for fabricating object featuring properties of a hard tissue by additive manufacturing.

Additive manufacturing (AM) is generally a process in which a three-dimensional (3D) object is manufactured utilizing a computer model of the objects. Such a process is used in various fields, such as design related fields for purposes of visualization, demonstration and mechanical prototyping, as well as for rapid manufacturing (RM). The basic operation of any AM system consists of slicing a three-dimensional computer model into thin cross sections, translating the result into two-dimensional position data and feeding the data to control equipment which manufacture a three-dimensional structure in a layerwise manner.

One type of AM is three-dimensional inkjet printing processes. In this process, a building material is dispensed from a dispensing head having a set of nozzles to deposit layers on a supporting structure. Depending on the building material, the layers may then be cured or solidified using a suitable device.

Various three-dimensional inkjet printing techniques exist and are disclosed in, e.g., U.S. Pat. Nos. 6,259,962, 6,569,373, 6,658,314, 6,850,334, 7,183,335, 7,209,797, 7,225,045, 7,300,619, 7,479,510, 7,500,846, 7,962,237.

Several AM processes allow additive formation of objects using more than one modeling material. For example, U.S. Pat. No. 9,031,680 of the present Assignee, discloses a system which comprises a solid freeform fabrication apparatus having a plurality of dispensing heads, a building material supply apparatus configured to supply a plurality of building materials to the fabrication apparatus, and a control unit configured for controlling the fabrication and supply apparatus. The system has several operation modes. In one mode, all dispensing heads operate during a single building scan cycle of the fabrication apparatus. In another mode, one or more of the dispensing heads is not operative during a single building scan cycle or part thereof.

The building materials may include modeling materials and support materials, which form the object and the temporary support constructions supporting the object as it is being built, respectively.

The modeling material (which may include one or more material(s), included in one or more formulations) is deposited to produce the desired object/s.

The support material, also known in the art as "supporting material", (which may include one or more material(s)) is used, with or without modeling material elements, is used to support specific areas of the object during building and for assuring adequate vertical placement of subsequent object layers. For example, in cases where objects include overhanging features or shapes, e.g. curved geometries, negative angles, voids, and the like, objects are typically constructed using adjacent support constructions, which are used during the printing.

In all cases, the support material is deposited in proximity of the modeling material, enabling the formation of complex object geometries and filling of object voids.

In all of the currently practiced technologies, the deposited support material and modeling material are hardened, typically upon exposure to a curing condition (e.g., curing energy), to form the required layer shape. After printing completion, support structures are removed to reveal the final shape of the fabricated 3D object.

When using currently available commercial print heads, such as ink-jet printing heads, the support material should have a relatively low viscosity (about 10-20 cPs) at the working, i.e., jetting, temperature, such that it can be jetted. Further, the support material should harden rapidly in order to allow building of subsequent layers. Additionally, the hardened support material should have sufficient mechanical strength for holding the model material in place, and low distortion for avoiding geometrical defects.

Known methods for removal of support materials include mechanical impact (applied by a tool or water-jet), as well as chemical methods, such as dissolution in a solvent, with or without heating. The mechanical methods are labor intensive and are often unsuited for small intricate parts.

For dissolving the support materials, the fabricated object is often immersed in water or in a solvent that is capable of dissolving the support materials. The solutions utilized for dissolving the support material are also referred to herein and in the art as "cleaning solutions". In many cases, however, the support removal process may involve hazardous materials, manual labor and/or special equipment requiring trained personnel, protective clothing and expensive waste disposal. In addition, the dissolution process is usually limited by diffusion kinetics and may require very long periods of time, especially when the support constructions are large and bulky. Furthermore, post-processing may be necessary to remove traces of a 'mix layer' on object surfaces. The term "mix layer" refers to a residual layer of mixed hardened model and support materials formed at the interface between the two materials on the surfaces of the object being fabricated, by model and support materials mixing into each other at the interface between them.

Additionally, methods requiring high temperatures during support removal may be problematic since there are model materials that are temperature-sensitive, such as waxes and certain flexible materials. Both mechanical and dissolution methods for removal of support materials are especially problematic for use in an office environment, where ease-of-use, cleanliness and environmental safety are major considerations.

Water-soluble materials for 3D building are described, for example, in U.S. Pat. No. 6,228,923, where a water soluble thermoplastic polymer—Poly(2-ethyl-2-oxazoline)—is taught as a support material in a 3D building process involving high pressure and high temperature extrusion of ribbons of selected materials onto a plate.

A water-containing support material comprising a fusible crystal hydrate is described in U.S. Pat. No. 7,255,825.

Formulations suitable for forming a hardened support material in building a 3D object are described, for example, in U.S. Pat. Nos. 7,479,510, 7,183,335 and 6,569,373, all to the present Assignee. Generally, the compositions disclosed in these patents comprise at least one UV curable (reactive) component, e.g., an acrylic component, at least one non-UV curable component, e.g. a polyol or glycol component, and a photoinitiator. After irradiation, these compositions provide a semi-solid or gel-like material capable of dissolving or swelling upon exposure to water, to an alkaline or acidic solution or to a water detergent solution.

Besides swelling, another characteristic of such a support material may be the ability to break down during exposure to water, to an alkaline or acidic solution or to a water detergent solution because the support material is made of hydrophilic components. During the swelling process, internal forces cause fractures and breakdown of the hardened support. In addition, the support material can contain a substance that liberates bubbles upon exposure to water, e.g. sodium bicarbonate, which transforms into $CO_2$ when in contact with an acidic solution. The bubbles aid in the process of removal of support from the model.

Several additive manufacturing processes allow additive formation of objects using more than one modeling material. For example, U.S. Patent Application having Publication No. 2010/0191360, of the present Assignee, discloses a system which comprises a solid freeform fabrication apparatus having a plurality of dispensing heads, a building material supply apparatus configured to supply a plurality of building materials to the fabrication apparatus, and a control unit configured for controlling the fabrication and supply apparatus. The system has several operation modes. In one mode, all dispensing heads operate during a single building scan cycle of the fabrication apparatus. In another mode, one or more of the dispensing heads is not operative during a single building scan cycle or part thereof.

In a 3D inkjet printing process such as Polyjet™ (Stratasys Ltd., Israel), the building material is selectively jetted from one or more printing heads and deposited onto a fabrication tray in consecutive layers according to a predetermined configuration as defined by a software file.

Additive Manufacturing processes have been used to form rubber-like materials. For example, rubber-like materials are used in PolyJet™ systems as described herein. These materials are formulated to have relatively low viscosity permitting dispensing, for example by inkjet, and to develop Tg which is lower than room temperature, e.g., −10° C. or lower. The latter is obtained by formulating a product with relatively low degree of cross-linking and by using monomers and oligomers with intrinsic flexible molecular structure (e.g., acrylic elastomers).

An exemplary family of Rubber-like materials usable in PolyJet™ systems (marketed under the trade name "Tango™" family) offers a variety of elastomer characteristics of the obtained hardened material, including Shore A hardness, Elongation at break, Tear Resistance and Tensile strength. The softest material in this family features a Shore A hardness of 27.

Another family of Rubber-like materials usable in PolyJet™ systems (marketed under the trade name "Agilus™" family) is described in PCT International Application No. IL2017/050604 (Published as WO2017/208238), by the present assignee, and utilizes a curable elastomeric formulation that comprises an elastomeric curable material and silica particles.

SUMMARY OF THE INVENTION

According to an aspect of some embodiments of the present invention there is provided a method of additive manufacturing an object featuring properties of a hard bodily tissue, the method comprises: dispensing and solidifying (e.g., exposing to a curing condition) plurality of non-biological material formulations (e.g., building material formulations or modeling material formulations, as described herein) to sequentially form a plurality of hardened layers in a configured pattern corresponding to a shape of the object, wherein for at least a portion of the layers, the dispensing comprises forming voxel elements containing different material formulations at interlaced locations to form a three-dimensional textured region spanning over the portion, and wherein the material formulations and the interlaced locations are selected such that the textured region exhibits, once hardened, a stress variation of at most ±20% over a strain range of from about 0.1% to about 0.3%.

According to some of any of the embodiments of the invention the interlaced locations are selected according to a modulating function.

According to some embodiments of the invention the modulating function comprises a noise function. According to some embodiments of the invention the modulating function comprises a simplex noise function. According to some embodiments of the invention the modulating function comprises an open simplex noise function. According to some embodiments of the invention the function comprises a Worley noise function. According to some embodiments of the invention the function comprises a Perlin noise function. According to some embodiments of the invention the function comprises a wavelet noise function. According to some embodiments of the invention the modulating function comprises a periodic function. According to some embodiments of the invention the modulating function has a period of 2 or less millimeters. According to some embodiments of the invention the modulating function comprises an aperiodic function.

According to some of any of the embodiments of the invention the material formulations comprise a first material formulation (e.g., a building material formulation) which provides, upon the solidifying, a first material, and a second material formulation (e.g., a building material formulation) which provides, upon the solidifying, a second material, wherein the interlaced locations are selected to form a plurality of texture element within the textured region, each texture element having an interior portion made of the second material at least partially surrounded by a wall portion made of the first material.

According to some of any of the embodiments of the invention the wall portion is harder than the interior portion.

According to some of any of the embodiments of the invention the material formulations comprise a first material formulation (e.g., a building material formulation) which provides, upon the solidifying, a material having a tensile strength of from about 40 to about 60 MPa according to ASTM D-638-03 and a modulus of elasticity of from about 1000 MPa to about 2600 MPa according to ASTM D-638-04, and a second material formulation (e.g., a building material formulation) which provides, upon the solidifying, a material having a modulus of elasticity of from about 10 kPa to about 100 kPa according to ASTM D-575.

According to some of any of the embodiments of the invention the material formulations comprise a first material formulation (e.g., a building material formulation) which provides, upon the solidifying, a material having a tensile strength of from about 40 to about 60 MPa according to ASTM D-638-03 and a modulus of elasticity of from about 1000 MPa to about 2600 MPa according to ASTM D-638-04, and a second material formulation (e.g., a building material formulation) which provides, upon the solidifying, a material selected from the group consisting of (i) a material having a modulus of elasticity of from about 10 kPa to about 100 kPa or from about 10 kPa to about 50 kPa according to ASTM D-575; (ii) a material having a modulus of elasticity of from about 0.1 MPa to about 1 MPa according to ASTM D-575; and (iii) a material featuring a Shore A hardness lower than 10 or a Shore 00 hardness lower than 40 or lower than 30.

According to some of any of the embodiments of the invention the material formulations comprise a third material formulation (e.g., a building material formulation) featuring (e.g., upon exposure to a curing condition) at least one of: a viscosity of no more than 10000 centipoises; Shear loss modulus to Shear storage modulus ratio greater than 1; a Shear modulus lower than 20 kPa; flowability when subjected to a positive pressure of no more than 1 bar; a shear-thinning and/or thixotropic behavior; and a thermal-thinning behavior.

According to some of any of the embodiments of the invention the dispensing comprises dispensing at least one of the material formulations (e.g., a building material formulation) to form a shell at least partially surrounding the textured region, such that once the textured region and the shell are hardened, a hardness of the shell is higher than a hardness of the textured region.

According to some of any of the embodiments of the invention the dispensing comprises dispensing at least one of the material formulations (e.g., a building material formulation) to form a flexible annulus structure in the shell, wherein an interior of the annulus structure is made of the same material formulation or material formulations as the shell.

According to some of any of the embodiments of the invention the dispensing comprises dispensing at least one of the material formulations (e.g., building material formulations) to form on the shell a structure having a shape of a soft tissue element.

According to some of any of the embodiments of the invention the dispensing comprises dispensing at least one of the material formulations (e.g., building material formulations) to form a coating over the shell, such that once the textured region, the shell, and the coating are hardened, a hardness of the coating is higher than a hardness of the shell.

According to some of any of the embodiments of the invention the dispensing comprises dispensing at least one of the material formulations (e.g., building material formulations) to form on the coating a structure having a shape of a soft tissue element.

According to some of any of the embodiments of the invention the dispensing comprises dispensing at least one of the material formulations (e.g., a building material formulation) to form a core surrounded by the textured region and/or the shell, such that once the textured region and the core are hardened, a hardness of the textured region is higher than a hardness of the core. According to some embodiments of the invention the dispensing comprises dispensing at least one of the material formulations (e.g., a building material formulation) to form a section having a shape of a bone tumor, and having mechanical properties that differ from mechanical properties of any voxel adjacent to the section outside the section.

According to an aspect of some embodiments of the present invention there is provided a method of additive manufacturing an object featuring properties of a hard tissue, the method comprises: dispensing and solidifying (e.g., exposing to a curing condition) a plurality of non-biological material formulations to sequentially form a plurality of hardened layers in a configured pattern corresponding to a shape of the object, wherein for at least a portion of the layers, the dispensing comprises forming voxel elements containing different material formulations (e.g., building material formulations) at interlaced locations to form a three-dimensional textured region spanning over the portion, the interlaced locations being selected to form a plurality of texture elements within the textured region, each texture element having an interior portion at least partially surrounded by a wall portion, wherein the interior and the wall portions are made of different material formulations, wherein a diameter of the interior portion is from about 0.1 mm to about 3 mm, and wherein a thickness of the interior portion is from about 0.1 mm to about 2 mm.

According to an aspect of some embodiments of the present invention there is provided an object made of a plurality of non-biological materials and being fabricatable by the method as delineated above and optionally and preferably as further detail below.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 is a schematic illustration of a textured region having a plurality of texture elements, according to some embodiments of the present invention;

FIGS. 6A and 6B are schematic illustrations of objects that can be fabricated according to some embodiments of the present invention by AM and that have mechanical and/or textural properties resembling those of a hard tissue;

FIGS. 25A-25F are computer object data visualizations describing several combinations of material formulations used in experiments performed according to some embodiments of the present invention to investigate the effect of formulation ratios on the mechanical properties of three-dimensional printed objects.

FIGS. 26A-26D are computer object data visualizations describing several combinations of material formulations used in experiments performed according to some embodiments of the present invention to investigate the effect of cell size on the mechanical properties of three-dimensional printed objects.

DESCRIPTION OF SPECIFIC EMBODIMENTS OF THE INVENTION

Figure 1A:
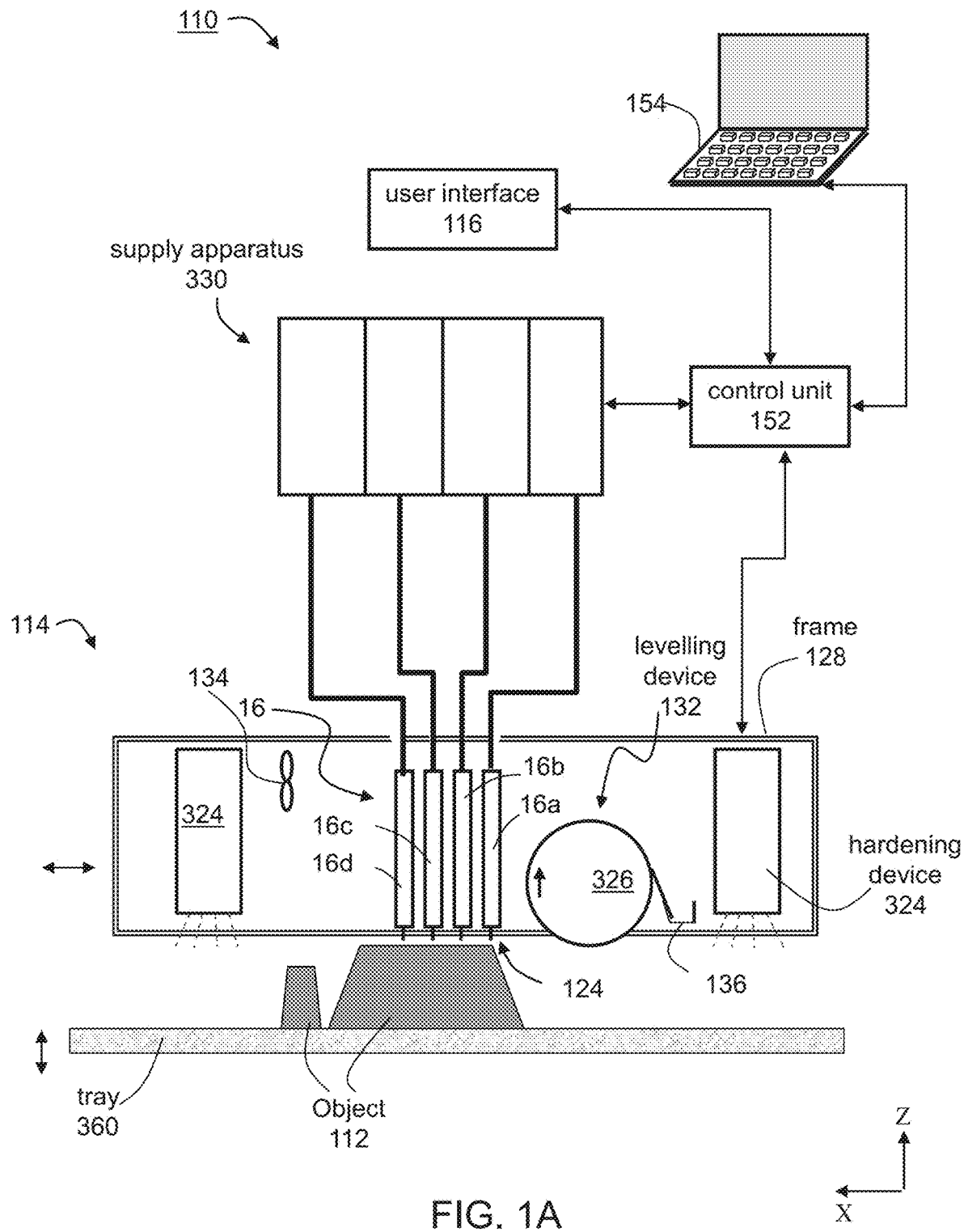
FIGS. 1A-1D are schematic illustrations of an additive manufacturing system according to some embodiments of the invention.

The present invention, in some embodiments thereof, relates to additive manufacturing and, more particularly, but not exclusively, to a method and system for fabricating object featuring properties of a hard tissue by additive manufacturing.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The method and system of the present embodiments manufacture three-dimensional objects based on computer object data in a layerwise manner by forming a plurality of layers in a configured pattern corresponding to the shape of the objects. The computer object data can be in any known format, including, without limitation, a Standard Tessellation Language (STL) or a StereoLithography Contour (SLC) format, Virtual Reality Modeling Language (VRML), Additive Manufacturing File (AMF) format, Drawing Exchange Format (DXF), Polygon File Format (PLY) or any other format suitable for Computer-Aided Design (CAD).

The term "object" as used herein refers to a whole object or a part thereof.

Each layer is formed by additive manufacturing apparatus which scans a two-dimensional surface and patterns it. While scanning, the apparatus visits a plurality of target locations on the two-dimensional layer or surface, and decides, for each target location or a group of target locations, whether or not the target location or group of target locations is to be occupied by building material formulation, and which type of building material formulation is to be delivered thereto. The decision is made according to a computer image of the surface.

In preferred embodiments of the present invention the AM comprises three-dimensional printing, more preferably three-dimensional inkjet printing. In these embodiments a building material formulation is dispensed from a dispensing head having a set of nozzles to deposit building material formulation in layers on a supporting structure. The AM apparatus thus dispenses building material formulation in target locations which are to be occupied and leaves other target locations void. The apparatus typically includes a plurality of dispensing heads, each of which can be configured to dispense a different building material formulation. Thus, different target locations can be occupied by different building material formulations. The types of building material formulations can be categorized into two major categories: modeling material formulation and support material formulation. The support material formulation serves as a supporting matrix or construction for supporting the object or object parts during the fabrication process and/or other purposes, e.g., providing hollow or porous objects. Support constructions may additionally include modeling material formulation elements, e.g. for further support strength.

The modeling material formulation is generally a composition which is formulated for use in additive manufacturing and which is able to form a three-dimensional object on its own, i.e., without having to be mixed or combined with any other substance.

Herein throughout, the phrase "uncured building material" collectively describes the materials that are dispensed during the fabrication process so as to sequentially form the layers, as described herein. This phrase encompasses uncured materials (also referred to herein as building material formulation(s)) dispensed so as to form the printed object, namely, one or more uncured modeling material formulation(s), and uncured materials dispensed so as to form the support, namely uncured support material formulations.

Herein, the dispensed materials are also referred to collectively as "material formulations". The material formulations provide, typically when hardened (unless indicated otherwise), typically hardened upon exposure to a curing condition as defined herein (unless indicated otherwise), to form a respective material.

Herein throughout, the phrases "cured modeling material" and "hardened modeling material", which are used interchangeably, describe the part of the building material that forms a model object, as defined herein, upon exposing the dispensed building material to curing, and following removal of the support material. The cured or hardened modeling material can be a single hardened material or a mixture of two or more hardened materials, depending on the modeling material formulations used in the method, as described herein.

Herein throughout, the phrase "modeling material formulation", which is also referred to herein interchangeably as "modeling formulation", describes a part of the uncured building material which is dispensed so as to form the model object, as described herein. The modeling formulation is an uncured modeling formulation, which, upon exposure to a curing condition, forms the final object or a part thereof.

An uncured building material can comprise one or more modeling formulations, and can be dispensed such that different parts of the model object are made upon curing different modeling formulations, and hence are made of different cured modeling materials or different mixtures of cured modeling materials.

Herein throughout, the phrase "hardened support material" is also referred to herein interchangeably as "cured support material" or simply as "support material" and describes the part of the building material that is intended to support the fabricated final object during the fabrication process, and which is removed once the process is completed and a hardened modeling material is obtained.

Herein throughout, the phrase "support material formulation", which is also referred to herein interchangeably as "support formulation" or simply as "formulation", describes a part of the uncured building material which is dispensed so as to form the support material, as described herein. The support material formulation is an uncured formulation. When a support material formulation is a curable formulation, it forms, upon exposure to a curing condition, a hardened support material.

Support materials, which can be either liquid or liquid-like materials or hardened, typically gel or gel-like materials, are also referred to herein as sacrificial materials, which are removable after layers are dispensed and exposed to a curing energy, to thereby expose the shape of the final object.

Herein and in the art, the term "gel" describes a material, often referred to as a semi-solid material, which comprises a three-dimensional solid network, typically made of fibrous structures chemically or physically linked therebetween, and a liquid phase encaged within this network. Gels are typically characterized by a consistency of a solid (e.g., are non-fluidic), and feature relatively low Tensile strength, relatively low Shear Modulus, e.g., lower than 100 kPa, and a Shear Loss Modulus to Shear Storage modulus (tan delta, $G''/G'$) value lower than 1. Gels can be characterized as flowable when subjected to a positive pressure of at least 0.5 bar, preferably at least 1 bar, or higher, or, alternatively, as non-flowable when subject to a pressure lower than 1 bar or lower than 0.5 bar or of 0.3 bar or lower.

Gel-like materials according to the present embodiments are typically soft materials, which can be gels or solids, which feature mechanical and rheological properties of a gel.

Currently practiced support materials typically comprise a mixture of curable and non-curable materials, and are also referred to herein as gel-like support material or as gel support material.

Currently practiced support materials are typically water miscible, or water-dispersible or water-soluble.

Herein throughout, the term "water-miscible" describes a material which is at least partially dissolvable or dispersible in water, that is, at least 50% of the molecules move into the water upon mixture. This term encompasses the terms "water-soluble" and "water dispersible".

Herein throughout, the term "water-soluble" describes a material that when mixed with water in equal volumes or weights, a homogeneous solution is formed.

Herein throughout, the term "water-dispersible" describes a material that forms a homogeneous dispersion when mixed with water in equal volumes or weights.

Herein throughout, the phrase "dissolution rate" describes a rate at which a substance is dissolved in a liquid medium. Dissolution rate can be determined, in the context of the present embodiments, by the time needed to dissolve a certain amount of a support material. The measured time is referred to herein as "dissolution time".

The gel or gel-like materials can be obtained, in some embodiments of the present invention using any of the known curable formulations that provide, when exposed to a curing condition as described herein, a hardened support material as known in the art is usable in the context of these embodiments, typically formulations that provide, when hardened, a material that is water-soluble or water-miscible or water-breakable, and/or which is removal by physical means (e.g., water jet) or chemical means (e.g., a cleaning solution) as known in the art.

According to embodiments, the curable support material formulation provides, upon exposure to a curing condition, a hardened, gel or gel-like support material featuring at least one of:

a Shear loss modulus G" to Shear storage modulus G' ratio (tan delta) that is lower than 1;

flowability and/or breakability when subjected to a liquid pressure higher than 0.5 bar or higher than 1 bar; and water-solubility or water-miscibility, as defined herein.

Exemplary curable support material formulations include one or more curable materials, preferably hydrophilic or amphiphilic curable materials, such as, for example, described herein, further preferably mono-functional curable materials; one or more non-curable materials, preferably hydrophilic or amphiphilic polymeric materials, such as, for example, described herein, and one or more initiators, for promoting the hardening of the curable materials.

Exemplary additional support material formulations include, but are not limited, those marketed as SUP705, SUP706 and SUP707. The hardened gel or gel-like materials obtained upon exposing these formulations to a curing condition (typically UV radiation) can be removed using cleaning solutions and/or physical means as recommended for these formulations.

Herein throughout, whenever the phrase "weight percents" is indicated in the context of embodiments of a formulation (e.g., a building material formulation), it is meant weight percents of the total weight of the respective formulation or formulation system as described herein.

The phrase "weight percents" is also referred to herein as "% by weight" or "% wt.".

Herein throughout, some embodiments of the present invention are described in the context of the additive manufacturing being a 3D inkjet printing. However, other additive manufacturing processes, such as, but not limited to, SLA and DLP, are contemplated.

An uncured building material can comprise one or more modeling formulations, and can be dispensed such that different parts of the object are made, upon curing, of different cured modeling formulations or different combinations thereof, and hence are made of different cured modeling materials or different mixtures of cured modeling materials.

The formulations forming the building material (modeling material formulations and support material formulations) comprise one or more curable materials, which, when exposed to curing energy, form hardened (cured) material.

Herein throughout, a "curable material" is a compound (typically a monomeric or oligomeric compound, yet optionally a polymeric material) which, when exposed to a curing condition (e.g., curing energy), as described herein, solidifies or hardens to form a cured material. Curable materials are typically polymerizable materials, which undergo polymerization and/or cross-linking when exposed to suitable condition, typically a source of energy.

A curable material, according to the present embodiments, can harden or solidify (cure) while being exposed to a curing condition which can be a curing energy, and/or to another curing condition such as contact with a chemical reagent or exposure to the environment.

The terms "curable" and "solidifiable" as used herein are interchangeable.

The polymerization can be, for example, free-radical polymerization, cationic polymerization or anionic polymerization, and each can be induced when exposed to curing energy such as, for example, radiation, heat, etc., as described herein.

In some of any of the embodiments described herein, a curable material is a photopolymerizable material, which polymerizes and/or undergoes cross-linking upon exposure to radiation, as described herein, and in some embodiments the curable material is a UV-curable material, which polymerizes and/or undergoes cross-linking upon exposure to UV radiation, as described herein.

In some embodiments, a curable material as described herein is a photopolymerizable material that polymerizes via photo-induced free-radical polymerization. Alternatively, the curable material is a photopolymerizable material that polymerizes via photo-induced cationic polymerization.

In some of any of the embodiments described herein, a curable material can be a monomer, an oligomer or a short-chain polymer, each being polymerizable and/or cross-linkable as described herein.

In some of any of the embodiments described herein, when a curable material is exposed to curing condition (e.g., radiation), it hardens (solidifies, cures) by any one, or combination, of chain elongation and cross-linking.

In some of any of the embodiments described herein, a curable material is a monomer or a mixture of monomers which can form a polymeric material upon a polymerization reaction, when exposed to curing energy at which the polymerization reaction occurs. Such curable materials are also referred to herein as monomeric curable materials.

In some of any of the embodiments described herein, a curable material is an oligomer or a mixture of oligomers which can form a polymeric material upon a polymerization reaction, when exposed to curing energy at which the polymerization reaction occurs. Such curable materials are also referred to herein as oligomeric curable materials.

In some of any of the embodiments described herein, a curable material, whether monomeric or oligomeric, can be a mono-functional curable material or a multi-functional curable material.

Herein, a mono-functional curable material comprises one functional group that can undergo polymerization when exposed to curing energy (e.g., radiation).

A multi-functional curable material comprises two or more, e.g., 2, 3, 4 or more, functional groups that can undergo polymerization when exposed to curing energy. Multi-functional curable materials can be, for example, di-functional, tri-functional or tetra-functional curable materials, which comprise 2, 3 or 4 groups that can undergo polymerization, respectively. The two or more functional groups in a multi-functional curable material are typically linked to one another by a linking moiety, as defined herein. When the linking moiety is an oligomeric or polymeric moiety, the multi-functional group is an oligomeric or polymeric multi-functional curable material. Multi-functional curable materials can undergo polymerization when subjected to curing energy and/or act as cross-linkers.

It is noted that, as described in further detail hereinbelow, not all the materials in a curable formulation should be curable to render a formulation curable. Thus, herein throughout, and with respect to any formulation described herein, a formulation is defined as curable when at least one of the materials in the formulation is curable, or polymerizable, when exposed to a curing condition.

The final three-dimensional object is made of the modeling material formulation or a combination of modeling material formulations or modeling and support material formulations or modification thereof (e.g., following curing). All these operations are well-known to those skilled in the art of solid freeform fabrication.

In some exemplary embodiments of the invention an object is manufactured by dispensing two or more different modeling material formulations, each material formulation from a different dispensing head of the AM. The material formulations are optionally and preferably deposited in layers during the same pass of the printing heads. The material formulations and combination of material formulations within the layer are selected according to the desired properties of the object.

Figure 2A:
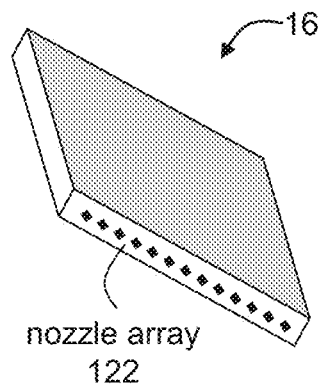
FIGS. 2A-2C are schematic illustrations of printing heads according to some embodiments of the present invention.
Figure 2B:
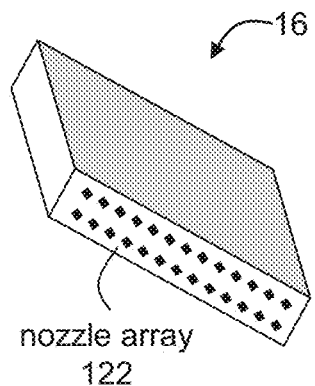
Figure 2C:
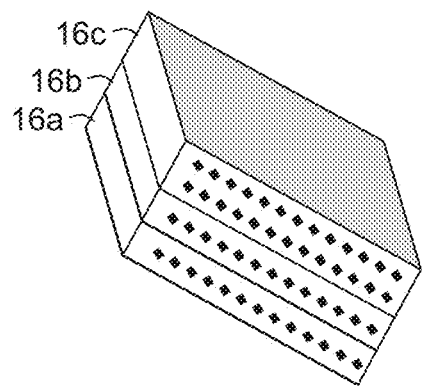

A representative and non-limiting example of a system 110 suitable for AM of an object 112 according to some embodiments of the present invention is illustrated in FIG. 1A. System 110 comprises an additive manufacturing apparatus 114 having a dispensing unit 16 which comprises a plurality of dispensing heads. Each head preferably comprises an array of one or more nozzles 122, as illustrated in FIGS. 2A-C described below, through which a liquid (uncured) building material formulation 124 is dispensed.

Preferably, but not obligatorily, apparatus 114 is a three-dimensional printing apparatus, in which case the dispensing heads are printing heads, and the building material formulation is dispensed via inkjet technology. This need not necessarily be the case, since, for some applications, it may not be necessary for the additive manufacturing apparatus to employ three-dimensional printing techniques. Representative examples of additive manufacturing apparatus contemplated according to various exemplary embodiments of the present invention include, without limitation, fused deposition modeling apparatus and fused material formulation deposition apparatus.

Each dispensing head is optionally and preferably fed via a building material formulation reservoir which may optionally include a temperature control unit (e.g., a temperature sensor and/or a heating device), and a material formulation level sensor. To dispense the building material formulation, a voltage signal is applied to the dispensing heads to selectively deposit droplets of material formulation via the dispensing head nozzles, for example, as in piezoelectric inkjet printing technology. The dispensing rate of each head depends on the number of nozzles, the type of nozzles and the applied voltage signal rate (frequency). Such dispensing heads are known to those skilled in the art of solid freeform fabrication.

Preferably, but not obligatorily, the overall number of dispensing nozzles or nozzle arrays is selected such that half of the dispensing nozzles are designated to dispense support material formulation and half of the dispensing nozzles are designated to dispense modeling material formulation, i.e. the number of nozzles jetting modeling material formulations is the same as the number of nozzles jetting support material formulation. In the representative example of FIG. 1A, four dispensing heads 16a, 16b, 16c and 16d are illustrated. Each of heads 16a, 16b, 16c and 16d has a nozzle array. In this Example, heads 16a and 16b can be designated for modeling material formulation/s and heads 16c and 16d can be designated for support material formulation. Thus, head 16a can dispense a first modeling material formulation, head 16b can dispense a second modeling material formulation and heads 16c and 16d can both dispense support material formulation. In an alternative embodiment, heads 16c and 16d, for example, may be combined in a single head having two nozzle arrays for depositing support material formulation.

Yet it is to be understood that it is not intended to limit the scope of the present invention and that the number of modeling material formulation depositing heads (modeling heads) and the number of support material formulation depositing heads (support heads) may differ. Generally, the number of modeling heads, the number of support heads and the number of nozzles in each respective head or head array are selected such as to provide a predetermined ratio, a, between the maximal dispensing rate of the support material formulation and the maximal dispensing rate of modeling material formulation. The value of the predetermined ratio, a, is preferably selected to ensure that in each formed layer, the height of modeling material formulation equals the height of support material formulation. Typical values for a are from about 0.6 to about 1.5.

For example, for a=1, the overall dispensing rate of support material formulation is generally the same as the overall dispensing rate of the modeling material formulation when all modeling heads and support heads operate.

In a preferred embodiment, there are M modeling heads each having m arrays of p nozzles, and S support heads each having s arrays of q nozzles such that M×m×p=S×s×q. Each of the M×m modeling arrays and S×s support arrays can be manufactured as a separate physical unit, which can be assembled and disassembled from the group of arrays. In this embodiment, each such array optionally and preferably comprises a temperature control unit and a material formulation level sensor of its own, and receives an individually controlled voltage for its operation.

Apparatus 114 can further comprise a solidifying device 324 which can include any device configured to emit light, heat or the like that may cause the deposited material formulation to harden. For example, solidifying device 324 can comprise one or more radiation sources, which can be, for example, an ultraviolet or visible or infrared lamp, or other sources of electromagnetic radiation, or electron beam source, depending on the modeling material formulation being used. In some embodiments of the present invention, solidifying device 324 serves for curing or solidifying the modeling material formulation.

In some embodiments of the present invention apparatus 114 comprises cooling system 134 such as one or more fans or the like The dispensing head and radiation source are preferably mounted in a frame or block 128 which is preferably operative to reciprocally move over a tray 360, which serves as the working surface. In some embodiments of the present invention the radiation sources are mounted in the block such that they follow in the wake of the dispensing heads to at least partially cure or solidify the material formulations just dispensed by the dispensing heads. Tray 360 is positioned horizontally. According to the common conventions an X-Y-Z Cartesian coordinate system is selected such that the X-Y plane is parallel to tray 360. Tray 360 is preferably configured to move vertically (along the Z direction), typically downward. In various exemplary embodiments of the invention, apparatus 114 further comprises one or more leveling devices 132, e.g. a roller 326. Leveling device 326 serves to straighten, level and/or establish a thickness of the newly formed layer prior to the formation of the successive layer thereon. Leveling device 326 preferably comprises a waste collection device 136 for collecting the excess material formulation generated during leveling. Waste collection device 136 may comprise any mechanism that delivers the material formulation to a waste tank or waste cartridge.

In use, the dispensing heads of unit 16 move in a scanning direction, which is referred to herein as the X direction, and selectively dispense building material formulation in a predetermined configuration, in the course of their passage over tray 360. The building material formulation typically comprises one or more types of support material formulation and one or more types of modeling material formulation. The passage of the dispensing heads of unit 16 is followed by the curing of the modeling material formulation(s) by radiation source 126. In the reverse passage of the heads, back to their starting point for the layer just deposited, an additional dispensing of building material formulation may be carried out, according to predetermined configuration. In the forward and/or reverse passages of the dispensing heads, the layer thus formed may be straightened by leveling device 326, which preferably follows the path of the dispensing heads in their forward and/or reverse movement. Once the dispensing heads return to their starting point along the X direction, they may move to another position along an indexing direction, referred to herein as the Y direction, and continue to build the same layer by reciprocal movement along the X direction. Alternately, the dispensing heads may move in the Y direction between forward and reverse movements or after more than one forward-reverse movement. The series of scans performed by the dispensing heads to complete a single layer is referred to herein as a single scan cycle.

Once the layer is completed, tray 360 is lowered in the Z direction to a predetermined Z level, according to the desired thickness of the layer subsequently to be printed. The procedure is repeated to form three-dimensional object 112 in a layerwise manner.

In another embodiment, tray 360 may be displaced in the Z direction between forward and reverse passages of the dispensing head of unit 16, within the layer. Such Z displacement is carried out in order to cause contact of the leveling device with the surface in one direction and prevent contact in the other direction.

System 110 optionally and preferably comprises a building material formulation supply system 330 which comprises the building material formulation containers or cartridges and supplies a plurality of building material formulations to fabrication apparatus 114.

A control unit 340 controls fabrication apparatus 114 and optionally and preferably also supply system 330. Control unit 340 typically includes an electronic circuit configured to perform the controlling operations. Control unit 340 preferably communicates with a data processor 154 which transmits digital data pertaining to fabrication instructions based on computer object data, e.g., a CAD configuration represented on a computer readable medium in a form of a Standard Tessellation Language (STL) format or the like. Typically, control unit 340 controls the voltage applied to each dispensing head or nozzle array and the temperature of the building material formulation in the respective printing head.

Once the manufacturing data is loaded to control unit 340 it can operate without user intervention. In some embodiments, control unit 340 receives additional input from the operator, e.g., using data processor 154 or using a user interface 116 communicating with unit 340. User interface 116 can be of any type known in the art, such as, but not limited to, a keyboard, a touch screen and the like. For example, control unit 340 can receive, as additional input, one or more building material formulation types and/or attributes, such as, but not limited to, color, characteristic distortion and/or transition temperature, viscosity, electrical property, magnetic property. Other attributes and groups of attributes are also contemplated.

Figure 1B:
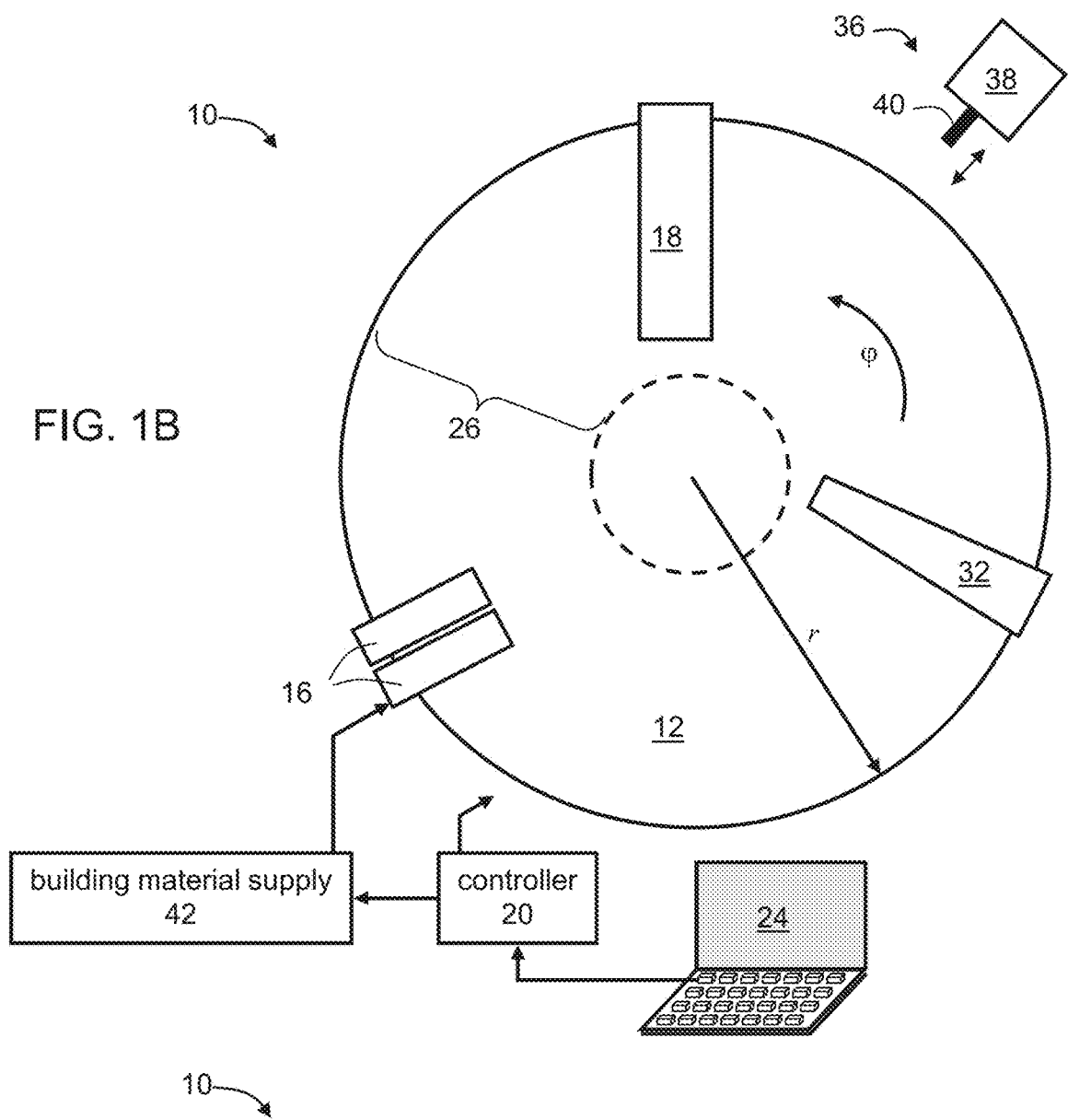
Figure 1C:
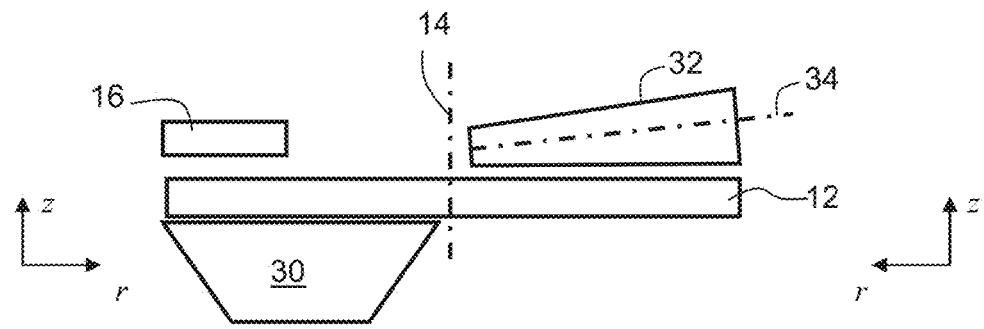
Figure 1D:
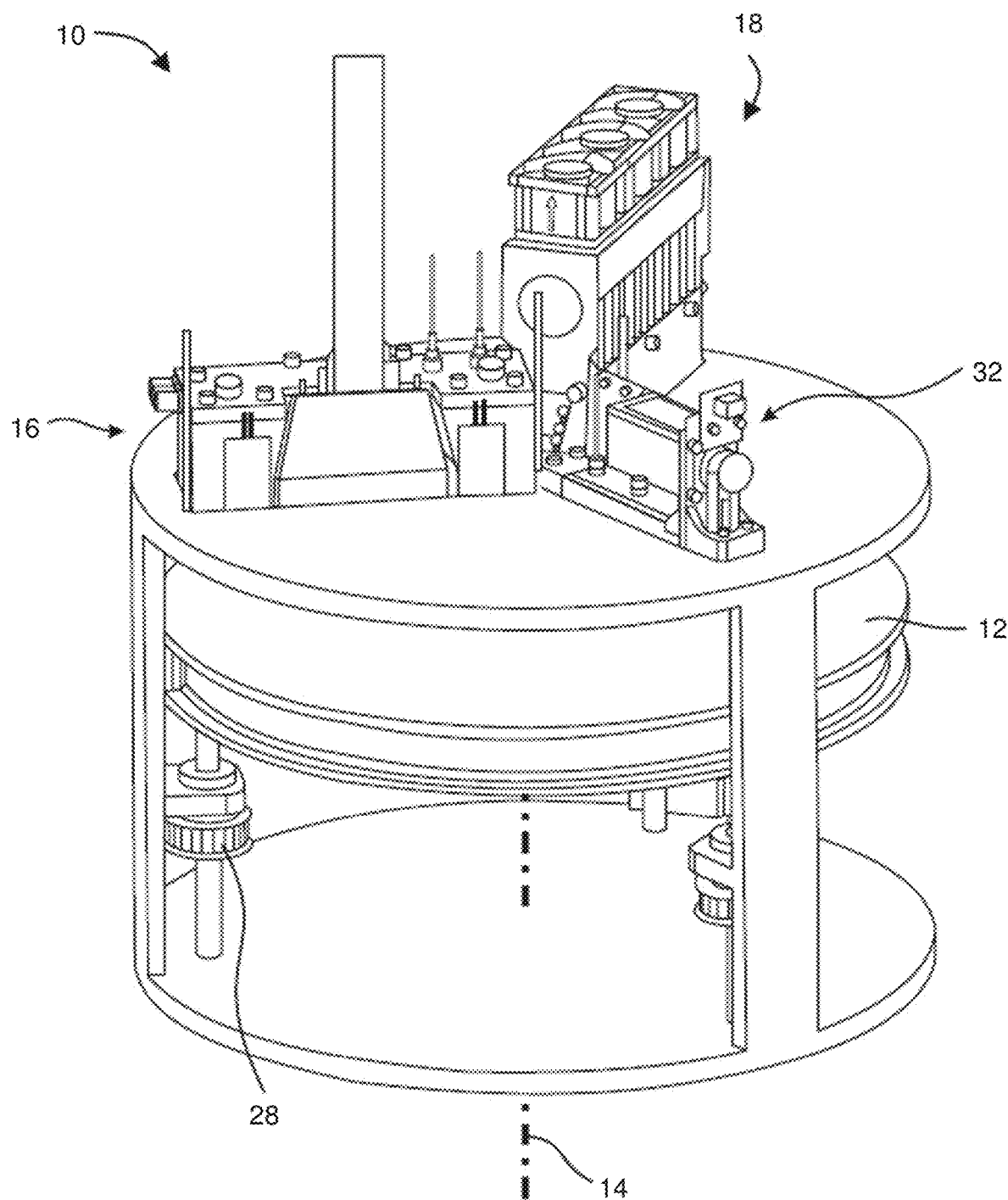

Another representative and non-limiting example of a system 10 suitable for AM of an object according to some embodiments of the present invention is illustrated in FIGS. 1B-D. FIGS. 1B-D illustrate a top view (FIG. 1B), a side view (FIG. 1C) and an isometric view (FIG. 1D) of system 10.

In the present embodiments, system 10 comprises a tray 12 and a plurality of inkjet printing heads 16, each having a plurality of separated nozzles. Tray 12 can have a shape of a disk or it can be annular. Non-round shapes are also contemplated, provided they can be rotated about a vertical axis.

Tray 12 and heads 16 are optionally and preferably mounted such as to allow a relative rotary motion between tray 12 and heads 16. This can be achieved by (i) configuring tray 12 to rotate about a vertical axis 14 relative to heads 16, (ii) configuring heads 16 to rotate about vertical axis 14 relative to tray 12, or (iii) configuring both tray 12 and heads 16 to rotate about vertical axis 14 but at different rotation velocities (e.g., rotation at opposite direction). While the embodiments below are described with a particular emphasis on configuration (i) wherein the tray is a rotary tray that is configured to rotate about vertical axis 14 relative to heads 16, it is to be understood that the present application contemplates also configurations (ii) and (iii). Any one of the embodiments described herein can be adjusted to be applicable to any of configurations (ii) and (iii), and one of ordinary skills in the art, provided with the details described herein, would know how to make such adjustment.

In the following description, a direction parallel to tray 12 and pointing outwardly from axis 14 is referred to as the radial direction r, a direction parallel to tray 12 and perpendicular to the radial direction r is referred to herein as the azimuthal direction φ, and a direction perpendicular to tray 12 is referred to herein is the vertical direction z.

The term "radial position," as used herein, refers to a position on or above tray 12 at a specific distance from axis 14. When the term is used in connection to a printing head, the term refers to a position of the head which is at specific distance from axis 14. When the term is used in connection to a point on tray 12, the term corresponds to any point that belongs to a locus of points that is a circle whose radius is the specific distance from axis 14 and whose center is at axis 14.

The term "azimuthal position," as used herein, refers to a position on or above tray 12 at a specific azimuthal angle relative to a predetermined reference point. Thus, radial position refers to any point that belongs to a locus of points that is a straight line forming the specific azimuthal angle relative to the reference point.

The term "vertical position," as used herein, refers to a position over a plane that intersect the vertical axis 14 at a specific point.

Tray 12 serves as a supporting structure for three-dimensional printing. The working area on which one or objects are printed is typically, but not necessarily, smaller than the total area of tray 12. In some embodiments of the present invention the working area is annular. The working area is shown at 26. In some embodiments of the present invention tray 12 rotates continuously in the same direction throughout the formation of object, and in some embodiments of the present invention tray reverses the direction of rotation at least once (e.g., in an oscillatory manner) during the formation of the object. Tray 12 is optionally and preferably removable. Removing tray 12 can be for maintenance of system 10, or, if desired, for replacing the tray before printing a new object. In some embodiments of the present invention system 10 is provided with one or more different replacement trays (e.g., a kit of replacement trays), wherein two or more trays are designated for different types of objects (e.g., different weights) different operation modes (e.g., different rotation speeds), etc. The replacement of tray 12 can be manual or automatic, as desired. When automatic replacement is employed, system 10 comprises a tray replacement device 36 configured for removing tray 12 from its position below heads 16 and replacing it by a replacement tray (not shown). In the representative illustration of FIG. 1B tray replacement device 36 is illustrated as a drive 38 with a movable arm 40 configured to pull tray 12, but other types of tray replacement devices are also contemplated.

Exemplified embodiments for the printing head 16 are illustrated in FIGS. 2A-2C. These embodiments can be employed for any of the AM systems described above, including, without limitation, system 110 and system 10.

FIGS. 2A-B illustrate a printing head 16 with one (FIG. 2A) and two (FIG. 2B) nozzle arrays 22. The nozzles in the array are preferably aligned linearly, along a straight line. In embodiments in which a particular printing head has two or more linear nozzle arrays, the nozzle arrays are optionally and preferably can be parallel to each other.

When a system similar to system 110 is employed, all printing heads 16 are optionally and preferably oriented along the indexing direction with their positions along the scanning direction being offset to one another.

When a system similar to system 10 is employed, all printing heads 16 are optionally and preferably oriented radially (parallel to the radial direction) with their azimuthal positions being offset to one another. Thus, in these embodiments, the nozzle arrays of different printing heads are not parallel to each other but are rather at an angle to each other, which angle being approximately equal to the azimuthal offset between the respective heads. For example, one head can be oriented radially and positioned at azimuthal position $\varphi_1$, and another head can be oriented radially and positioned at azimuthal position $\varphi_2$. In this example, the azimuthal offset between the two heads is $\varphi_1$-$\varphi_2$, and the angle between the linear nozzle arrays of the two heads is also $\varphi_1$-$\varphi_2$.

In some embodiments, two or more printing heads can be assembled to a block of printing heads, in which case the printing heads of the block are typically parallel to each other. A block including several inkjet printing heads 16a, 16b, 16c is illustrated in FIG. 2C.

In some embodiments, system 10 comprises a support structure 30 positioned below heads 16 such that tray 12 is between support structure 30 and heads 16. Support structure 30 may serve for preventing or reducing vibrations of tray 12 that may occur while inkjet printing heads 16 operate. In configurations in which printing heads 16 rotate about axis 14, support structure 30 preferably also rotates such that support structure 30 is always directly below heads 16 (with tray 12 between heads 16 and tray 12).

Tray 12 and/or printing heads 16 is optionally and preferably configured to move along the vertical direction z, parallel to vertical axis 14 so as to vary the vertical distance between tray 12 and printing heads 16. In configurations in which the vertical distance is varied by moving tray 12 along the vertical direction, support structure 30 preferably also moves vertically together with tray 12. In configurations in which the vertical distance is varied by heads 16 along the vertical direction, while maintaining the vertical position of tray 12 fixed, support structure 30 is also maintained at a fixed vertical position.

The vertical motion can be established by a vertical drive 28. Once a layer is completed, the vertical distance between tray 12 and heads 16 can be increased (e.g., tray 12 is lowered relative to heads 16) by a predetermined vertical step, according to the desired thickness of the layer subsequently to be printed. The procedure is repeated to form a three-dimensional object in a layerwise manner.

The operation of inkjet printing heads 16 and optionally and preferably also of one or more other components of system 10, e.g., the motion of tray 12, are controlled by a controller 20. The controller can has an electronic circuit and a non-volatile memory medium readable by the circuit, wherein the memory medium stores program instructions which, when read by the circuit, cause the circuit to perform control operations as further detailed below.

Controller 20 can also communicate with a host computer 24 which transmits digital data pertaining to fabrication instructions based on computer object data, e.g., in a form of a Standard Tessellation Language (STL) or a StereoLithography Contour (SLC) format, Virtual Reality Modeling Language (VRML), Additive Manufacturing File (AMF) format, Drawing Exchange Format (DXF), Polygon File Format (PLY) or any other format suitable for Computer-Aided Design (CAD). The object data formats are typically structured according to a Cartesian system of coordinates. In these cases, computer 24 preferably executes a procedure for transforming the coordinates of each slice in the computer object data from a Cartesian system of coordinates into a polar system of coordinates. Computer 24 optionally and preferably transmits the fabrication instructions in terms of the transformed system of coordinates. Alternatively, computer 24 can transmit the fabrication instructions in terms of the original system of coordinates as provided by the computer object data, in which case the transformation of coordinates is executed by the circuit of controller 20.

Figure 3A:
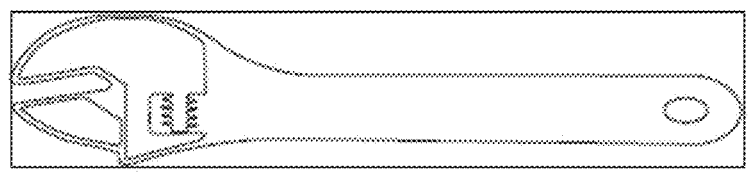
FIGS. 3A and 3B are schematic illustrations demonstrating coordinate transformations according to some embodiments of the present invention.
Figure 3B:
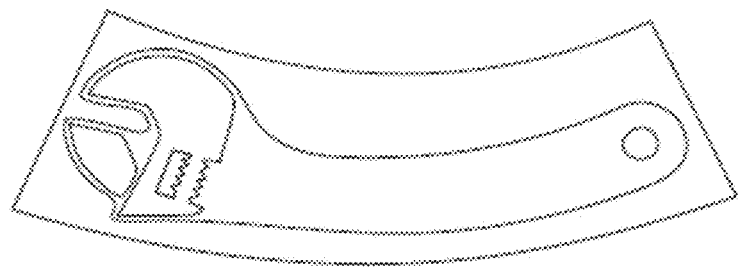

The transformation of coordinates allows three-dimensional printing over a rotating tray. In conventional three-dimensional printing, the printing heads reciprocally move above a stationary tray along straight lines. In such conventional systems, the printing resolution is the same at any point over the tray, provided the dispensing rates of the heads are uniform. Unlike conventional three-dimensional printing, not all the nozzles of the head points cover the same distance over tray 12 during at the same time. The transformation of coordinates is optionally and preferably executed so as to ensure equal amounts of excess material formulation at different radial positions. Representative examples of coordinate transformations according to some embodiments of the present invention are provided in FIGS. 3A-B, showing three slices of an object (each slice corresponds to fabrication instructions of a different layer of the objects), where FIG. 3A illustrates a slice in a Cartesian system of coordinates and FIG. 3B illustrates the same slice following an application of a transformation of coordinates procedure to the respective slice.

Typically, controller 20 controls the voltage applied to the respective component of the system 10 based on the fabrication instructions and based on the stored program instructions as described below.

Generally, controller 20 controls printing heads 16 to dispense, during the rotation of tray 12, droplets of building material formulation in layers, such as to print a three-dimensional object on tray 12.

System 10 optionally and preferably comprises one or more radiation sources 18, which can be, for example, an ultraviolet or visible or infrared lamp, or other sources of electromagnetic radiation, or electron beam source, depending on the modeling material formulation being used. Radiation source can include any type of radiation emitting device, including, without limitation, light emitting diode (LED), digital light processing (DLP) system, resistive lamp and the like. Radiation source 18 serves for curing or solidifying the modeling material formulation. In various exemplary embodiments of the invention the operation of radiation source 18 is controlled by controller 20 which may activate and deactivate radiation source 18 and may optionally also control the amount of radiation generated by radiation source 18.

In some embodiments of the invention, system 10 further comprises one or more leveling devices 32 which can be manufactured as a roller or a blade. Leveling device 32 serves to straighten the newly formed layer prior to the formation of the successive layer thereon. In some embodiments, leveling device 32 has the shape of a conical roller positioned such that its symmetry axis 34 is tilted relative to the surface of tray 12 and its surface is parallel to the surface of the tray. This embodiment is illustrated in the side view of system 10 (FIG. 1C).

The conical roller can have the shape of a cone or a conical frustum.

The opening angle of the conical roller is preferably selected such that is a constant ratio between the radius of the cone at any location along its axis 34 and the distance between that location and axis 14. This embodiment allows roller 32 to efficiently level the layers, since while the roller rotates, any point p on the surface of the roller has a linear velocity which is proportional (e.g., the same) to the linear velocity of the tray at a point vertically beneath point p. In some embodiments, the roller has a shape of a conical frustum having a height h, a radius $R_1$ at its closest distance from axis 14, and a radius $R_2$ at its farthest distance from axis 14, wherein the parameters h, $R_1$ and $R_2$ satisfy the relation $R_1/R_2=(R-h)/h$ and wherein R is the farthest distance of the roller from axis 14 (for example, R can be the radius of tray 12).

The operation of leveling device 32 is optionally and preferably controlled by controller 20 which may activate and deactivate leveling device 32 and may optionally also control its position along a vertical direction (parallel to axis 14) and/or a radial direction (parallel to tray 12 and pointing toward or away from axis 14.

In some embodiments of the present invention system 10 comprises cooling system (not shown, see FIG. 1A) such as one or more fans or the like.

In some embodiments of the present invention printing heads 16 are configured to reciprocally move relative to tray along the radial direction r. These embodiments are useful when the lengths of the nozzle arrays 22 of heads 16 are shorter than the width along the radial direction of the working area 26 on tray 12. The motion of heads 16 along the radial direction is optionally and preferably controlled by controller 20.

Some embodiments contemplate the fabrication of an object by dispensing different material formulations (e.g., building material formulations) from different dispensing heads. These embodiments provide, inter alia, the ability to select material formulations from a given number of material formulations and define desired combinations of the selected material formulations and their properties. According to the present embodiments, the spatial locations of the deposition of each material formulation with the layer is defined, either to effect occupation of different three-dimensional spatial locations by different material formulations, or to effect occupation of substantially the same three-dimensional location or adjacent three-dimensional locations by two or more different material formulations so as to allow post deposition spatial combination of the material formulations within the layer, thereby to form a composite material formulation at the respective location or locations.

Any post deposition combination or mix of modeling material formulations is contemplated. For example, once a certain material formulation is dispensed it may preserve its original properties. However, when it is dispensed simultaneously with another modeling material formulation or other dispensed material formulations which are dispensed at the same or nearby locations, a composite material formulation having a different property or properties to the dispensed material formulations is formed.

The one or more modeling material formulations comprise one or more curable materials, optionally in combination with one or more non-curable materials and further optionally in combination with an initiator, surface active agents, impact modifiers, coloring agents, thickening agents, and the like, as described herein.

Preferably the one or more modeling material formulations comprise curable materials in an amount of at least 50% by weight of the total weight of the modeling material formulations.

In some embodiments, the curable materials are UV-curable materials and the formulations further comprise one or more photoinitiators.

In some embodiments, the UV-curable materials are acrylate or methacrylates, and can include monomeric, oligomeric or polymeric acrylates and/or methacrylates.

The modeling material formulations are such that upon exposure to a curing condition (e.g., UV irradiation), the curable material polymerizes, providing a hardened (cured; solidified) material, or a plurality of hardened materials (e.g., digital materials).

The components of the modeling material formulations and the dispensing thereof are dictated by the desired properties of the final object.

The present embodiments thus enable the deposition of a broad range of material formulation combinations, and the fabrication of an object which may consist of multiple different combinations of material formulations, in different parts of the object, according to the properties desired to characterize each part of the object.

Further details on the principles and operations of an AM system suitable for the present embodiments are found in U.S. Published Application No. 20100191360, the contents of which are hereby incorporated by reference.

Figure 4:
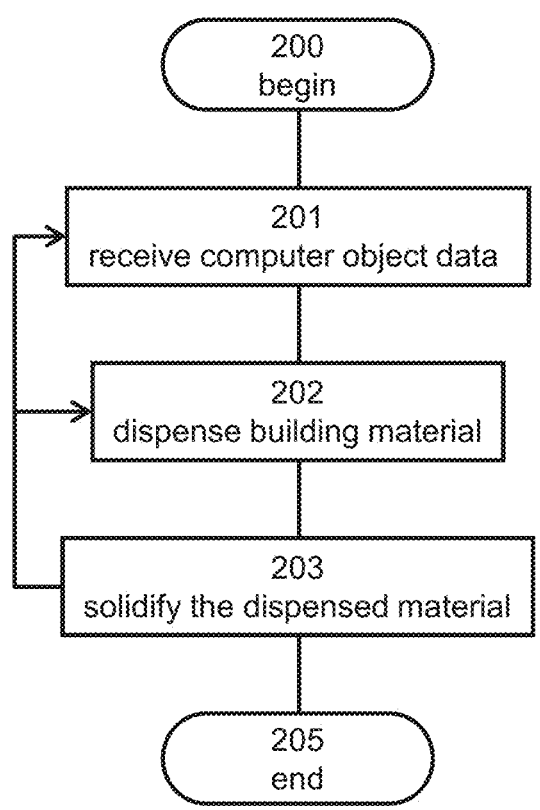
FIG. 4 is a flowchart diagram of a method particularly useful for manufacturing an object featuring properties of a hard tissue, according to some embodiments of the present invention.

FIG. 4 is a flowchart diagram of the method according to various exemplary embodiments of the present invention. The method is particularly useful for manufacturing an object featuring properties of a hard tissue.

The method begins at 200 and optionally and preferably proceeds to 201 at which computer object data in any of the aforementioned formats are obtained. An exemplified technique for obtaining the computer object data is described hereinunder with reference to FIGS. 7A and 7B.

The method can proceed to 202 at which a layer of building material formulation is dispensed. The building material formulation can be a modeling material formulation or a support material formulation. In some embodiments of the present invention the method selectively dispenses for a particular layer, one or more regions of modeling material formulations and one or more regions of support material formulation. The modeling material formulation is preferably dispensed in a configured pattern corresponding to the shape of the object and in accordance with the computer object data.

The method optionally and preferably proceeds to 203 at which the dispensed building material formulation is solidified. The type of solidification process depends on the type of dispensed material formulations. For example, when the building material formulation is UV curable, the solidification comprises applying UV radiation, when the building material formulation is curable by other radiation (e.g., infrared or visible light), the solidification comprises applying radiation at a wavelength that cures the building material formulation.

Operations 202 and 203, and in some embodiments also 201, are preferably executed sequentially a plurality of times so that a plurality of layers are sequentially dispensed and solidified. This is illustrated in FIG. 4 as loop back arrows pointing from operation 203 to operations 201 and 202. The layers are dispensed to form a stack of model layers made of a modeling material formulation, and a sacrificial structure, wherein the stack of model layers and the sacrificial structure are separable from each other in a manner that maintains the shape and size of the stack of model layers without deformation.

In some embodiments of the present invention the method dispenses digital material formulation for at least one of the layers.

The phrase "digital material formulations", as used herein and in the art, describes a combination of two or more material formulations on a microscopic scale or voxel level such that the printed zones of a specific material formulation are at the level of few voxels, or at a level of a voxel block. Such digital material formulations may exhibit new properties that are affected by the selection of types of material formulations and/or the ratio and relative spatial distribution of two or more material formulations.

In exemplary digital material formulations, the modeling or support material formulation of each voxel or voxel block, obtained upon curing, is independent of the modeling or support material formulation of a neighboring voxel or voxel block, obtained upon curing, such that each voxel or voxel block may result in a different modeling or support material formulation and the new properties of the whole object are a result of a spatial combination, on the voxel level, of several different model material formulations.

Herein throughout, whenever the expression "at the voxel level" is used in the context of a different material formulation and/or properties, it is meant to include differences between voxel blocks, as well as differences between voxels or groups of few voxels. In preferred embodiments, the properties of the whole object are a result of a spatial combination, on the voxel block level, of several different model material formulations.

In various exemplary embodiments of the invention operations 202 and 203 are executed to form, for at least a portion of layers, voxel elements containing different material formulations at interlaced locations such as to form a 3D textured region spanning over these layers. The interlaced locations are optionally and preferably selected according to a modulating function. The modulation function receives a position of a candidate voxel and provides an output value, which is then used to select the material formulation for the candidate voxel. Thus, one material formulation is designated for the candidate voxel when the output value is within one predetermined range of output values, another material formulation is designated for the candidate voxel when the output value is within another predetermined range of output values, and so on. Typically, there is at least one output value or range of output values for which no material is designated for the candidate voxel. The material designation for the candidate voxel is output for the AM system that dispense the designated material at the location of the candidate voxel.

In some embodiments of the present invention, distance fields are employed in combination with the modulating function. Typically, a voxel is selected from a 3D build space and a distance field value relative to the 3D object in the build space is determined for the selected voxel. The distance field value can then be used as an input for the modulating function. Thus, in these embodiments, the modulating function receives the position and distance field value of the candidate voxel and provides an output value, which is then used to select the material formulation for the candidate voxel as further detailed hereinabove.

The present embodiments contemplate many types of modulating functions. For example, in some embodiments of the present invention the modulating function comprises a noise function. Representative examples of noise functions suitable for being included in the modulating function include, without limitation, a simplex noise function, an open simplex noise function, a Worley noise function, a Perlin noise function, a wavelet noise function, and a value noise function. In some embodiments, the modulating function comprises a periodic function. Typically, but not necessarily, the periodic modulating function has a period of 2 or less mm. In some embodiments, the modulating function comprises an aperiodic function. Combination of two or more of these or other functions is also contemplated. A more detailed description of the concept of modulating functions and distance fields is provided in the Examples section that follows.

In some embodiments of the present invention the material formulations and interlaced locations are selected such that the textured region exhibits, once hardened, a stress variation of at most ±20% or at most ±10% or at most ±10% or at most ±5% or over a strain range of from about 0.1% to about 0.3%. These embodiments are particularly useful for fabricating an object or a region in an object that exhibits the mechanical properties of a trabecular region of a bone. The inventors have devised an AM technique that allows fabricating an object or a region in the object having a texture that resembles the typical porous texture of a trabecular region of a bone. In this AM technique, the interlaced locations are selected to form a plurality of texture elements within the textured region. FIG. 5 is a schematic illustration of a textured region 300 having a plurality of texture elements 302. Each texture element 302 has an interior portion 304 made of one material formulation, and a wall portion 306 made of another material formulation, where the wall portion 306 at least partially surrounds the interior portion.

While the texture elements 302 in FIG. 5 are illustrated as having a shape of a square, this need not necessarily be the case, since, texture elements 302 can have any other shape. For example, when a modulation function is employed, the shape of the texture elements 302 is typically effected by the output values of the function. Further, the texture elements 302 do not necessarily have the same or similar shape there amongst. Thus, two or more of texture elements 302 may have different shapes. The inventors found that a plurality of texture elements 302 can have mechanical properties that resemble the mechanical properties of a trabecular region of a bone, when the wall portions 306 are harder than the interior portions 304.

The ratio between the overall volume occupied by wall portion 306 and the overall volume occupied by interior portion 304 within textured region 300 is typically from about 0.25 to about 0.75. Typically, there are at least 20 or at least 30 or at least 40 or at least 50 or at least 60 or at least 70 or at least 80 or at least 90 or at least 100 texture elements 302 within textured region 300 at a density of from about 20 to about 100 texture elements per cubic centimeter. The size of a single texture element 302 in textured region 300 is typically from about 0.1 mm to about 3 mm or about 0.5 mm to about 3 mm in diameter along its largest dimension. The thickness of wall portion 306 is typically from about 0.1 mm to about 2 mm or from about 0.3 mm to about 2 mm.

Preferably, the stiffness of textured region 300 varies along a direction generally perpendicularly (e.g., with deviation of less than 10° from the perpendicular direction) to the outer surface of object 350, with higher stiffness as one moves closer to the outer surface and lower stiffness as one moves away from the outer surface. In some embodiments of the present invention the innermost portion 301 of region 300 is made of a material formulation having a zero (0) or close to zero (e.g., 10 or less, or 5 or less) Shore A hardness, or a Shore 00 hardness lower than 40 or lower than 30, such as the material formulation described in Example 1, below.

In some embodiments of the present invention the material formulations comprise a first material formulation which provides, when hardened (e.g., upon solidifying, e.g., upon exposure to a curing condition), a material having a tensile strength of from about 40 to about 60 MPa according to ASTM D-638-03 and a modulus of elasticity of from about 1000 MPa to about 2600 MPa according to ASTM D-638-04, and a second material formulation which provides, when hardened (e.g., upon solidifying, e.g., upon exposure to a curing condition), a material having a modulus of elasticity of from about 10 kPa to about 100 kPa or from about 10 kPa to about 50 kPa according to ASTM D-575.

A representative example of a material formulation suitable for use as the first material formulation in these embodiments is a material formulation marketed by Stratasys Ltd., Israel, under the trade name "VeroPureWhite", and a representative example of a material formulation suitable for use as the second material formulation in these embodiments is a material formulation marketed by Stratasys Ltd., Israel, under the trade name "SUP706".

In some embodiments of the present invention the material formulations comprise a first material formulation which provides, when hardened (e.g., upon solidifying, e.g., upon exposure to a curing condition), a material having a tensile strength of from about 40 to about 60 MPa according to ASTM D-638-03 and a modulus of elasticity of from about 1000 MPa to about 2600 MPa according to ASTM D-638-04, and a second material formulation which provides, when hardened (e.g., upon solidifying, e.g., upon exposure to a curing condition), a material having a modulus of elasticity of from about 0.1 MPa to about 1 MPa according to ASTM D-575. A representative example of a material formulation suitable for use as the first material formulation in these embodiments is a material formulation marketed by Stratasys Ltd., Israel, under the trade name "VeroPureWhite", and a representative example of a material formulation suitable for use as the second material formulation in these embodiments is a material formulation marketed by Stratasys Ltd., Israel, under the trade name "SUP705".

Any other formulations usable in additive manufacturing as modeling material formulations (e.g., for providing the first material and optionally the second material) or as support material formulations (e.g., for providing the second material) are contemplated. Such formulations are commercially available or can be designed by those skilled in the art.

In some embodiments of the present invention the material formulations comprise a first formulation which provides, when hardened (e.g., upon solidifying, e.g., upon exposure to a curing condition), a first material having a tensile strength of from about 40 to about 60 MPa according to ASTM D-638-03 and a modulus of elasticity of from about 1000 MPa to about 2600 MPa according to ASTM D-638-04, and a second material formulation having a zero (0) or close to zero (e.g., 10 or less, or 5 or less) Shore A hardness, or a Shore 00 hardness lower than 40 or lower than 30. The second material formulation can optionally and preferably provide, when hardened (e.g., upon solidifying, e.g., upon exposure to a curing condition), a material characterized by modulus of elasticity of from about 0.02 MPa to about 0.2 MPa according to ASTM D-575. The second material formulation can optionally and preferably provide, when hardened (e.g., upon solidifying, e.g., upon exposure to a curing condition), a material characterized by a compression modulus of from about 20 MPa to about 80 MPa.

Compression modulus can be tested, for example, by dispensing and curing the material formulation to build a cube of about 20×20×20 mm$^3$, and placing the cube between compression plates of Lloyd LR5K (Lloyd Instruments™, Ametek®, UK).

A representative example of a material formulation suitable for use as the first material formulation in these embodiments is a material formulation marketed by Stratasys Ltd., Israel, under the trade name "VeroPureWhite". A representative example of a material formulation suitable for use as the second material formulation in these embodiments is described below.

The first material formulation is preferably dispensed to form wall portions 306 and the second material formulation is preferably dispensed to form interior portions 304.

In some embodiments of the present invention the material formulations also comprise a third material formulation. Preferably, the third material formulation provides, upon solidifying (e.g., upon exposure to a curing condition), a liquid or liquid-like material, even after the solidification of the first and second material formulation. The third material formulation is particularly useful for being combined with the second material formulation within the interior portions 304. Typically, voxels of the second and third material formulations are interfaced to form interior portions 304. This can be done by a judicious selection of the predetermined range of output values that are employed for designating these material formulations to voxels identified (e.g., by means of the determined distance field value) as belonging to interior portions 304. A representative example of a formulation suitable for use as the third material formulation is described in Example 2.

The present embodiments also contemplate forming objects or regions of objects having mechanical and/or textural properties resembling those of other types of hard tissues. For example, in some embodiments of the present invention an object or a region of an object has mechanical and/or textural properties resembling of a cortical bone region. A particularly preferred example is an object that has a region having mechanical and/or textural properties resembling those of the trabecular region of a bone and a region having mechanical and/or textural properties resembling those of the cortical region of a bone. A schematic illustration of this embodiment is illustrated in FIGS. 6A and 6B. Shown is an object 350 having a textured region 300 at least partially surrounded by a shell 352. In various exemplary embodiments of the invention, once textured region 300 and shell 352 are hardened, a hardness of shell 352 is higher than a hardness of textured region. In various exemplary embodiments of the invention textured region 300 is the textured region described above. The thickness of region 300 along the build direction (the z direction in FIG. 6A) is typically from about 1 mm to about 30 mm.

The thickness of shell 352 (as measured perpendicularly to the outer surface of object 350) is typically non-uniform along object 350. For example, the shell 352 can be thinner at the end regions 351 of object 350 and thicker farther from the end regions 351 (e.g., at the middle section 353 between the two end regions 351). These embodiments are particularly useful when object 350 mimics a bone. The thickness of shell 352 preferably varies gradually as one moves away from the end regions 351 towards the middle section 353. A typical thickness of shell 352 at end regions 351 is from about 0.5 mm to about 3 mm, which is a typical thickness of the epiphysis and metaphysis portions of a bone, and a typical thickness of shell 352 at middle section 353 is from about 3 mm to about 8 mm, which is a typical thickness of the diaphysis portion of a bone. Other thicknesses are also contemplated.

Shell 352 can be made of a material formulation which is the same as the material formulation used for making wall portions 306 of textured region 300. Alternatively, shell 352 can be made of a digital material formulation combining two or more material formulations in a voxel-interlaced manner. As a representative example, a digital material formulation for shell 352 can include a combination of two material formulations referred to as material formulations $C_1$ and $C_2$. In some embodiments of the present invention, material formulation $C_1$ is the same as the material formulation used for making wall portions 306 of textured region 300, and material formulation $C_2$ can be such that provides, when hardened (e.g., upon solidifying, e.g., upon exposure to a curing condition), a material having a tensile strength of from about 20 MPa to about 40 MPa according to ASTM D-638-03 and a modulus of elasticity of from about 750 MPa to about 1500 MPa according to ASTM D-638-04. In such a combination, the ratio between the number of voxels occupied by material formulation $C_1$ and the number of voxels occupied by material formulation $C_2$ can be from about 3 to about 5. A representative example of a material formulation suitable for use as material formulation $C_1$ in these embodiments is a material formulation marketed by Stratasys Ltd., Israel, under the trade name "VeroPureWhite", and a representative example of a material formulation suitable for use as material formulation $C_2$ in these embodiments is a material formulation marketed by Stratasys Ltd., Israel, under the trade name "RGD515".

In other embodiments, material formulation $C_1$ can be such that provides, when hardened (e.g., upon solidifying, e.g., upon exposure to a curing condition), a material having a tensile strength of from about 50 MPa to about 70 MPa according to ASTM D-638-03 and a modulus of elasticity of from about 2500 MPa to about 3500 MPa according to ASTM D-638-04, and material formulation $C_2$ can by such that provides, when hardened (e.g., upon solidifying, e.g., upon exposure to a curing condition), a material having a tensile strength of from about 20 MPa to about 40 MPa according to ASTM D-638-03 and a modulus of elasticity of from about 750 MPa to about 1500 MPa according to ASTM D-638-04. Representative examples of material formulations suitable for use as material formulation $C_1$ in these embodiments is one of the material formulations marketed by Stratasys Ltd., Israel, under the trade names "RGD531" and "RGD525," and a representative example of a material formulation suitable for use as material formulation $C_2$ in these embodiments is a material formulation marketed by Stratasys Ltd., Israel, under the trade name "RGD515."

Any other formulations usable in additive manufacturing as modeling material formulations (e.g., for providing the first material and optionally the second material) or as support material formulations (e.g., for providing the second material) are contemplated. Such formulations are commercially available or can be designed by those skilled in the art.

In some embodiments of the present invention the method dispenses one or more material formulations to form one or more flexible annulus structures 354 in shell 352 (not shown in FIG. 6B). The interior of annulus structure 354 is typically made of the same material formulation or material formulations as shell 352, but the periphery of annulus structure 354 is more flexible than shell 352. The flexible annulus structures are particularly useful when it is desired to locally apply post fabrication mechanical processing operations (such as, but not limited to, drilling, reaming or screwing), which may potentially result in undesired cracks near the point of mechanical processing. The flexibility of structure 354 allows processing the interior portion of structure 354 without causing significant damage to the shell parts that surround structure 354. In experiments performed by the present inventors it was found that annulus structure 354 successfully prevents crack propagation (see, e.g., FIGS. 8J-L in the Examples section that follows). Preferably, structure 354 is marked with a different color to facilitate easy identification of the region to be processed.

A suitable material formulation for forming structure 354 can be such that provides, when hardened (e.g., upon solidifying, e.g., upon exposure to a curing condition), a material having a tensile strength of from about 2 to about 4 MPa according to ASTM D-412 and a Shore A hardness from about 25 MPa to about 35 MPa according to ASTM D-224D. A representative example of such a material formulation is a material formulation belonging to a family of material formulations marketed by Stratasys Ltd., Israel, under the trade name "Agilus™", (e.g., Agilus™30). Alternatively, an elastomeric curable formulation as described in Examples 6 herein can be used. Typical dimensions for structure 354 include, without limitation, from about 5 mm to about 20 mm in external diameter and from about 0.5 mm to about 2 mm in internal diameter.

In some embodiments of the present invention the method dispenses one or more material formulations to form on or near shell 352 one or more additional structures having a shape of a bodily element other than a bone. The additional structure is referred to below collectively as 356 and individually as 356a, 356b, 356c, etc. Typically, but not necessarily, the computer object data for the fabrication of additional structure 356 is provided separately (e.g., on a separate computer object data file from the computer object data for fabrication of object 350). A representative example of combination of computer object data to form an additional structure is provided in Example 7, below.

Representative examples of bodily elements that can be mimicked by structure 356 include, without limitation, a bone tumor 356a, a cartilage 356b, a nerve 356c, a spinal cord 356d and intervertebral disk 356e. The additional structure can in some embodiments of the present invention be a composite structure (e.g., it can have a core-shell structure) if desired. When structure 356 mimics a bone tumor 356a, the surrounding layer of structure 356a can be made of a material formulation marketed by Stratasys Ltd., Israel, under the trade name "VeroPureWhite", and the interior portion of structure 356a can be made of a digital material formulation combining two or more material formulations in a voxel-interlaced manner. A representative example of material formulations suitable for these embodiments includes a material formulation marketed by Stratasys Ltd., Israel, under the trade name "SUP705", and a material formulation marketed by Stratasys Ltd., Israel, under the trade name "SUP706," optionally also combined with material formulation marketed by Stratasys Ltd., Israel, under the trade name "VeroPureWhite", where the combination of SUP706 and VeroPureWhite is preferably at a ratio of from about 3 to about 5, e.g., about 4. Any other formulations usable in additive manufacturing as modeling material formulations (e.g., for providing the first material and optionally the second material) or as support material formulations (e.g., for providing the second material) are contemplated. Such formulations are commercially available or can be designed by those skilled in the art.

Also contemplated are embodiments in which the SUP705 formulation is replaced with a material formulation having a zero (0) or close to zero (e.g., 10 or less, or 5 or less) Shore A hardness, or a Shore 00 hardness lower than 40 or lower than 30, such as the material formulation described in Example 1, below.

In some embodiments of the present invention the thickness of shell 352 (as measured perpendicularly to the outer surface of object 350) is thinner beneath structure 356a than in regions of shell 352 surrounding the structure 356a. In some embodiments of the present invention shell 352 is not formed beneath structure 356a but is formed in regions of shell 352 surrounding the structure 356a. These embodiments can mimic a condition in which a bone tumor penetrates the cortical layer of the bone.

When structure 356 mimics a cartilage 356b (FIG. 6A), a nerve 356c (FIG. 6A) or a spinal cord 356d (FIG. 6B) it can be made of a material formulation that provide, when hardened (e.g., upon solidifying, e.g., upon exposure to a curing condition), a material having a tensile strength of from about 20 to about 40 MPa according to ASTM D-638-03 and a modulus of elasticity of from about 750 MPa to about 1500 MPa according to ASTM D-638-04. Alternatively, structure 354 can be made of a digital material formulation combining two or more material formulations in a voxel-interlaced manner. A representative example of material formulations suitable for these embodiments includes a material formulation marketed by Stratasys Ltd., Israel, under the trade name "RGD515", and a material formulation marketed by Stratasys Ltd., Israel, under the trade name "AgilusClear™" (e.g., Agilus30 Clear). Alternatively, an elastomeric curable formulation as described in Example 6 as be used.

Any other formulations usable in additive manufacturing as modeling material formulations (e.g., for providing first and second materials that feature properties as described herein) are contemplated. Such formulations are commercially available or can be designed by those skilled in the art.

When structure 356 mimics an intervertebral disk 356e (FIG. 6B), its surrounding layer can be made of a material formulation that provides, when hardened (e.g., upon solidifying, e.g., upon exposure to a curing condition), a material having a tensile strength of from about 2 to about 4 MPa according to ASTM D-412 and a Shore A hardness from about 25 MPa to about 35 MPa according to ASTM D-224D, such as, but not limited to, the material formulations marketed by Stratasys Ltd., Israel, under the trade name "AgilusClear™," (e.g., Agilus30™Clear) or an elastomeric curable formulation as described in Examples 6, and its interior portion can be made of a formulation that provides, when hardened (e.g., upon solidifying, e.g., upon exposure to a curing condition), a material having a zero (0) or close to zero (e.g., 10 or less, or 5 or less) Shore A hardness, or a Shore 00 hardness lower than 40 or lower than 30, such as the material formulation described in Example 1, below.

In some embodiments of the present invention the method dispenses one or more of the materials to form a coating 358 (not shown in FIG. 6B) over shell 352 for improving the rigidity of the outer surface of the object. Preferably, once textured region 300, shell 352, and coating 358 are hardened, a hardness of coating 358 is higher than a hardness of shell 352. Representative examples of material formulation suitable for use in the fabrication of coating 358, include, without limitation, a material formulation marketed by Stratasys Ltd., Israel, under the trade name "RGD515", and material formulation marketed by Stratasys Ltd., Israel, under the trade name "RGD450." In embodiments in which coating 358 is fabricated, any of structures 354 and 356 can optionally and preferably be formed on coating instead of on shell 352.

The present embodiments also contemplate forming a region having mechanical and/or textural properties resembling those of bone marrow tissue. In these embodiments, the method dispenses one or more of the material formulations to form a core 361 (not shown in FIG. 6B) at least partially surrounded by textured region 300 and/or shell 352. Once textured region 300 and core 361 are hardened, a hardness of textured region 300 is higher than a hardness of core 361. The mechanical and/or textural properties of core 361 preferably resembling those of bone marrow tissue. In some embodiments of the present invention portion 301 of region 300 serves as a core. Representative examples of material formulation suitable for use in the fabrication of core 361, include, without limitation, a material formulation marketed by Stratasys Ltd., Israel, under the trade name "SUP705", and material formulation marketed by Stratasys Ltd., Israel, under the trade name "SUP706."

Alternatively, core 361 can be made of a digital material formulation combining two or more material formulations in a voxel-interlaced manner. As a representative example, a digital material formulation for core 361 can include a combination of two material formulations referred to as material formulation $M_1$ and $M_2$. Representative examples of material formulation suitable for use as material formulation $M_1$ include, without limitation, a material formulation marketed by Stratasys Ltd., Israel, under the trade name "SUP705", material formulation marketed by Stratasys Ltd., Israel, under the trade name "SUP706," and a material formulation which provides, when hardened (e.g., upon solidifying, e.g., upon exposure to a curing condition), a material having a zero (0) or close to zero (e.g., 10 or less, or 5 or less) Shore A hardness, or a Shore 00 hardness lower than 40 or lower than 30, such as the material formulation described in Example 1, below. Material formulation $M_2$ is optionally and preferably a material formulation that provides upon exposure to a curing condition, a liquid or liquid-like material, even after the solidification of material formulation $M_2$. A representative example of such a material formulation is provided in Example 2, below.

The various regions and portions of object 350 can be color coded for ease of reference. Coloring can be achieved by mixing the material formulation(s) forming the respective region or portion with a material formulation having a respective color (e.g., by means of dispensing a digital material formulation, as described herein). The colors can be selected at a level of the computer object data (provided for example, in a VRML format) that is used to fabricate object 350. For example, one or more regions that are not covered by shell 352 can be colored differently than the color of shell 352 itself, and optionally and preferably also differently among themselves. As a representative example, at least one of annulus structure 354, additional structure 356a-e, can be colored differently thereamongst, and also differently from shell 352. Also contemplated, are embodiments in which regions of different properties (e.g., different thickness, different stiffness, etc.) are colored differently. The colors of the respective regions and portions of object 350 can be selected by the user, for example, by user interface 116, or computer 154 or 24.

User interface 116, or computer 154 or 24 can also be used as a supplement or alternative to the coloring embodiments described above. Specifically, the operator can point or hover above a particular region or portion of object 350, for example, using a pointer (e.g., a pointer of a computer mouse), and user interface 116, or computer 154 or 24 can display, optionally and preferably momentarily, information (e.g., mimicked structure, mechanical properties, dimensions, etc.) pertaining to the respective region.

User interface 116, or computer 154 or 24 can also be used by the operator for selecting the property (e.g., mimicked structure, mechanical properties, dimensions, thickness, texture, etc.) of one or more regions of the object. This can be done in more than one way, as will now be explained.

In some embodiments the operator uses a pointer (e.g., a pointer of a computer mouse) to point to a particular region or portion of object 350, and then selects from a menu of the user interface or computer the desired property.

In some embodiments, after the operator points to the particular region or portion he or she selects a color for the respective region or portion, wherein the color in this embodiment is used as a code for the desired property. The operator can select the color based on a look-up table that maps colors to properties. For example, different colors or hues can be used to select different thicknesses for the cortical layer of the bone, different colors can be used to select a different type of additional structure 356 etc. Preferably, the user interface or computer allows the operator to select a color gradient for the respective region. This embodiment is particularly useful when it is desired to gradually vary the property of the region. For example, a particular color gradient can be used to select a gradient in the thickness of the cortical layer, a gradient in the hardness of the trabecular bone structure, a gradient in the parameters of the modulating function that characterize the texture textured region, etc.

Once the operator has selected the color, the computer can use the color as input for adjusting, based on the color input, the distance field, modulation function and/or computer object data in accordance with the respective property. The controller 152 or 20 that receives the adjusted computer object data can control the dispensing heads to dispense the layers of the object such as to form an object having the selected properties for the respective region.

Figure 7A:
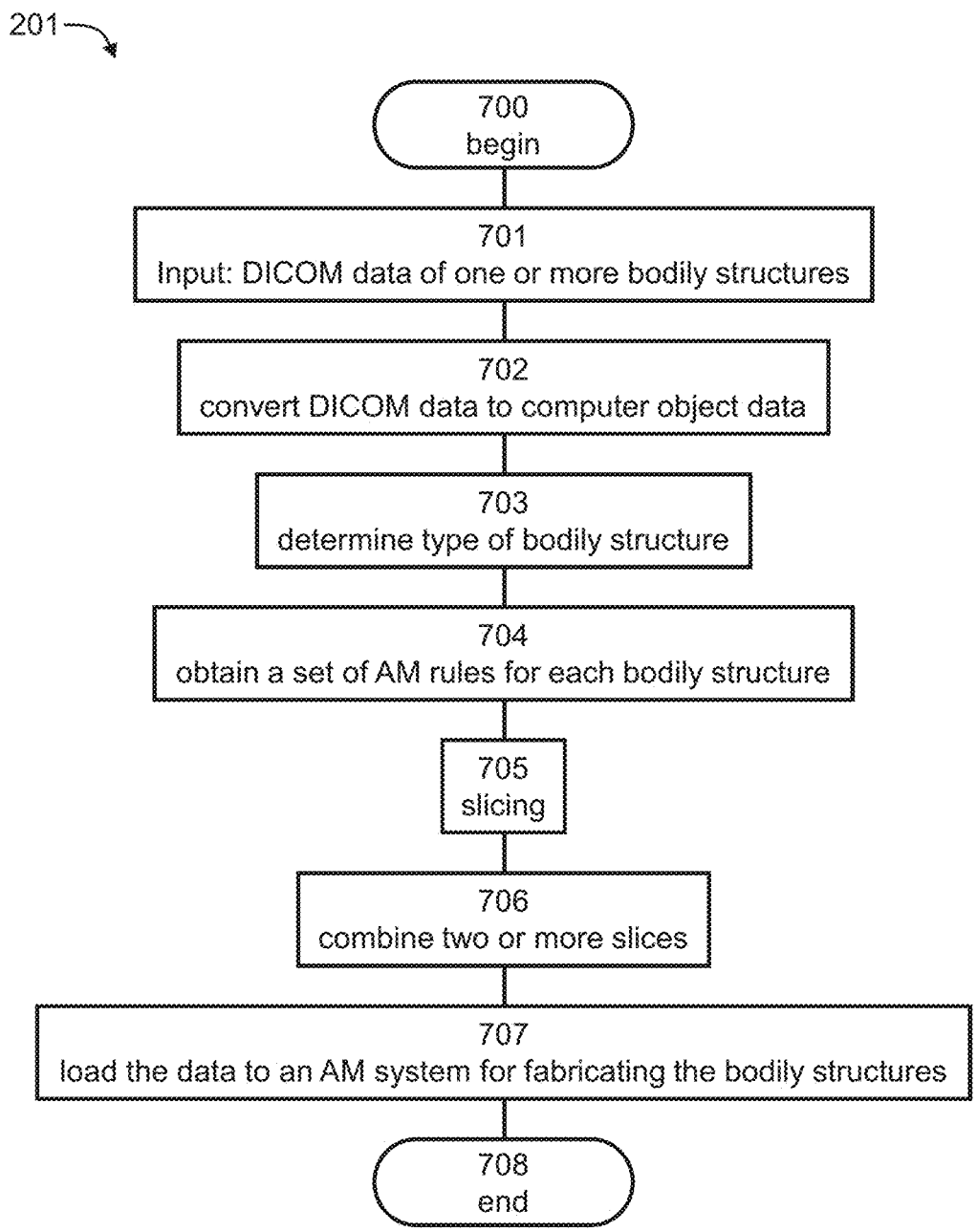
FIGS. 7A and 7B are flowchart diagrams describing an exemplified procedure which can be used according to some embodiments of the present invention for obtaining computer object data.

FIG. 7A is a flowchart diagram of an exemplified procedure which can be used according to some embodiments of the present invention for executing operation 201 above. The procedure is particularly useful for obtaining computer object data for use with system 10 or system 110. It is to be understood that, unless otherwise defined, the operations described hereinbelow can be executed either contemporaneously or sequentially in many combinations or orders of execution. Specifically, the ordering of the flowchart diagram is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The procedure begins at 700 and optionally and preferably continues to 701 at which data in a format suitable for Digital Imaging and Communications in Medicine (hereinafter DICOM data) are received.

The DICOM data can be received from an acquisition console such as, but not limited to, an MRI system, a CT imaging system, a helical CT system, a positron emission tomography (PET) system, a 2D or 3D fluoroscopic imaging system, a 2D, 3D, or 4D ultrasound imaging system, an endoscope system, a bedside monitor system, an x-ray system, and a hybrid-imaging system capable of CT, MR, PET, ultrasound or other imaging techniques. The DICOM data preferably includes one or more digital image data describing one or more bodily structures comprising one or more bodily tissue elements. In some embodiments of the present invention DICOM data preferably includes one or more digital image data describing one or more bones, in some embodiments of the present invention DICOM data preferably includes one or more digital image data describing one or more bodily structures comprising one or more bodily tissue elements other than a bone, and in some embodiments of the present invention DICOM data preferably includes one or more digital image data describing one or more bones, and also one or more digital image data describing one or more bodily structures comprising one or more bodily tissue elements other than a bone.

The procedure optionally and preferably continues to 702 at which the DICOM data are converted to computer object data. For instance, the computer object data can be in any known format, including, without limitation, a Standard Tessellation Language (STL) or a StereoLithography Contour (SLC) format, Virtual Reality Modeling Language (VRML), Additive Manufacturing File (AMF) format, Drawing Exchange Format (DXF), Polygon File Format (PLY) or any other format suitable for Computer-Aided Design (CAD), e.g., Wavefront file format (OBJ). The conversion from DICOM data to computer object data optionally and preferably includes one or more segmentation procedures, selected from the group consisting of thresholding, region growing, dynamic region growing, and the like.

Thresholding procedures exploit the differences in density of different tissues to select image pixels with a higher or equal value to a prescribed threshold value. For example, a prescribed threshold value of a thresholding procedure can be selected so that image pixels with regard to hard tissue pass the thresholding procedure, and other image pixels relating are filtered out. The thresholding procedure can be applied multiple times each time using a different threshold value, so as to obtain separate datasets for different tissue types.

Region growing procedures are typically applied after thresholding to isolate areas which have the same density range. A region growing procedure can examine neighboring pixels of initial seed points and determines whether the neighboring pixels belong to the region. The procedure is optionally and preferably performed iteratively to segment the image. For example, seed points can be selected according to different tissue types and the region growing segmentation techniques can be performed iteratively to separate image pixels as belonging to one of these tissue types. In dynamic region growing, a range of image parameters are selected in addition to the seed points. These parameters are selected to allow recognizing an image pixel as the same as the seed points.

Typically, but not necessarily, an initial background segmentation procedure is applied for removing from the DICOM data elements that do not belong to any of the tissue types of interest. Subsequent segmentation procedures can then be applied for more refined segmentation of one or more refined area of a subject's anatomy by using different segmentation techniques.

Following segmentation, the conversion from DICOM data to computer object data can also include smoothing, wrapping and/or hole-filling to compensate for artifacts within the DICOM data. A format conversion procedure can then be applied to the segmented DICOM data so as to provide the computer object data in in any of the aforementioned formats.

In some embodiments of the present invention, the input data are received from a computer readable medium as computer object data, in which case it is not necessary to obtain and convert the DICOM data. In these embodiments, it is not necessary to execute operations 701 and 702.

In any event, the computer object data preferably include data pertaining to a shape of one or more bodily structures comprising one or more bodily tissue elements as further detailed hereinabove. Whether obtained by conversion of DICOM data or received directly as such, the computer object data are optionally and preferably arranged in multiple files, each pertaining to a different bodily structure.

At 703 a type of the bodily structure to be mimicked by an additive manufactured object (e.g., bone, muscle tissue, smooth tissue, bone tumor, cartilage, disks, nerves/spinal cord, body liquid vessel) is determined for each data file. The determination can be by extracting information present in the respective computer object data file, or the respective DICOM data file, or from information associated with the respective data file.

At 704, a set of rules associated with the respective bodily structure is selected. The set of AM rules optionally and preferably include building material formulation(s) to be dispensed as well as dispensing parameters and conditions (e.g., temperature, interlacing ratios, interlacing texture). The set of AM rules can be obtained from a look-up table having an entry for each type of bodily structure, and a set of parameters associated with each such entry. In some embodiments of the present invention a subject profile is received. The subject profile typically includes one or more of weight, gender, age, ethnicity, race, clinical history, etc. In some embodiments of the present invention the subject profile also includes a genetic profile, which can encompass the genes in an entire genome of the subject, or it can encompass a specific subset of genes. The genetic profile may include genomic profile, a proteomic profile, an epigenomic profile and/or a transcriptomic profile. In embodiments in which the subject profile is received, the look-up table also includes entries for different profile parameters. Specifically, the lookup table can include several entries for each type of bodily structure, one entry for each profile parameter. As a representative and non-limiting example, a look-up table can include several entries for, say, trabecular bone structure, wherein one entry for each age group.

In some embodiments of the present invention the set of AM rules are selected by the operator, for example, via a user interface (e.g., user interface 116). Also contemplated, are embodiments in which both a look-up table and a user interface are employed. For example, the look-up table can be used for narrowing the number of options provided to the operator, and the user interface can be used for selecting the final set of AM rules.

Further contemplated, are embodiments in which the set of rules are received together with the computer object data. For example, each computer object data file can include one or more AM rules, or be associated with AM rule file including one or more AM rules, wherein the AM rules correspond to the respective computer object data.

At 705 a slicing operation is applied, optionally and preferably separately for each computer object data file. The slicing is typically executed by generating, for computer object data file, a set of image files, each describing a 2D voxel map of a plane characterized by a different vertical coordinate (e.g., the aforementioned z coordinate), which plane corresponds to a layer of the object mimicking the respective bodily structure. The image file can be in any 2D format known in the art, such as, but not limited to, a bitmap file (BMP), portable network graphs (PNG), or the like. A preferred slicing technique is provided below with reference to FIG. 7B.

At 706 two or more of the sets of image files are combined into a single image file. For example, image files that correspond to the same vertical coordinate but to objects mimicking different bodily structures can be combined to provide an image file that describe a layer which, once printed, includes sliced sections of two or more objects respectively mimicking two or more bodily structures. At 707 the image file(s) is uploaded to an AM system such as, but not limited to, system 10 or system 110, to fabricate non-biological objects that resembles the bodily structures.

The procedure ends at 708.

Figure 7B:
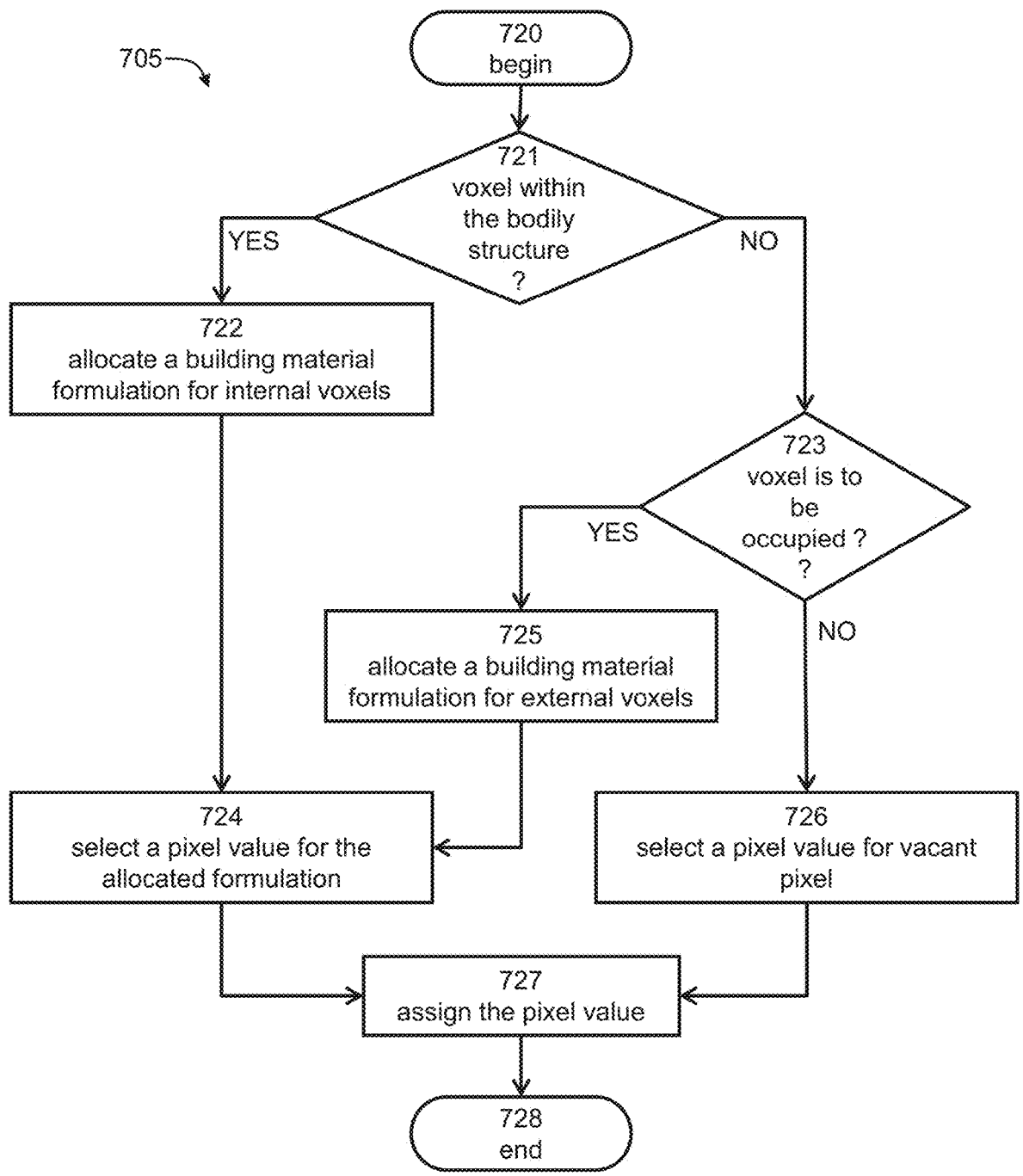

FIG. 7B is a flowchart diagram of an exemplified slicing method according to some embodiments of the present invention. The method is particularly useful for executing slicing operation 705 of FIG. 7A. The method begins at 720 and is optionally and preferably applied for each voxel in the computer object data.

At decision 721 a distance field value relative to the 3D object is determined for the respective voxel. The distance field value indicates whether the voxel is within or outside the object mimicking the bodily structure to be printed. For example, negative distance field values can be assigned to voxels outside the object mimicking the bodily structure, positive distance field values can be assigned to voxels within the object mimicking the bodily structure, and zero distance field values can be assigned to voxels on the outermost surface of the object mimicking the bodily structure. A representative example of a technique suitable for determining distance field values is provided in example 5, below.

When the voxel is within or on the outermost surface of the object mimicking the bodily structure (for example, when the distance field value is positive), the method continues to 722 at which a building material formulation is allocated for the respective voxel. The building material formulation can be a modeling material formulation, a support material formulation, or a liquid material formulation, and is optionally and preferably determined based on the position of the voxel in the 3D object and the AM rules obtained at 704 above. From 722 the method continues to 724 at which the method selects a pixel value that corresponds to the allocated building material formulation. The pixel value can be any value that uniquely represents the allocated building material formulation. For example, the pixel value can be a grayscale level or a color value (e.g., RGB value).

When the voxel is outside the object mimicking the bodily structure (for example, when the distance field value is negative), the method continues to decision 723 at which the method determine whether the voxel is to be occupied or left vacant. If the voxel is to be left vacant, the method continues to terminal 726, the method selects a pixel value that uniquely represents a vacant pixel. For example, the method can select a null value to represents a vacant pixel. Alternatively, when the voxel is outside the object mimicking the bodily structure the method can continues from 723 to terminal 728 where it ends, in which case pixels that have not been assigned with any values are to be interested as instructions to leave a voxel vacant.

If the voxel is to be occupied, the method continues to 725 at which a building material is allocated to the voxel, and then to 724 at which the method selects a pixel value that corresponds to the allocated building material formulation as further detailed hereinabove.

From 724, 725 or 726, as the case may be, the method continues to 727 at which the selected pixel value is assigned to a pixel in a 2D image, wherein the location of the pixel in the 2D image corresponds to the location of the voxel within the layer that is represented by the 2D image.

The method ends at 728.

Herein throughout, the term "bodily" when used in the context of, for example, a structure, organ, tissue or material, describes the indicated structure, organ, tissue or material, as being part of a body of a subject, preferably a living subject. This term encompasses biological systems, organs, tissues, cells and materials.

Herein throughout, the term "subject" encompasses animals, preferably mammals, more preferably human beings, at any age. This term encompasses individuals who are at risk to develop the pathology or who suffer from a pathology.

The term "bodily structure" refers to a part of a body of a subject, as described herein, including systems, organs, tissues, cells and a surrounding environment of any of the foregoing. A bodily structure, for example, can comprise several organs acting together in a living body, for example, a gastrointestinal tract, a cardiovascular system, a respiratory tract, and the like. The structure can include, in addition to organs and tissues that form a part of these systems, also structures related to a pathology, for example, tumor cells or tissues. A bodily structure can alternatively include, for example, a heart and blood vessels associated therewith. A bodily structure can alternatively include an organ, such as, for example, an arm or forearm, or leg, and can encompass the related bones system and muscle tissues, blood vessels, tumor tissues (if present) and/or skin tissues in its surroundings.

The term "tissue" describes a part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue, vascular tissue, renal tissue, pulmonary tissue, gonadal tissue, hematopoietic tis sue.

According to some of any of the embodiments described herein, at least some, and preferably all, the building material formulations usable in the context of the present embodiments are devoid of biological materials.

By "biological material", as used herein, it is meant organic materials that are inherently present in living subjects as defined herein. Such organic materials encompass, for example, cells and cellular components, proteins (including enzymes, hormones, receptor ligands and the like) peptides, nucleic acids, genes, amino acids.

By "devoid of" it is meant less than 1%, or less than 0.5%, or less than 0.1%, or less than 0.05%, or less than 0.01%, or less than 0.005%, or less than 0.001%, and less, including null, by weight, of the total weight of the object.

According to some of any of the embodiments described herein, the object is un-cellularized, namely, is devoid of biological cells or cellular components.

According to some of any of the embodiments described herein, at least some, and preferably all, the building material formulations usable in the context of the present embodiments are synthetic, non-biological, formulations, and are comprised essentially of synthetic materials.

As used herein, the term "synthetic material" describes an organic material that is not inherently present in a living subject. This term encompasses organic, non-biological materials, non-naturally occurring materials, and/or synthetically prepared materials.

According to some of any of the embodiments described herein, modeling material formulations as described herein comprise water in an amount of less than 10%, or less than 8%, or less than 5%, or even less, by weight, or is devoid of, as defined herein, water.

It is expected that during the life of a patent maturing from this application many relevant material formulations will be developed and the scope of the term material formulation is intended to include all such new technologies a priori, to the extent that these material formulations exhibit the mechanical properties described herein.

As used herein the term "about" refers to ±10% or ±5%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" or "process" refers to manners, means, techniques and procedures for accomplishing a given task including, but not limited to, those manners, means, techniques and procedures either known to, or readily developed from known manners, means, techniques and procedures by practitioners of the chemical, physical and engineering arts.

Herein throughout, the term "(meth)acrylic" encompasses acrylic and methacrylic compounds.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group" it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. The number of carbon atoms can range from 2 to 20, and is preferably lower, e.g., from 1 to 10, or from 1 to 6, or from 1 to 4. A hydrocarbon can be a linking group or an end group.

Bisphenol A is an example of a hydrocarbon comprised of 2 aryl groups and one alkyl group.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group or is or part of a linking moiety.

The term "alkyl" describes a saturated aliphatic hydrocarbon including straight chain and branched chain groups. Preferably, the alkyl group has 1 to 30, or 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Herein, a C(1-4) alkyl, substituted by a hydrophilic group, as defined herein, is included under the phrase "hydrophilic group" herein.

Alkene and Alkyne, as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

Cycloalkyls of 1-6 carbon atoms, substituted by two or more hydrophilic groups, as defined herein, is included under the phrase "hydrophilic group" herein.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholino, oxalidine, and the like.

The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

A heteroalicyclic group which includes one or more of electron-donating atoms such as nitrogen and oxygen, and in which a numeral ratio of carbon atoms to heteroatoms is 5:1 or lower, is included under the phrase "hydrophilic group" herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein. The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)— linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "isocyanate" describes an —N=C=O group.

The term "isothiocyanate" describes an —N=C=S group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carboxylate" as used herein encompasses C-carboxylate and O-carboxylate. The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S) NR'— end group or a —OC(=S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N— dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S) NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

An amide can be linear or cyclic. When cyclic, R' and the carbon atom are linked together to form a ring, in C-amide, and this group is also referred to as lactam. Cyclic amides can function as a linking group, for example, when an atom in the formed ring is linked to another group.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R"' end group or a —R'NC(=N)—NR"— linking group, as these phrases are defined hereinabove, where R', R" and R"' are as defined herein.

The term "hydrazine" describes a —NR'—NR"R"' end group or a —NR'—NR"— linking group, as these phrases are defined hereinabove, with R', R", and R"' as defined herein.

As used herein, the term "hydrazide" describes a —C(=O)—NR'—NR"R"' end group or a —C(=O)—NR'—NR"— linking group, as these phrases are defined hereinabove, where R', R" and R"' are as defined herein.

As used herein, the term "thiohydrazide" describes a —C(=S)—NR'—NR"R"' end group or a —C(=S)—NR'—NR"— linking group, as these phrases are defined hereinabove, where R', R" and R"' are as defined herein.

As used herein, the term "alkylene glycol" describes a —O—[(CR'R")$_z$—O]$_y$—R"' end group or a —O—[(CR'R")$_z$—O]$_y$— linking group, with R', R" and R"' being as defined herein, and with z being an integer of from 1 to 10, preferably, from 2 to 6, more preferably 2 or 3, and y being an integer of 1 or more. Preferably R' and R" are both hydrogen. When z is 2 and y is 1, this group is ethylene glycol. When z is 3 and y is 1, this group is propylene glycol. When y is 2-4, the alkylene glycol is referred to herein as oligo(alkylene glycol).

When y is greater than 4, the alkylene glycol is referred to herein as poly(alkylene glycol). In some embodiments of the present invention, a poly(alkylene glycol) group or moiety can have from 10 to 200 repeating alkylene glycol units, such that z is 10 to 200, preferably 10-100, more preferably 10-50.

The term "silanol" describes a —Si(OH)R'R" group, or —Si(OH)$_2$R' group or —Si(OH)$_3$ group, with R' and R" as described herein.

The term "silyl" describes a —SiR'R"R"' group, with R', R" and R"' as described herein.

As used herein, the term "urethane" or "urethane moiety" or "urethane group" describes a Rx-O—C(=O)—NR'R" end group or a —Rx-O—C(=O)—NR'— linking group, with R' and R" being as defined herein, and Rx being an alkyl, cycloalkyl, aryl, alkylene glycol or any combination thereof. Preferably R' and R" are both hydrogen.

The term "polyurethane" or "oligourethane" describes a moiety that comprises at least one urethane group as described herein in the repeating backbone units thereof, or at least one urethane bond, —O—C(=O)—NR'—, in the repeating backbone units thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Soft Material Formulation

The building material formulations usable in the additive manufacturing process described herein in any of the respective embodiments comprises, in some embodiments, at least one modeling material formulation which features (exhibits, characterized by), when hardened, a Shore A hardness lower than 10 or a Shore 00 hardness lower than 40. Such a formulation is also referred to herein as "soft material formulation" or "soft material modeling formulation" or "soft modeling formulation".

Herein and in the art, the term "hardness" describes a resistance of a material to permanent indentation, when measured under the specified conditions. Shore A hardness, which also referred to as Hardness ShA or as Shore scale A hardness, for example, is determined following the ASTM D2240 standard using a digital Shore A hardness durometer. Shore 00 hardness, which also referred to as Hardness Sh00 or as Shore scale 00 hardness, for example, is determined following the ASTM D2240 standard using a digital Shore 00 hardness durometer. D, A and 00 are common scales of hardness values, and each is measured using a respective durometer.

In some of any of the embodiments described herein, a soft material formulation as described herein features, when hardened, Shore A hardness in a range of from 0 to about 10, including any intermediate values and subranges therebetween.

In some of any of the embodiments described herein, a soft material formulation as described herein features, when hardened, Shore 00 hardness in a range of from 0 to about 40, or from 0 to about 30, or from 0 to about 20, or, for example, of from about 10 to about 20, or from about 10 to about 30, including any intermediate values and subranges therebetween.

Another parameter demonstrating the low hardness of a soft material obtainable for a hardened soft material formulation as described herein is the compression modulus.

By "Compression Modulus" it is meant herein the ratio of mechanical stress to strain in a material when that material is being compressed. Compression modulus can also be regarded as a modulus of elasticity applied to a material under compression. In some embodiments, compression modulus is determined according to ASTM D695. In some embodiments, compression modulus is determined for a cylindrical uncoated object (printed of a tested soft formulation per se) featuring a radius of 20 mm and a height of 15 mm, printed using Stratasys J750™ 3D Printer. The test is performed using a Lloyd instrumental system, 100N load cell, operated at the following parameters: Direction=Compression; Preload/Stress=0.5 N; preload/Stress Speed=50 mm/minute; Speed=50 mm/minute; Limit=8 mm. A stress vs. strain data is extracted from the obtained data and the slope between strain values of 0.001-0.01 was calculated. The data obtained in these tests can be expressed as compression stress at 40% strain, or as the slope of a stress vs. strain curve, when measured in a compression mode, taken at strain values of from 0.001 to 0.01.

Same Lloyd system can be used in adhesion tests, operated at the following parameters: Direction=Tension; Speed down=2 mm/minute; Speed up=5 mm/minute; Force down=−5N; Holding time=1 second. Specimens in which a tested soft formulation is used as a coat are measured, and results are reported as the maximum load required to pull out the platen from the coat specimen.

Compression modulus can alternatively be determined, for example, for a cylindrical, Agilus30-coated object made of the tested soft formulation, featuring a radius of 20 mm and a height of 15 mm, printed using Stratasys J750™ 3D Printer. The test is performed using a Lloyd instrumental system, 100N load cell, operated at the following parameters: Direction=Compression; Preload/Stress=0.5 N; preload/Stress Speed=50 mm/minute; Speed=50 mm/minute; Limit=90N. The compression modulus is determined for a maximum stress value of 90N. A stress vs. strain data can be extracted from the obtained data and the slope between strain values of 0.001-0.01 was calculated.

In some of any of the embodiments described herein, a soft material formulation as described herein features, when hardened, Compression Modulus of at least 0.01 MPa.

In some embodiments, a soft material formulation as described herein features, when hardened, Compression Modulus (as defined herein) of from about 0.01 to about 0.2 MPa, or from about 0.02 to about 0.2 MPa, from about 0.1 to about 0.1 MPa, or from about 0.02 to about 0.1 MPa, or from about 0.03 to about 0.07 MPa, including any intermediate value and subranges therebetween.

In some embodiments, a soft material formulation as described herein features, when hardened, in addition to its low hardness, at least a moderate Tear resistance.

Tear Resistance (TR) describes the force required to tear a material, whereby the force acts substantially parallel to the major axis of the sample. Tear Resistance, when measured according to ASTM D 624 can be used to measure the resistance to the formation of a tear (tear initiation) and the resistance to the expansion of a tear (tear propagation). Typically, a sample is held between two holders and a uniform pulling force is applied until deformation occurs. Tear Resistance is then calculated by dividing the force applied by the thickness of the material. Materials with low Tear Resistance tend to have poor resistance to abrasion.

In some embodiments, the Tear resistance is determined in accordance with ASTM D624 for a specimen as described therein having a thickness of 2 mm. Values are reported as Load at maximum Load (N) for a 2 mm-thick specimen. Time to Break can also be measured in this test. The reported values can be converted to N/m Tear Resistance values when divided by 0.002. For example, a value of 0.3N equals 150 N/m.

Load to break can be determined for a cubic Agilus-coated object made of the tested formulation, having dimensions of 50×50×50 mm, printed using Stratasys J750™ 3D Printer. The test is performed using a Lloyd instrumental system, 100N load cell, operated at the following parameters: Direction=Compression; Preload/Stress=0.5 N; preload/Stress Speed=50 mm/minute; Speed=50 mm/minute; load to break is determined as the maximum load the sample can hold before ultimate failure.

In some of any of the embodiments described herein, a soft material formulation described herein features, when hardened, Tear resistance of at least 100 N/m, as determined by ASTM D 624 for a specimen having a thickness of 2 mm.

In some embodiments, a soft material formulation described herein features, when hardened, Tear resistance, as determined by ASTM D 624 for a specimen having a thickness of 2 mm, of at least 150 N, and in some embodiments, it features Tear resistance of from 150 N/m to 500 Nm, or from 150 to 400 N/m, or from 200 N/m to 400 N/m, or from 200 N/m to 350 N/m, including any intermediate values and subranges therebetween.

In some embodiments, Tear Resistance measurements are used to determine also the time to break of a specimen under the applied pulling force.

In some embodiments, a soft material formulation as described herein features, when hardened, a time to break, as measured by ASTM D 624 for a specimen having a thickness of 2 mm, of at least 9 seconds, for example, from 9 to 50, or from 9 to 40 or from 9 to 30, or from 15 to 30 seconds.

In some of any of the embodiments described herein, a soft modeling formulation as described herein is characterized by good reactivity, that is, the dispensed layers comprising the formulation are hardened when exposed to a curing condition within a time period of less than 1 second, and/or a hardened layer made of the soft modeling formulation exhibits good adhesion (e.g., as demonstrated in the following).

In some embodiments, a soft modeling formulation as described herein is characterized by a liquid to solid transition within 1 second upon exposure to a curing condition. In some of these embodiments, the curing condition is UV irradiation, for example, UV irradiation at 1 W/cm$^2$. In some embodiments, the UV irradiation is by a UV Mercury (Hg) arc lamp (Medium pressure, metal-halide). In some embodiments, a soft modeling formulation as described herein is characterized by a liquid to solid transition within 1 second upon exposure to a curing condition (e.g., UV irradiation at wavelength of from about 300 nm to about 450 nm and power density of about 1 W/cm$^2$, for example using a 250 W mercury arc lamp).

The time period required for liquid to solid transition can be determined using DSC measurements, as known in the art.

In some of any of the embodiments described herein, a soft modeling material formulation as described herein is characterized by good compatibility with the AM system, that is, it meets the system operation requirements (e.g., in terms of viscosity and viscosity stability, thermal stability, etc., as described hereinabove).

In some of any of the embodiments described herein, a soft modeling material formulation as described herein is characterized by good compatibility with an AM which is 3D inkjet printing, that is, it is jettbale, compatible with inkjet printing heads, and features a viscosity suitable for use with inkjet printing heads as described herein and a viscosity stability at 25-75° C., for at least 24, preferably at least 48, hours.

In some of any of the embodiments described herein, a soft modeling formulation as described herein is characterized by stability (shelf-life stability) of at least one month, or at least 2, 3, 4, 5 and even at least 6 months, that is, the formulations features substantially the same properties (e.g., any of the properties described herein) upon storage for the indicated time period.

In some of any of the embodiments described herein, a soft modeling formulation as described herein is characterized by stability (shelf-life stability) of at least one month, or at least 2, 3, 4, 5 and even at least 6 months, that is, the formulations features substantially the same appearance (e.g., color) upon storage (e.g., at room temperature) for the indicated time period.

Stability can be determined for uncoated objects (printed of a tested soft formulation per se) or for coated objects (printed with a 0.8 mm coating of an elastomeric curable material (for example, the Agilus family, e.g., Agilus30™), all printed using Stratasys J750™ 3D Printer, and featuring a cube shape of 25 mm×25 mm×25 mm, weighing the obtained object once printed, storing the object at 50° C. for 7 days, and re-weighing, using analytical scales, to provide the weight change in % wt., relative to the initial weight after printing.

Stability can also be measured for an Agilus-coated cubic object, printed of a tested formulation per se, using Stratasys J750™ 3D Printer, featuring 50 mm×50 mm×50 mm dimensions; weighing the obtained object once printed, storing the object at 50° C. for 3 days, and re-weighing, using analytical scales. The weight change is provided in % wt., relative to the initial weight after printing.

Stability was also measured in terms of color change over time, by observing color change after a period of 4 weeks at room temperature.

Dimensional stability can be determined, for example, for coated oval objects of 60×24×18 mm coated with 0.6 mm layer of an elastomeric curable material (for example, the Agilus family, e.g., Agilus30™), upon storage at 50° C. for several days or at room temperature for one month, and observing distortions in the object upon storage.

Stickiness after printing can be determined, for example, qualitatively, for a printed object shaped as a cube, by applying to the object a tissue paper and provide a rate on a 0-3 scale as follows: 3 for cases where the tissue paper could not be removed from the object, and 0 for cases where no fibers were stuck to the object once the tissue paper has been removed.

According to some of any of the embodiments described herein, the soft material formulation is a curable formulation and in some embodiments the formulation is curable by comprising materials that are polymerizable when exposed to a curing condition (e.g., curing energy), as described herein. It is noted that, as described in further detail hereinbelow, not all the materials in the curable formulation should be curable to render a formulation curable. Thus, herein throughout, and with respect to any formulation described herein, a formulation is defined as curable when at least one of the materials in the formulation is curable, or polymerizable, when exposed to a curing condition.

According to some of any of the embodiments described herein, the formulation is a synthetic, non-biological, formulation, and is comprised essentially of synthetic materials, as defined herein.

According to some of any of the embodiments described herein, the formulation comprises water in an amount of less than 10%, or less than 8%, or less than 5%, or even less, by weight, or is devoid of, as defined herein, water.

According to some of any of the embodiments described herein, the formulation is such that does not form a hydrogel when exposed to a curing condition.

As used herein and in the art, the term "hydrogel" describes a material comprising a three-dimensional fibrous network as a solid phase, and an aqueous solution encaged within the fibrous network. A hydrogel typically includes at least 80%, typically at least 85%, by weight, water.

Any formulation that features Shore hardness as indicated, preferably in combination with one or more, preferably all, of the other features described herein is contemplated in the additive manufacturing process described herein.

According to some embodiments of any of the embodiments described herein, a soft modeling material formulation comprises a combination of curable materials and non-curable polymeric material.

Herein, the phrase "non-curable" with respect to a material in the soft formulation means that the material does not solidify when exposed to a curing condition at which the curable materials solidify. A non-curable material can be a material that is devoid of polymerizable and/or cross-linkable groups, or can include polymerizable and/or cross-linkable groups yet polymerization and/or cross-linking is not effected when exposed to a curing condition at which the curable materials solidify.

In some embodiments, the non-curable material is devoid of polymerizable and/or cross-linkable groups.

Exemplary soft material formulations suitable for use in the context of the present embodiments, and which meet the process requirements, the object requirements (e.g., as featuring a hardness of a soft bodily tissue as described herein), and are compatible with an elastomeric curable formulation, are presented hereinafter.

Such soft modeling formulations are obtained by manipulating the type and amount of the non-curable material(s) and the type and amount of curable materials, such that properties such as printability, compatibility with other curable formulations, and mechanical performance of the printed object are provided.

According to some of any of the embodiments described herein, the soft modeling material formulation comprises curable materials and non-curable materials, and a total amount of the non-curable materials ranges from about 10 to about 49, or from about 10 to about 30, % by weight, of the total weight of the soft modeling formulation, including any intermediate values and subranges therebetween.

In some embodiments, a total amount of the non-curable polymeric materials ranges from 20 to 40, or from 25 to 40, % by weight, of the total weight of the soft modeling formulation, including any intermediate values and subranges therebetween.

According to some of any of the embodiments described herein, the soft modeling material formulation comprises curable materials and non-curable materials, and a ratio of the total amount of the curable materials and the amount of the non-curable polymeric material ranges from 4:1 to 1.1:1, or from 3:1 to 2:1, including any intermediate values and subranges therebetween.

According to some of any of the embodiments described herein, a total amount of the curable materials ranges from about 55 to about 70 weight percents, of the total weight of the soft modeling formulation, including any intermediate values and subranges therebetween.

According to some of any of the embodiments described herein, the curable materials comprise at least one mono-functional curable material and at least one multi-functional curable material.

According to some of any of the embodiments described herein, an amount of the mono-functional curable material ranges from about 50% to about 89% by weight of the total weight of the soft material formulation, including any intermediate values and subranges therebetween. According to some of any of the embodiments described herein, an amount of the multi-functional curable material ranges from about 1% to about 10% by weight of the total weight of the soft material formulation, including any intermediate values and subranges therebetween.

According to some of any of the embodiments described herein, a soft modeling material formulation as described herein comprises a mono-functional curable material, a multi-functional curable material and a non-curable polymeric material.

In some of any of the embodiments described herein, the formulation comprises more than 50%, by weight, of curable materials, that is, a total amount of the mono-functional and multi-functional curable materials is at least 51%, by weight, of the total weight of the formulation.

In some of any of the embodiments described herein, a total amount of the mono-functional and multi-functional curable materials ranges from 51% to 90% or to 89%, by weight, and in some embodiments, it ranges from 55% to 70%, by weight, of the total weight of the formulation, including any intermediate values and subranges therebetween.

In some of any of the embodiments described herein, a total amount of the mono-functional curable material(s) ranges from 50% to 60%, or from 55% to 60%, by weight, of the total weight of the formulation, including any intermediate value and subranges therebetween.

In some of any of the embodiments described herein, a total amount of the multi-functional curable material(s) ranges from 3% to 10%, or from 5% to 10%, or is, for example, 7%, by weight, of the total weight of the formulation, including any intermediate value and subranges therebetween.

In some of any of the embodiments described herein, a total amount of the non-curable material ranges from 10% to 49%, or from 20% to 45%, or from 25% to 40%, by weight, of the total weight of the formulation, including any intermediate value and subranges therebetween.

In some of any of the embodiments described herein, the formulation comprises:
  a mono-functional curable material, as described herein in any of the respective embodiments, in an amount of from 50 to 89 weight percents of the total weight of the formulation, including any intermediate value and subranges therebetween;
  a non-curable polymeric material, as described herein in any of the respective embodiments, in an amount ranging from 10 to 49 weight percents of the total weight of the formulation, including any intermediate value and subranges therebetween; and
  a multi-functional curable material, as described herein in any of the respective embodiments, in an amount ranging from 1 to 10 weight percents of the total weight of the formulation, including any intermediate value and subranges therebetween.

In some of any of the embodiments described herein, a ratio of the total amount of said mono-functional and said multi-functional curable materials and the amount of said non-curable polymeric material ranges from 4:1 to 1.1:1, or from 3:1 to 2:1, including any intermediate values and subranges therebetween.

In some of any of the embodiments described herein, the curable and/or non-curable materials comprised in the formulation are selected such that:
  (i) the non-curable polymeric material features a molecular weight of at least 1000, or at least 1500 or at least 2000 Daltons; and/or
  (ii) the non-curable polymeric material features a Tg lower than 0, or lower than −10, or lower than −20, ° C.; and/or
  (iii) at least 80 weight percents of the total amount of the mono-functional and the multi-functional curable materials include curable materials featuring, when hardened, a Tg lower than 0, or lower than −10, or lower than −20, ° C.

In some of any of the embodiments described herein, the curable and/or non-curable materials comprised in the formulation are selected such that:
  the non-curable polymeric material features a molecular weight of at least 1000, or at least 1500 or at least 2000 Daltons; and the non-curable polymeric material features a Tg lower than 0, or lower than −10, or lower than −20, ° C.; and/or
  at least 80 weight percents of the total amount of the mono-functional and the multi-functional curable materials include curable materials featuring, when hardened, a Tg lower than 0, or lower than −10, or lower than −20, ° C.

In some of any of the embodiments described herein, the curable and/or non-curable materials comprised in the formulation are selected such that at least 80 weight percents of the total amount of the mono-functional and the multi-functional curable materials include curable materials featuring, when hardened, a Tg lower than 0, or lower than −10, or lower than −20, ° C. In some such embodiments, at least 85%, or at least 90%, or at least 95%, or 100%, by weight, of the total weight of the mono-functional and multi-functional curable materials include curable materials featuring, when hardened, a Tg lower than 0, or lower than −10, or lower than −20, ° C.

In some of any of the embodiments described herein, the curable and/or non-curable materials comprised in the formulation are selected such that at least 80 weight percents of the total amount of the mono-functional and the multi-functional curable materials, as described herein, include curable materials featuring, when hardened, a Tg lower than −20° C.

In some of any of the embodiments described herein, the curable and/or non-curable materials comprised in the formulation are selected such that:
  the non-curable polymeric material features a molecular weight of at least 1000, or at least 1500 or at least 2000 Daltons, as described herein; and the non-curable polymeric material features a Tg lower than 0, or lower than −10, or lower than −20, ° C., as described herein; and at least 80 weight percents of the total amount of the mono-functional and the multi-functional curable materials, as described herein, include curable materials featuring, when hardened, a Tg lower than −20° C.

In some of any of the embodiments described herein, the curable and/or non-curable materials comprised in the formulation are selected such that:
  the non-curable polymeric material features a molecular weight of at least 2000 Daltons, as described herein; the non-curable polymeric material features a Tg lower than −20° C., as described herein; and at least 80 weight percents of the total amount of the mono-functional and the multi-functional curable materials, as described herein, include curable materials featuring, when hardened, a Tg lower than 0, or lower than −10, or lower than −20, ° C., as described herein.

Herein throughout, "Tg" refers to glass transition temperature defined as the location of the local maximum of the E" curve, where E" is the loss modulus of the material as a function of the temperature.

Broadly speaking, as the temperature is raised within a range of temperatures containing the Tg temperature, the state of a material, particularly a polymeric material, gradually changes from a glassy state into a rubbery state.

Herein, "Tg range" is a temperature range at which the E" value is at least half its value (e.g., can be up to its value) at the Tg temperature as defined above.

Without wishing to be bound to any particular theory, it is assumed that the state of a polymeric material gradually changes from the glassy state into the rubbery state within the Tg range as defined above. Herein, the term "Tg" refers to any temperature within the Tg range as defined herein.

Herein, the phrase "molecular weight", abbreviated as MW, when referring to a polymeric material, refers to the value known in the art as Mw, describing Weight Average Molecular Weight of the polymeric material.

Herein throughout, whenever the phrase "weight percents", or "% by weight" or "% wt.", is indicated in the context of embodiments of a modeling formulation, it is meant weight percents of the total weight of the respective uncured modeling formulation.

The Non-Curable Polymeric Material:

In some of any of the embodiments described herein, the non-curable material features a molecular weight of at least 500, or at least 1000, or at least 1500 or at least 2000 Daltons, for example, a molecular weight that ranges from 500 to 4000, or from 900 to 4000, preferably from 1000 to 4000, or from 1500 to 4000 or, more preferably from 2000 to 4000, or from 2500 to 4000, or from 1500 to 3500, Daltons, including any intermediate value and subranges therebetween.

In some of any of the embodiments described herein, the non-curable material features a Tg lower than 0, or lower than −10, or lower than −20, ° C., for example, a Tg in the range of from 0 to −40° C., or from −20 to −40° C., including any intermediate value and subranges therebetween.

In some of any of the embodiments described herein, the non-curable material features a molecular weight of at least 1000, or at least 1500 or at least 2000 Daltons, as described herein; and a Tg lower than 0, or lower than −10, or lower than −20, ° C., as described herein.

In some embodiments, the non-curable material features essentially the same properties (e.g., molecular weight and/or Tg) in the modeling material formulation and in the hardened (soft) material obtained upon curing.

As used herein, the term "polymeric" with reference to a material encompasses polymers and co-polymers, including block co-polymers.

Herein, the term "block co-polymer" describes a copolymer consisting of regularly or statistically alternating two or more different homopolymer blocks that differ in composition or structure. Each homopolymer block in a block copolymer represents polymerized monomers of one type.

Polymeric materials featuring the above-mentioned MW and/or Tg, include, for example, polymers or block copolymers that comprise one or more poly(alkylene glycol)s, as defined herein, including, for example, poly (ethylene glycol), poly(propylene glycol) and block co-polymers thereof (e.g., Pluronic® block copolymers).

In some of any of the embodiments described herein, the non-curable polymeric material comprises polypropylene glycol.

In some embodiments, the non-curable polymeric material is poly(propylene glycol), and in some embodiments it is a polypropylene glycol having a MW of about 2000 Daltons, or higher (e.g., 2000, 2200, 2400, 2500, 2600, 2800, or 3000, Daltons, or any intermediate value between these values, or of higher MW).

In some embodiments, the non-curable polymeric material is a block co-polymer that comprises at least one polypropylene glycol block.

In some embodiments, the non-curable polymeric material is a block co-polymer that comprises one or more polypropylene glycol block(s) and one or more polyethylene glycol block(s). Such block copolymer can be, for example, comprised of PEG-PPG-PEG, or of PEG-PPG, or of PEG-PPG-PEG-PPG, or of PPG-PEG-PPG, or of any other number of blocks, in any combination and in any order.

In some of these embodiments, a total amount of poly (ethylene glycol) in the block co-polymer is no more than 10 weight percents.

Thus, for example, in the exemplary block copolymers listed hereinabove, the length of the PEG blocks is such that the total amount of PEG is no more than 10% by weight. As representative, non-limiting example, a PEG-PPG-PEG block copolymer according to these embodiments comprises PEG (A % wt.)-PPG (B % wt.)-PEG (C % wt.), wherein A+C≤10 and B≥90, respectively, for example, A+C=10 and B=90, or wherein A+C=7 and B=93, or wherein A+C=5 and B=95. Similarly, a PPG-PEG-PPG block copolymer comprises PPG (A % wt.)-PEG (B % wt.)-PPG (C % wt.), wherein A+C≥90 and B≤10, respectively, for example, A+C=90 and B=10, or wherein A+C=93 and B=7, or wherein A+C=95 and B=5.

In some of any of the embodiments described herein, the block co-polymer has a MW of at least 2000 Daltons.

In some of any of the embodiments described herein for a PEG and PPG block copolymer, a ratio of the number of polypropylene glycol blocks and the number of polyethylene glycol blocks is at least 1.2:1, or at least 1.5:1 or at least 2:1. An exemplary such block copolymer is PPG-PEG-PPG. Another exemplary block copolymer is PPG-PEG-PPG-PEG-PPG.

Alternatively, or in addition, in some of any of the embodiments described herein for a PEG and PPG block copolymer, a ratio of the total number of polypropylene glycol backbone units and the total number of polyethylene glycol backbone units in the block copolymer is at least 2:1, or at least 3:1 or at least 4:1, or at least 5:1, or at least 6:1. An exemplary such block copolymer is PEG-PPG-PEG co-polymer, or PEG-PPG-PEG-PPG, or PEG-PPG-PEG-PPG-PEG, featuring such a ratio.

In some of any of the embodiments described herein, the non-curable material is characterized by low solubility (e.g., lower than 20% or lower than 10%, or lower), or insolubility, in water.

In the context of these embodiments, the phrase "water solubility" describes the weight % of a polymeric material that is added to 100 grams water before the solution becomes turbid (non-transparent).

In some of any of the embodiments described herein, the non-curable material is characterized by low miscibility (e.g., lower than 20% or lower than 10%, or lower), or is immiscible, in water.

The Mono-Functional Polymeric Material:

In some of any of the embodiments described herein, the mono-functional curable material features, when hardened, a Tg lower than −10, or lower than −20° C., for example, a Tg in the range of from 0 to −40° C., or from −20 to −40° C., including any intermediate value and subranges therebetween.

In some of any of the embodiments described herein, mono-functional curable materials usable in the context of the present embodiments can be represented by the Formula:

$$P\text{---}R$$

wherein P is a polymerizable group and R is a hydrocarbon, as described herein, optionally substituted by one or more substituents as described herein, and further optionally interrupted by one or more heteroatoms.

In some of any of the embodiments described herein, P is a photopolymerizable group, and in some embodiments, it is a UV-curable group, such that the curable material is photopolymerizable or is UV-curable. In some embodiments, P is an acrylic polymerizable group such as acrylate, methacrylate, acrylamide or methacrylamide, and such curable materials can be collectively represented by Formula A:

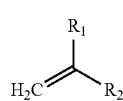

Formula A wherein at least one of $R_1$ and $R_2$ is and/or comprises a hydrocarbon, as described herein.

The ($=CH_2$) group in Formula I represents a polymerizable group, and is, according to some embodiments, a UV-curable group, such that the mono-functional curable material is a UV-curable material.

In some embodiments, $R_1$ is a carboxylate and $R_2$ is hydrogen, and the compound is a mono-functional acrylate. In some embodiments, $R_1$ is a carboxylate and $R_2$ is methyl, and the compound is mono-functional methacrylate. Curable materials in which $R_1$ is carboxylate and $R_2$ is hydrogen or methyl are collectively referred to herein as "(meth)acrylates".

In some of any of these embodiments, the carboxylate group is represented as —C($=$O)—ORa, and Ra is a hydrocarbon as described herein.

In some embodiments, $R_1$ is amide and $R_2$ is hydrogen, and the compound is a mono-functional acrylamide. In some embodiments, $R_1$ is amide and $R_2$ is methyl, and the compound is a mono-functional methacrylamide. Curable materials in which $R_1$ is amide and $R_2$ is hydrogen or methyl are collectively referred to herein as "(meth)acrylamide".

In some of any of these embodiments, the amide group is represented as —C($=$O)—NRbRa, and Ra and Rb are each independently selected from hydrogen and hydrocarbon, at least one being a hydrocarbon as described herein.

(Meth)acrylates and (meth)acrylamides are collectively referred to herein as (meth)acrylic materials.

When one or both of $R_1$ and $R_2$ comprise a polymeric or oligomeric moiety, the mono-functional curable compound of Formula A is an exemplary polymeric or oligomeric mono-functional curable material, respectively. Otherwise, it is an exemplary monomeric mono-functional curable material.

Generally, the chemical composition of the hydrocarbon (R is the P—R Formula, or Ra/Rb, if present, in Formula A) determines if the curable material, and the hardened material formed thereof, is hydrophilic, hydrophobic or amphiphilic.

As used herein throughout, the term "hydrophilic" describes a physical property of a material or a portion of a material (e.g., a chemical group in a compound) which accounts for transient formation of bond(s) with water molecules, typically through hydrogen bonding.

Hydrophilic materials dissolve more readily in water than in oil or other hydrophobic solvents. Hydrophilic materials can be determined by, for example, as having Log P lower than 0.5, when Log P is determined in octanol and water phases.

Hydrophilic materials can alternatively, or in addition, be determined as featuring a lipophilicity/hydrophilicity balance (HLB), according to the Davies method, of at least 10, or of at least 12.

As used herein throughout, the term "amphiphilic" describes a property of a material that combines both hydrophilicity, as described herein for hydrophilic materials, and hydrophobicity or lipophilicity, as defined herein for hydrophobic materials.

Amphiphilic materials typically comprise both hydrophilic groups as defined herein and hydrophobic groups, as defined herein, and are substantially soluble in both water and a water-immiscible solvent (oil).

Amphiphilic materials can be determined by, for example, as having Log P of 0.8 to 1.2, or of about 1, when Log P is determined in octanol and water phases.

Amphiphilic materials can alternatively, or in addition, be determined as featuring a lipophilicity/hydrophilicity balance (HLB), according to the Davies method, of 3 to 12, or 3 to 9.

A hydrophilic material or portion of a material (e.g., a chemical group in a compound) is one that is typically charge-polarized and capable of hydrogen bonding.

Amphiphilic materials typically comprise one or more hydrophilic groups (e.g., a charge-polarized group), in addition to hydrophobic groups.

Hydrophilic materials or groups, and amphiphilic materials, typically include one or more electron-donating heteroatoms which form strong hydrogen bonds with water molecules. Such heteroatoms include, but are not limited to, oxygen and nitrogen. Preferably, a ratio of the number of carbon atoms to a number of heteroatoms in a hydrophilic materials or groups is 10:1 or lower, and can be, for example, 8:1, more preferably 7:1, 6:1, 5:1 or 4:1, or lower. It is to be noted that hydrophilicity and amphiphilicity of materials and groups may result also from a ratio between hydrophobic and hydrophilic moieties in the material or chemical group, and does not depend solely on the above-indicated ratio.

A hydrophilic or amphiphilic material can have one or more hydrophilic groups or moieties. Hydrophilic groups are typically polar groups, comprising one or more electron-donating heteroatoms such as oxygen and nitrogen.

Exemplary hydrophilic groups include, but are not limited to, an electron-donating heteroatom, a carboxylate, a thiocarboxylate, oxo ($=$O), a linear amide, hydroxy, a (C1-4) alkoxy, an (C1-4)alcohol, a heteroalicyclic (e.g., having a ratio of carbon atoms to heteroatoms as defined herein), a cyclic carboxylate such as lactone, a cyclic amide such as lactam, a carbamate, a thiocarbamate, a cyanurate, an isocyanurate, a thiocyanurate, urea, thiourea, an alkylene glycol (e.g., ethylene glycol or propylene glycol), and a hydrophilic polymeric or oligomeric moiety, as these terms are defined hereinunder, and any combinations thereof (e.g., a hydrophilic group that comprises two or more of the indicated hydrophilic groups).

In some embodiments, the hydrophilic group is, or comprises, an electron donating heteroatom, a carboxylate, a heteroalicyclic, an alkylene glycol and/or a hydrophilic oligomeric moiety.

An amphiphilic moiety or group typically comprises one or more hydrophilic groups as described herein and one or more hydrophobic groups, or, can a heteroatom-containing group or moiety in which the ratio of number of carbon atoms to the number of heteroatoms accounts for amphiphilicity.

A hydrophilic or amphiphilic mono-functional curable material according to some embodiments of the present invention can be a hydrophilic acrylate represented by Formula A1:

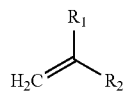

Formula A1 wherein $R_1$ and $R_2$ are as defined herein and at least one of $R_1$ and $R_2$ is and/or comprises a hydrophilic or amphiphilic moiety or group, as defined herein.

In some of any of these embodiments, the carboxylate group, —C(=O)—ORa, comprises Ra which is a hydrophilic or amphiphilic moiety or group, as defined herein. Exemplary Ra groups in the context of these embodiments include, but are not limited to, heteroalicyclic groups (having a ratio of 10:1 or 8:1 or 6:1 or 5:1 or lower of carbon atoms to electron-donating heteroatoms, such as morpholine, tetrahydrofurane, oxalidine, and the likes), hydroxyl, C(1-4)alkoxy, thiol, alkylene glycol or a hydrophilic or amphiphilic polymeric or oligomeric moiety, as described herein. An exemplary hydrophilic monomeric mono-functional acrylate is acryloyl morpholine (ACMO).

Exemplary hydrophilic or amphiphilic oligomeric mono-functional curable materials include, but are not limited to, a mono-(meth)acrylated urethane oligomer derivative of polyethylene glycol, a mono-(meth)acrylated polyol oligomer, a mono-(meth)acrylated oligomer having hydrophilic substituents, a mono-(meth)acrylated polyethylene glycol (e.g., methoxypolyethylene glycol), and a mono urethane acrylate.

In some embodiments, Ra in Formula A1 is or comprises a poly(alkylene glycol), as defined herein.

In some embodiments, Ra in Formula A1 comprises both an amphiphilic group or moiety and a hydrophobic group or moiety, as described herein. Such materials are referred to herein as amphiphilic curable materials that comprise a hydrophobic moiety or group.

As used herein throughout, the term "hydrophobic" describes a physical property of a material or a portion of a material (e.g., a chemical group or moiety in a compound) which accounts for lack of transient formation of bond(s) with water molecules, and thus for water-immiscibility, and is miscible or dissolvable in hydrocarbons.

A hydrophobic material or portion of a material (e.g., a chemical group or moiety in a compound) is one that is typically non-charged or non charge-polarized and does not tend to form hydrogen bonds.

Hydrophobic materials or groups typically include one or more of an alkyl, cycloalkyl, aryl, alkaryl, alkene, alkynyl, and the like, which are either un-substituted, or which, when substituted are substituted by one or more of alkyl, cycloalkyl, aryl, alkaryl, alkenyl, alkynyl, and the like, or by other substituents, such as electron-donating atom-containing substituents, yet a ratio of the number of carbon atoms to a number of heteroatoms in a hydrophobic materials or groups is at least 10:1, and can be, for example, 12:1, more preferably 15:1, 16:1, 18:1 or 20:1, or higher.

Hydrophobic materials dissolve more readily in oil than in water or other hydrophilic solvents. Hydrophobic materials can be determined by, for example, as having Log P higher than 1, when Log P is determined in octanol and water phases.

Hydrophobic materials can alternatively, or in addition, be determined as featuring a lipophilicity/hydrophilicity balance (HLB), according to the Davies method, lower than 9, preferably lower than 6.

A h hydrophobic material can have one or more hydrophobic groups or moieties that render the material hydrophobic. Such groups or moieties are typically non-polar groups, as described hereinabove.

In some embodiments, the hydrophobic group or moiety is, or comprises, a hydrocarbon, as defined herein, preferably of at least 6 atoms, such as an alkylene chain of, for example, at least 6 carbon atoms in length. When the hydrocarbon is substituted or interrupted by heteroatoms or heteroatom-containing groups, the above-indicated ratio between the number of carbon atoms and heteroatoms applies.

A hydrophobic mono-functional curable material according to some embodiments of the present invention can be a hydrophobic acrylate represented by Formula A2:

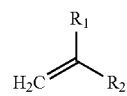

Formula A2 wherein $R_1$ and $R_2$ are as defined herein and at least one of $R_1$ and $R_2$ is and/or comprises a hydrophobic group or moiety, as defined herein.

In some of any of these embodiments, the carboxylate group, —C(=O)—ORa, comprises Ra which is a hydrophobic group, as defined herein. Exemplary hydrophobic monomeric mono-functional acrylates include isodecyl acrylate, lauryl acrylate, stearyl acrylate, linolenyl acrylate, bisphenyl acrylate and the like.

In some embodiments, Ra in Formula A2 is or comprises an alkylene chain of at least 6 carbon atoms in length, preferably unsubstituted.

In some of any of the embodiments described herein, the mono-functional curable material comprises a hydrophobic mono-functional curable material.

In some of these embodiments, the hydrophobic mono-functional curable material is a hydrophobic mono-functional acrylate, which is also referred to herein as "mono-functional acrylate type II".

In some of any of the embodiments described herein, the mono-functional curable material comprises a hydrophilic or amphiphilic mono-functional curable material.

In some of any of the embodiments described herein, the mono-functional curable material comprises an amphiphilic mono-functional curable material.

In some of these embodiments, the amphiphilic mono-functional curable material is an amphiphilic mono-functional acrylate which does not comprise a hydrophobic group as described herein, which is also referred to herein as "monofunctional acrylate type I".

In some of any of the embodiments described herein, the mono-functional curable material comprises an amphiphilic mono-functional curable material which comprises a hydrophobic moiety or group as described herein, which is also referred to herein as "monofunctional acrylate type II".

In some of any of the embodiments described herein, the mono-functional curable material comprises a combination of an amphiphilic mono-functional curable material and a hydrophobic mono-functional curable material (e.g., a combination of mono-functional acrylate of type I and a mono-functional acrylate of type II).

In some of these embodiments, a weight ratio of the amphiphilic mono-functional curable material and the hydrophobic mono-functional curable material can range from 2:1 to 1:2, and preferably ranges from 2:1 to 1:1 or from 1.5:1 to 1:1, or from 1.5:1 to 1.1:1, including any intermediate values and subranges between any of the forgoing.

In some of any of the embodiments described herein, the mono-functional curable material comprises a combination of a hydrophobic mono-functional acrylate and an amphiphilic mono-functional acrylate which comprises a hydrophobic group as described herein (e.g., a combination of two mono-functional acrylate of type II).

In some of these embodiments, a weight ratio of the amphiphilic mono-functional curable material and the hydrophobic mono-functional curable material can range from 2:1 to 1:2, and preferably ranges from 2:1 to 1:1 or from 1.5:1 to 1:1, or from 1.5:1 to 1.1:1, including any intermediate values and subranges between any of the forgoing.

In some of any of the embodiments described herein, the mono-functional curable material comprises an amphiphilic mono-functional acrylate which comprises a hydrophobic group as described herein (e.g., a mono-functional acrylate of type II).

In some of any of the embodiments described herein, the mono-functional curable material is such that features, when hardened, a Tg lower than 0° C., preferably lower than −10° C., or lower than −20° C., or lower, e.g., ranging from −20 to −70° C. In cases where the mono-functional curable material comprises a combination of two or more materials, at least one of these materials features, when hardened, a low Tg as described herein, and optionally and preferably, all of the materials feature such a Tg.

Further embodiments of mono-functional curable materials are described hereinbelow.

The Multi-Functional Curable Material:

As described herein, multi-functional curable materials are monomeric, oligomeric or polymeric curable materials featuring two or more polymerizable groups. Such materials are also referred to herein as cross-linking agents.

According to some of any of the embodiments described herein, the multi-functional curable material is a di-functional curable material. Such materials provide for a low degree of cross-linking and thereby provide for lower hardness of the hardened material.

According to some of any of the embodiments described herein, the multi-functional curable material features, when hardened, a Tg lower than −10, or lower than −20° C., and can be, for example, in a range of from −10 to −70° C.

Exemplary multi-functional curable material according to some embodiments of the present invention can be represented by Formula B:

Formula B

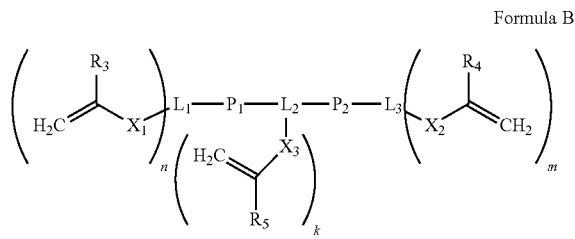

wherein:
each of $R_3$, $R_4$ and $R_5$ is independently hydrogen or a C(1-4)alkyl;
$L_1$ is a linking moiety, a branching unit or moiety (in case n is greater than 1) or absent;
$L_2$ is a linking moiety, a branching unit or moiety (in case k is other than 0) or is absent;
$L_3$ is a linking moiety, a branching unit or moiety (in case m is greater than 1) or absent;
each of $P_1$ and $P_2$ is independently a hydrocarbon, or an oligomeric or polymeric group or moiety, as these terms are defined herein, or absent;
each of $X_1$, $X_2$ and $X_3$ is independently a carboxylate, an amide, or absent; and
each of n, m and k is 0, 1, 2, 3 or 4,
provided that n+m+k is at least 2.

Multi-functional curable materials of Formula B in which one, two or all of $X_1$, $X_2$ and $X_3$, when present, is a carboxylate, are multi-functional acrylates. When one or more of $R_3$, $R_4$ and $R_5$, when present, is methyl, the curable materials are multi-functional methacrylates.

Multifunctional curable materials in which one, two or all of $X_1$, $X_2$ and $X_3$, when present, is carboxylate, can include a combination of acrylate and methacrylate functional moieties.

In some embodiments, the acrylate or methacrylate multifunctional curable material is monomeric, such that none of $P_1$ and $P_2$ is a polymeric or oligomeric moiety. In some of these embodiments, one or both of $P_1$ and $P_2$ is a hydrophilic or amphiphilic group as described herein, for example, an alkylene glycol, or any other hydrophilic or amphiphilic linking group, or is a short chain (e.g., of 1-6 carbon atoms), substituted or unsubstituted hydrocarbon moiety, as defined herein.

In some embodiments, one or both of $P_1$ and $P_2$ is a polymeric or oligomeric moiety as defined herein, and the curable compound is an oligomeric multi-functional curable material, for example, an oligomeric multi-functional acrylate or methacrylate, as described herein for $X_1$, $X_2$ and/or $X_3$. If both $P_1$ and $P_2$ are present, $L_2$ can be, for example, a linking moiety such as a hydrocarbon, comprising alkyl, cycloalkyl, aryl and any combination thereof. Exemplary such curable materials include ethoxylated or methoxylated polyethylene glycol diacrylate, and ethoxylated bisphenol A diacrylate.

Other non-limiting examples include polyethylene glycol diacrylate, polyethylene glycol dimethacrylate, polyethylene glycol-polyethylene glycol urethane diacrylate, an acrylated oligourethane, and a partially acrylated polyol oligomer.

In some embodiments, one or more of $P_1$ and $P_2$ is, or comprises, a poly(alkylene glycol) moiety, as defined herein.

Exemplary multi-functional acrylates are described in the Examples section that follows.

In some of any of the embodiments described herein, the mono-functional curable material(s) and the multi-functional curable material(s) are curable when exposed to the same curing condition.

In some embodiments, the mono-functional curable material(s) and the multi-functional curable material(s) are both photopolymerizable and in some embodiments are both UV-curable.

In some embodiments, the mono-functional curable material(s) and the multi-functional curable material(s) are both acrylic compounds, and in some embodiments are both (meth)acrylates or both are acrylates.

Initiators:

In some of any of the embodiments described herein, the soft modeling material formulation further comprises one or more agents which promote the polymerization of the curable materials, and are referred to herein as initiators.

In some of any of the embodiments described herein, the curable materials as described herein and an initiator form together a curable system. Such a system can further comprise an inhibitor, as described hereinafter.

It is to be noted that compounds/agents that form a part of a curable system, even if not curable by themselves, are not considered herein as non-curable materials, let alone non-curable polymeric materials as described herein.

In some of any of the embodiments described herein, a "curable system" comprises one or more curable materials and optionally one or more initiators and/or catalysts for initiating curing of the curable materials, and, further optionally, one or more conditions (also referred to herein as curing conditions) for inducing the curing, as described herein.

The one or more initiators are selected in accordance with the selected curable materials. Typically, initiators are further selected in accordance with the polymerization type of the curable materials. For example, a free radical initiator is selected for initiating free-radical polymerization (e.g., as in the case of acrylic curable materials); cationic initiator is selected for initiating cationic polymerization, and so forth. Further, photoinitiators are used in case one or more of the curable materials is photopolymerizable.

In some of any of the embodiments described herein, the curable system is a photocurable system, and the initiator is a photoinitiator.

In some embodiments, the curable system comprises acrylic compounds and the photoinitiator is a free-radical photoinitiator.

A free-radical photoinitiator may be any compound that produces a free radical on exposure to radiation such as ultraviolet or visible radiation and thereby initiates a polymerization reaction. Non-limiting examples of suitable photoinitiators include benzophenones (aromatic ketones) such as benzophenone, methyl benzophenone, Michler's ketone and xanthones; acylphosphine oxide type photo-initiators such as 2,4,6-trimethylbenzolydiphenyl phosphine oxide (TMPO), 2,4,6-trimethylbenzoylethoxyphenyl phosphine oxide (TEPO), and bisacylphosphine oxides (BAPO's); benzoins and bezoin alkyl ethers such as benzoin, benzoin methyl ether and benzoin isopropyl ether and the like. Examples of photoinitiators are alpha-amino ketone, and bisacylphosphine oxide (BAPO's). Further examples include photoinitiators of the Irgacure® family.

A free-radical photo-initiator may be used alone or in combination with a co-initiator. Co-initiators are used with initiators that need a second molecule to produce a radical that is active in the photocurable free-radical systems. Benzophenone is an example of a photoinitiator that requires a second molecule, such as an amine, to produce a free radical. After absorbing radiation, benzophenone reacts with a ternary amine by hydrogen abstraction, to generate an alpha-amino radical which initiates polymerization of acrylates. Non-limiting example of a class of co-initiators are alkanolamines such as triethylamine, methyldiethanolamine and triethanolamine.

In some of any of the embodiments described herein, the modeling material formulations comprises a free-radical curable system, and further comprises a radical inhibitor, for preventing or slowing down polymerization and/or curing prior to exposing to the curing condition.

In some of any of the embodiments described herein, the curable system polymerizable or cured via cationic polymerization, and are referred to herein also as cationic polymerizable or cationic curable systems.

In some embodiments, a cationic polymerizable material is polymerizable or curable by exposure to radiation. Systems comprising such a material can be referred to as photopolymerizable cationic systems, or photoactivatable cationic systems.

In some embodiments, a cationic curable system further comprises a cationic initiator, which produces cations for initiating the polymerization and/or curing.

In some embodiments, the initiator is a cationic photoinitiator, which produces cations when exposed to radiation.

Suitable cationic photoinitiators include, for example, compounds which form aprotic acids or Bronsted acids upon exposure to ultraviolet and/or visible light sufficient to initiate polymerization. The photoinitiator used may be a single compound, a mixture of two or more active compounds, or a combination of two or more different compounds, i.e. co-initiators. Non-limiting examples of suitable cationic photoinitiators include aryldiazonium salts, diaryliodonium salts, triarylsulphonium salts, triarylselenonium salts and the like. An exemplary cationic photoinitiator is a mixture of triarylsolfonium hexafluoroantimonate salts.

Non-limiting examples of suitable cationic photoinitiators include P-(octyloxyphenyl) phenyliodonium hexafluoroantimonate UVACURE 1600 from Cytec Company (USA), iodonium (4-methylphenyl)(4-(2-methylpropyl)phenyl)-hexafluorophosphate known as Irgacure 250 or Irgacure 270 available from Ciba Specialty Chemicals (Switzerland), mixed arylsulfonium hexafluoroantimonate salts known as UVI 6976 and 6992 available from Lambson Fine Chemicals (England), diaryliodonium hexafluoroantimonate known as PC 2506 available from Polyset Company (USA), (tolylcumyl) iodonium tetrakis (pentafluorophenyl) borate known as Rhodorsil® Photoinitiator 2074 available from Bluestar Silicones (USA), iodonium bis(4-dodecylphenyl)-(OC-6-11)-hexafluoro antimonate known as Tego PC 1466 from Evonik Industries AG (Germany).

In some of any of the embodiments described herein, an amount of an initiator (e.g., free-radical photoinitiator) ranges from 1 to 5, or from 1 to 3, weight percents, including any intermediate values and subranges therebetween. In exemplary embodiments, a combination of two or more initiators (e.g., photoinitiators) is used, and an amount of each ranges from 1 to 3, weight percents.

Additional Components:

According to some of any of the embodiments described herein, the soft modeling material formulation further comprises additional, non-curable components, such as, for example, inhibitors, surfactants, dispersants, colorants (coloring agents), stabilizers, and the like. Commonly used surfactants, dispersants, colorants and stabilizers are contemplated. Exemplary concentrations of each component, if present, range from about 0.01 to about 1, or from about 0.01 to about 0.5, or from about 0.01 to about 0.1, weight percents, of the total weight of the formulation containing same. Exemplary components are described hereinafter.

In some of any of the embodiments described herein, the formulation comprises a curing inhibitor, that is, an agent that inhibits or reduces an amount of the curing in the absence of a curing condition. In some embodiments, the inhibitor is a free radical polymerization inhibitor. In some embodiments, an amount of an inhibitor (e.g., a free radical inhibitor) ranges from 0.01 to 2, or from 1 to 2, or from 0.05 to 0.15, or is 0.1, weight percent, including any intermediate values and subranges therebetween, depending on the type of inhibitor used. Commonly used inhibitors, such as radical inhibitors, are contemplated.

In exemplary embodiments, a free radical inhibitor such as NPAL, or equivalents thereof, is used in an amount of from 0.01 to 1, or from 0.05 to 0.2, or from 0.05 to 0.15, or is 0.1, weight percent.

In alternative embodiments, a free radical inhibitor that is devoid of nitro or nitroso groups is employed. Exemplary such inhibitors are those of the Genorad™ family (e.g., Genorad18).

In exemplary embodiments, such a free radical inhibitor is used in an amount of from 0.1 to 3, or from 0.1 to 2, or from 0.5 to 2, or from 1 to 1.5, weight percents, including any intermediate values and subranges therebetween.

In exemplary embodiments, the soft modeling material formulation comprises a surfactant. Exemplary surfactants are those marketed as BYK surface additives. In some embodiments, the surfactant is a curable material, preferably curable upon exposure to the same curing condition as the curable materials in the formulation. In some embodiments, the surfactant is a UV-curable surfactant, and in some embodiments, the surfactant is a UV-curable BYK surfactant (e.g., BYK UV-3150 or BYK UV-3500).

In some embodiments, an amount of the surfactant in the formulation ranges from 0.1 to 1%, by weight, as described herein.

Exemplary Soft Modeling Formulations:

In some of any of the embodiments described herein, the soft modeling material formulation comprises non-curable polymeric material(s) as described herein, and an acrylic curable system which comprises a mono-functional acrylate (e.g., a combination of an amphiphilic and a hydrophobic mono-functional acrylate), a free-radical photoinitiator and optionally a free-radical inhibitor.

In some embodiments, the formulation further comprises one or more of the additional components as described herein.

In some embodiments, the formulation further comprises a coloring agent, as described herein, for example, such that provides a red tint, flesh-like color to the formulations, or a skin or skin pigmentation tint, to the formulations and objects or portions thereof made thereof. Exemplary flesh-like colors that are suitable for use with acrylic materials include, without limitation, those manufactured by Prosthetic Research Specialists, Inc. as "Flesh color system"; and color pigments marketed by Kingsley Mfg. Co.

In some embodiments, a concentration of the coloring depends on the intended use of the formulation and the desired visual properties of the object, and can range from 0.01 to 5, or from 0.01 to 1, or from 0.1 to 1, including any intermediate values and subranges therebetween.

In some of any of the embodiments described herein, the soft modeling material formulation comprises:
 a mono-functional amphiphilic acrylate, as described herein in any of the respective embodiments, in an amount of 25-35 weight percents;
 a mono-functional hydrophobic acrylate, as described herein in any of the respective embodiments, in an amount of 25-30 weight percents;
 a multi-functional acrylate, as described herein in any of the respective embodiments, in an amount of 5-10 weight percents; and
 a non-curable polymeric material featuring a molecular weight of at least 1000, or at least 1500 or at least 2000 Daltons; and a Tg lower than 0, or lower than −10, or lower than −20, ° C., as described herein in any of the respective embodiments, in an amount of 30-35 weight percents.

In some of these embodiments, the non-curable polymeric material comprises a polypropylene glycol and/or a block co-polymer comprising at least one polypropylene glycol block, each featuring a molecular weight of at least 2000 Daltons, as described herein in any of the respective embodiments.

In some of these embodiments, the multi-functional acrylate is a di-functional acrylate, and in some embodiments it is a urethane diacrylate.

In some of these embodiments, the mono-functional amphiphilic acrylate comprises a hydrocarbon chain of at least 6 carbon atoms and at least 2 alkylene glycol groups.

In some of these embodiments, the mono-functional hydrophobic acrylate comprises a hydrocarbon chain of at least 8 carbon atoms.

Exemplary formulations are presented hereinunder.

According to some of any of the embodiments described herein, the uncured building material comprises two or more soft modeling material formulations as described herein, each comprising a different combination of curable and non-curable materials according to the present embodiments, and optionally each feature, when hardened, a different Shore A hardness values in the range of 1-10 and/or different Shore 00 hardness values in the range of 0-40.

In some embodiments, such two of more building material formulations represent a formulation system of a soft modeling formulation.

Table 1.1 below presents exemplary formulations according to the present embodiments, which exhibit Shore scale A hardness 0 or Shore 00 hardness of from 0 to about 40, as described herein.

The phrase "monofunctional acrylate type I" as used in Table 1.1, encompasses monofunctional hydrophilic or hydrophilic amphiphilic acrylates, more specifically one or more monomeric, oligomeric or polymeric curable material(s) featuring an acrylate group as a polymerizable group and one or more heteroatoms (e.g., O, N or both) or heteroatom-containing groups (e.g., carboxylate, amide, alkylene glycol and combinations thereof) which impart a hydrophilic or amphiphilic nature. See also Formula A1 wherein $R_1$ is C(=O)—O—Ra, and Ra is a hydrophilic or amphiphilic moiety that does not include a hydrophobic group or moiety as described herein. Exemplary materials include alkoxy-terminated poly(ethylene glycol) acrylates (e.g., such as marketed as AM130); urethane acrylates (e.g., such as marketed as Genomer®, for example, Genomer 1122); Acryloyl morpholine, and any of the other respective curable materials described herein.

The phrase "monofunctional acrylate type II" encompasses one or more monomeric, oligomeric or polymeric, preferably monomeric, hydrophobic or hydrophobic amphiphilic, curable material(s) featuring an acrylate group as a polymerizable group and at least one hydrophobic moiety or group, e.g., a hydrocarbon of at least 6 carbon atoms in length, as defined herein. See also Formula A2 wherein $R_1$ is C(=O)—O—Ra, and Ra is or comprises a hydrophobic moiety or group.

Exemplary such materials include compounds of Formula A1 as described herein featuring as Ra groups such as nonyl phenyl, isodecyl, and/or lauryl groups, optionally in combination with alkylene glycol groups, for example, those marketed by Sartomer as SR395; SR504D, SR335, SR7095 and more.

The phrase "non-curable polymeric material" as used in the Examples section herein encompasses one or more polymeric material(s), preferably amphiphilic, devoid of a polymerizable acrylate group or any other polymerizable group that participates in polymerization upon exposure to conditions that initiate acrylate polyhmerization (e.g., devoid of photopolymerizable group or a group that polyhmerizes upon exposure to radiation at wavelength that induce acrylate polymerization). Preferably, the non-curable polymeric material(s) include one or more block co-polymers of PEG and PPG, also known under the Trade name "Pluronic®", at any order and number of blocks, at any MW and featuring a variety of Tg values when hardened. Preferably, the non-curable polymeric material(s) include one or more block co-polymers of PEG and PPG such as PEG-PPG-PEG and PPG-PEG-PPG, featuring no more than 10% by weight of PEG, and/or a PEG/PPG ratio as described herein, featuring MW of at least 500, preferably at least 900 and more preferably of at least 2,000, Daltons and/or featuring, when hardened, Tg lower than 20, preferably lower than 0, more preferably lower than −20, ° C. Preferably, these materials are characterized by low solubility (e.g., lower than 20% or lower than 10%, or lower), or insolubility in water.

The phrase "multi-functional acrylate" as used in the Examples section herein encompasses one or more monomeric, oligomeric or polymeric curable material(s) featuring two or more polymerizable acrylate groups. Such materials are also referred to herein as cross-linking agents. Exemplary such materials include, but are not limited to, urethane diacrylates such as, for example, marketed as Ebecryl 230; aliphatic di-, tri- or tetra-acrylates such as, for example, trimethylolpropane triacrylate, optionally ethoxylated (e.g., materials marketed as Photomer 4072, Photomer 4158, Photomer 4149, Photomer 4006, Miramer M360, SR499), glyceryl triacrylate, pentaerythritol tetraacrylate, optionally ethoxylated (e.g., marketed as Photomer 4172), heaxnediol diacrylate, PEGDA, and more; epoxy diacrylates such as marketed as Photomer 3005, Photomer 3015, Photomer 3016, Pgotomer 3316. Preferably, the multi-functional acrylate features, when hardened, Tg lower than 20° C., or lower than 0° C., or lower.

The phrase "polysiloxane" encompasses non-curable organic and inorganic materials comprising a polysiloxane backbone, including, as non-limiting examples, PDMS and derivatives thereof and block-copolymers containing same.

The terms "photoinitiator" and "inhibitor" are as defined herein.

All formulations presented in Table 1.1 comprise one or more photoinitiators in an amount ranging for 1 to 5% by weight (e.g., 3% wt.).

Exemplary photoinitiators include those of the Irgacure® family, for example, 1819, 1184, and a combination thereof.

All formulations presented in Table 1.1 comprise one or more inhibitors (free-radical polymerization inhibitors) in an amount ranging for 0.01 to 1% by weight (e.g., 0.1% wt.), unless otherwise indicated. Exemplary inhibitors include Tris(N-nitroso-N-phenylhydroxylamine) Aluminum Salt (NPAL) and inhibitors of the Genorad™ family, such as, for example, G18.

Some of the formulations presented in Table 1.1 further comprise additional, non-reactive components (additives) as described herein.

In an exemplary formulation (BM219) a UV-curable surface active agent is used—BYK UV-3500—Polyether-modified, acryl-functional polydimethylsiloxane.

TABLE 1.1

| Formulation Code | Monofunctional acrylate Type 1 (% wt.) | Monofunctional Acrylate Type II (% wt.) | Multi-functional acrylate* (% wt.) | Non-curable polymeric material (% wt.) |
|---|---|---|---|---|
| BM19 | X | 40 | 7 | 50$^a$ |
| BM19(5) | 5 | 40$^d$ | 7 | 45$^a$ |
| BM19(10) | 10 | 40$^d$ | 7 | 40$^a$ |
| BM29 | X | 52$^e$ | 15 | 30$^a$ |
| BM32 | X | 40$^f$ | 7 | 50$^a$ |
| BM35 | X | 50$^e$ | 7 | 40$^a$ |
| BM38 | 10 | 50$^e$ | 7 | 30$^a$ |
| BM43 | X | 57 (27$^e$ + 30$^d$) | 10 | 30$^a$ |
| BM44 | X | 57 (15$^e$ + 42$^d$) | 10 | 30$^a$ |
| BM58 | 20 | 30$^d$ | 7 | 40$^a$ |
| BM61 | X | 57 (27$^e$ + 30$^d$) | 7 | 33$^c$ |
| BM62 | X | 57 (27$^e$ + 30$^d$) | 7 | 33$^b$ |
| BM62 | X | 57 (27$^e$ + 30$^d$) | 7 | 33$^a$ |
| BM64 | 10 | 50$^f$ | 7 | 30$^c$ |
| BM66 | X | 57 (15$^d$ + 42$^e$) | 3 | 33$^c$ |
| BM67 | 20.9 | 31.3$^a$ | 3 | 41.8$^a$ |
| BM68 | 18.2 | 27.3$^a$ | 15 | 36.5$^a$ |
| BM75 | X | 94$^a$ | 3 | X |
| BM76 | X | 87$^a$ | 3 | 7$^c$ |
| BM77 | X | 79$^d$ | 3 | 15$^c$ |
| BM78 | X | 64$^d$ | 3 | 30$^c$ |
| BM101 | X | 61 (34$^a$+27$^e$) | 3** | 33$^c$ |
| BM102 | X | 61 (34$^d$ +27$^e$) | 3*** | 33$^c$ |
| BM103 | 27 | 33$^a$ | 7 | 30$^b$ |
| BM104 | 60 | X | 7 | 30$^b$ |
| BM108 | X | 57 (27$^e$ + 30$^d$) | 7 | 33$^h$ |
| BM109 | X | 67 (27$^e$ + 40$^d$) | 7 | 23$^c$ |
| BM110 | X | 47 (27$^e$ + 20$^d$) | 7 | 43$^c$ |
| BM111 | X | 67 (37$^e$ + 30$^d$) | 7 | 23$^c$ |
| BM112 | X | 62 (27$^e$ + 35$^d$) | 7 | 28$^c$ |
| BM131 | X | 57 (27$^e$ + 30$^d$) | 7 | 33$^g$ |
| BM151 | X | 57 (27$^e$ + 30$^d$) | 7 | 33 (16.5$^g$ + 16.5$^c$) |
| BM205.4$^\#$ | X | 56 (27$^e$ + 29$^a$) | 7 | 33$^k$ |
| BM219$^{\#\#}$ | X | 63$^f$ | 7 | 26 (13$^g$ + 13$^c$) |

$^a$= PPG; MW 900
$^b$= PEG-PPG-PEG block copolymer MW 2750
$^c$= PPG; MW 2000
$^h$= PPG-PEG-PPG block copolymer MW 3500
$^g$= PPG-PEG-PPG block copolymer MW 3250
$^k$= PEG-PPG-PEG block copolymer MW 2000
$^d$= ethoxylated nonylphenyl acrylate
$^e$= isodecyl acrylate
$^f$= lauryl acrylate or ethoxylated lauryl acrylate
*= urethane diacrylate (e.g., Ebecryl 230) unless otherwise indicated
**= aliphatic triacrylate (e.g., trimetholopropane triacrylate)
***= epoxy diacrylate (e.g., Photomer 3005F)
$^\#$= G18 type inhibitor used, at a concentration of 1.5% wt. + UV curable surface active agent (e.g., BYK3500)
$^{\#\#}$= G18 type inhibitor used, at a concentration of 1% wt.

Additional exemplary formulations, comprising a multi-functional acrylate other than urethane diacrylate and/or at an amount of from 1 to 3% wt., and/or comprising polysiloxane compounds at an amount of 5-10% wt., have been prepared, and all featured Shore A hardness 0.

Example 2

Liquid Material Formulation

A building material formulation that provides, upon exposure to a curing condition, a liquid or liquid-like material is also referred to herein as a liquid building material formulation or a liquid material formulation. In some embodiments, such a formulation is intended to remain liquid or form a liquid-like material upon being dispensed and exposed to a curing condition, as described herein.

Herein throughout and in the art, the term "liquid" describes a fluid that does not change its volume in response to stress. Liquid materials are characterized by fluidity, that is, the ability to flow as the molecules move by passing one by another; a viscosity, that is, a resistance to shear stress; by very low or zero shear modulus (G); and by a shear loss modulus to shear storage modulus ratio (G"/G', or tan delta) higher than 1, typically higher than 10.

Herein, a "liquid-like material" describes a gel-like or paste-like material that features properties similar to those of a liquid, by featuring, for example, a low shear modulus, e.g., lower than 100 kPa or lower than 50 kPa or lower than 10 kPa; and/or by a shear loss modulus to shear storage modulus ratio (tan δ) higher than 1, or by shear thinning behavior and hence its fluidity, viscosity and flowability resemble those of a liquid.

In some embodiments of the present invention, liquid and liquid-like materials feature one or more of the following characteristics:

a viscosity of no more than 10000 centipoises;
Shear loss modulus to Shear storage modulus ratio (tan delta) greater than 1;
Shear-thinning and/or thixotropic behavior;
Thermal-thinning behavior;
a Shear storage modulus lower than 20 kPa; and
flowability when subjected to a positive pressure lower than 1 bar or lower than 0.5 bar.

Shear storage modulus, G', is also referred to herein interchangeably as "storage shear modulus", and reflects an elastic behavior of a material. Liquid materials are typically non-elastic and hence feature a low shear storage modulus.

Shear loss modulus, G", is also referred to herein interchangeably as "loss shear modulus", and reflects a viscous behavior of a material.

Storage shear modulus and loss shear modulus may optionally be determined using a shear rheometer, for example, a strain-controlled rotational rheometer, at an indicated temperature and frequency (e.g., using procedures well known in the art).

The Shear loss modulus to Shear storage modulus ratio, G"/G', also known as "tan delta", reflects the viscoelastic behavior of a material. Liquid materials are typically more viscous and non-elastic and hence for liquids or liquid-like materials this ratio is higher than 1. Gels are typically elastic and hence this ratio for gel or gel-like materials is lower than 1.

Herein throughout, the term "shear-thinning" describes a property of a fluidic compound or a material that that is reflected by a decrease in its viscosity (increase in its fluidity) upon application of shear forces (under shear strain). In some of the present embodiments, a shear-thinning material is such that exhibits a significant, e.g., at least 100%, reduction in its Shear modulus upon increasing the shear strain from about 1% to above 50%.

Herein throughout, the term "thixotropic" describes a property of a fluidic compound or material that is reflected by a time-dependent shear-thinning, that is its viscosity is decreased in correlation with the time at which shear forces are applied, and returns back to its original value when application of shear forces is ceased. In some of the present embodiments, a thixotropic material is such that exhibits a significant, e.g., at least 100%, reduction in its Shear modulus under 50% strain.

Herein throughout, the term "thermal-thinning" describes a property of a fluidic compound or a material that is reflected by a decrease in its viscosity (increase in its fluidity) upon application of heat energy (increase in temperature). In some of the present embodiments, thermal-thinning materials feature a decrease in viscosity or shear modulus by at least 20%, or at least 50%, or even 100%, upon being heated to a temperature of from 40 to 95° C., including any intermediate value and subranges therebetween.

The liquid building material formulation can comprise one or more formulations, each comprising one or more non-curable materials in an amount of at least 50%, preferably at least 60%, or at least 70%, or at least 80%, or at least 90%, or 100%, by weight, of the total weight of the second building material formulation.

Because the liquid material formulation is comprised mainly of non-curable materials, when it is exposed to a curing condition, it undergoes minimal or essentially null hardening (e.g., no more than 20%, or no more than 10% by weight, of the material, hardens, e.g., polymerizes), thus maintaining essentially the same fluidity, or viscosity, as that of the dispensed formulation, such that the material obtained upon exposure to a curing condition is a liquid or liquid-like material, as defined herein.

In some of any of the embodiments described herein, one or more formulations in the liquid material building formulations are such that upon exposure to a curing condition provide a second material that features a viscosity of no more than 10,000 centipoises, or of no more than 1,000 centipoises, or of no more than 100 centipoises, for example, of 10-50 centipoises. In some of any of the embodiments described herein, the liquid building material formulation feature(s) a viscosity which is different from the viscosity of the second material by no more than 20%, preferably by no more than 10%. Thus, a change in the viscosity or the fluidity of the liquid building material formulation upon exposure to a curing condition is minimal (e.g., no more than 10%) or even null.

In some of any of the embodiments described herein for the liquid building material formulation, the non-curable material is or comprises a polymeric material and in some embodiments the polymeric material is or comprises one or more amphiphilic and/or hydrophilic polymer(s).

In some of any of the embodiments described herein for the liquid building material formulation, the non-curable material is or comprises a poly(alkylene glycol), as defined herein. The non-curable material can be a poly(alkylene glycol) per se or can comprise one or more poly(alkylene glycol) chains or blocks.

In some of any of the embodiments described herein, the non-curable material comprises a poly(alkylene glycol) having a molecular weight of less than 2000 grams/mol, and in some embodiments, the poly(alkylene glycol) is a polymer having a molecular weight of from 200 to 2000 or from 200 to 1000 or from 200 to 800 or from 200 to 600, or of 400, grams/mol.

In some of any of the embodiments described herein, the poly(alkylene glycol) is a poly(ethylene glycol). Alternatively, it is a poly(propylene glycol).

Other non-curable materials suitable for inclusion in the liquid building material formulation, instead of or in addition to a poly(alkylene glycol) as described herein, include, but are not limited to, block co-polymers comprising one or more poly(alkylene glycol) blocks, for example, block-co-polymers of poly(ethylene glycol) and poly(propylene glycol), such as those marketed under the trade name Pluronic®, polyols such as diols (e.g., propanediol), glycerols, and higher polyols.

Additional non-curable materials suitable for inclusion in the liquid formulation, include one or more oils, such as, but not limited to, one or more of a vegetable oil, a synthetic oil, a hydrocarbon oil, a silicone oil, a fatty acid, a mineral oil, and a paraffin oil. In some embodiments, the oil features a viscosity or any of the properties described herein as characterizing a liquid or liquid-like material.

In some of any of the embodiments described herein, the liquid building formulation further comprises water.

In some of any of the embodiments described herein, the liquid building formulation comprises a curable material, optionally in combination with a non-curable material, but is devoid of a catalyst or initiator that prompts the curing (e.g., polymerization) of the curable material. In such embodiments, the hardening of the liquid building formulation upon exposure to a curing condition is minimized or nullified, and the liquid or liquid-like material features fluidity properties that are similar to that of the liquid building formulation, as described herein.

In some of any of the embodiments described herein, the liquid material features a shear modulus of less than 20 kPa, or of less than 15 kPa, or of less than 10 kPa, or of less than 5 kPa, thus featuring a consistency of a very soft and flowable gel. Formulations providing such a material are also referred to herein as formulations that provide a liquid-like material.

In some of these embodiments, the liquid building material formulation comprises a curable material, optionally and preferably in combination with a non-curable material, as described herein in any of the respective embodiments.

According to some of these embodiments, the curable material is or comprises a mono-functional curable material, as defined herein.

Preferably, the curable material is in an amount of no more than 50%, preferably no more than 40%, or no more than 30%, or no more than 20%, and even of 15%, 10%, by weight, or less, of the total weight of the liquid material formulation. In some embodiments, an amount of the curable material in the liquid building material formulation ranges from 10 to 25 weight percents.

According to some of any of the embodiments described herein, the curable material is amphiphilic or hydrophilic (e.g., as described in Example 1 herein).

According to some of any of the embodiments described herein, the curable material is such that when hardened, it provides a water-soluble or water-miscible material, as defined herein.

According to some of any of the embodiments described herein, the curable material is such that when hardened, it provides a shear-thinning and/or thixotropic and/or thermal-thinning material, as defined herein.

Exemplary liquid building material formulations include formulations comprising a poly(alkylene glycol) as described herein, in an amount of at least 50% and up to 100%, by weight, optionally in combination with one or more curable materials as described herein, in a total amount of from 10 to 25% by weight, and further optionally in combination with additional components as described herein.

Generally, in some embodiments, the liquid building material formulation is selected such that the second (liquid) material is water-soluble or water-miscible, as defined herein.

Generally, in some embodiments, the liquid building material formulation is selected such that the second material is a shear-thinning material, as defined herein.

Generally, in some embodiments, the liquid building material formulation is selected such that the second material is a thixotropic material, as defined herein.

Generally, in some embodiments, the liquid building material formulation is selected such that the second material is a thermal-thinning material, as defined herein.

In some of any of the embodiments described herein, the uncured building material comprises two or more second building material formulations, as described herein, for example, one or more formulations which provide a liquid second material, featuring a viscosity which is substantially the same as that of the uncured formulation, as described herein, and comprising a non-curable material, and one or more formulations which provide a liquid-like material, featuring a shear stress of no more than 20 kPa, as described herein, and comprising curable and non-curable materials, as described herein.

In some of these embodiments, the dispensing is such that small hollow structures, featuring at least one dimension at the millimeter scale, as defined herein, are filled with a formulation that provides a liquid material, and larger hollow structures are filled with a formulation that provides a liquid-like material.

When the liquid building material formulation described in this example is dispensed, and straightened, the AM system, for example, by means of the controller, optionally and preferably ensures that the newly dispensed layer is in a still-air environment.

As used herein, "still-air environment" refers to an environment in which there is no air flow, or in which an air flows at speed less than 3 m/s.

Example 3

Characterization of Three-Dimensional Textured Objects

Several three-dimensional objects were printed with various combinations between material formulations. The material formulation used for forming the wall portions of the textured objects (see FIG. 5, wall portion 306) was "VeroPureWhite" (Stratasys Ltd., Israel), referred to in this example as and the material formulation used for forming the interior portions of the textured objects (see FIG. 5, interior portions 304) was "SUP706" (Stratasys Ltd., Israel).

FIGS. 25A-F are computer object data visualizations describing several combinations of material formulations used to investigate the effect of formulation ratio on the mechanical properties of the printed objects. FIGS. 25A-C correspond to a combination in which the interlaced locations are selected according to a Simplex modulating function, and FIGS. 25D-E correspond to a combination in which the interlaced locations are selected according to a Worley modulating function with a period of about 1 mm. The percentage of the area of a cell (see FIG. 5, cell 302) that was occupied by the wall portions (out of the total area of the cell) was about 0.5% (FIGS. 25A and 25D), about 0.6% (FIGS. 25B and 25E), and about 0.7% (FIGS. 25C and 25F). The cell size was about 1.25 mm. The effect of the percentage of the wall portion for these two modulating functions on the mechanical properties of the printed objects is summarized in Table 3.1, below.

TABLE 3.1

| Structure type | Rigid % | Cell size | E [MPa] | Yield Strength [MPa] |
|---|---|---|---|---|
| Simplex | 0.5 | 1.25 | 48 | 17 |
| | 0.6 | 1.25 | 170 | 26 |
| | 0.7 | 1.25 | 240 | >28 |

TABLE 3.1-continued

| Structure type | Rigid % | Cell size | E [MPa] | Yield Strength [MPa] |
|---|---|---|---|---|
| Worley 1 | 0.5 | 1.25 | 170 | 19 |
| | 0.6 | 1.25 | 240 | >28 |
| | 0.7 | 1.25 | 240 | >28 |

Figure 26D:
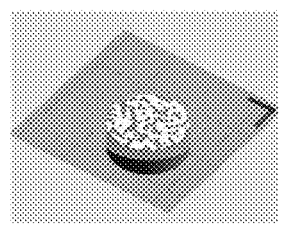

FIGS. 26A-D are computer object data visualizations describing several combinations of material formulations, used to investigate the effect of cell size on the mechanical properties of the printed objects. FIG. 26A corresponds to cell size of about 1 mm, FIG. 26B corresponds to cell size of about 1.5 mm, FIG. 26C corresponds to cell size of about 2 mm, and FIG. 26D corresponds to cell size of about 2.5 mm. The interlaced locations were selected according to a Perlin modulating function, and the percentage of the area of a cell that was occupied by the wall portions was about 0.5%. The effect of the cell size for this modulating function and this wall portion percentage on the mechanical properties of the printed objects is summarized in Table 3.2, below.

TABLE 3.2

| Structure type | Rigid % | Cell size | E [MPa] | Yield Strength [MPa] |
|---|---|---|---|---|
| Perlin | 0.5 | 1 | 40 | 5 |
| | 0.5 | 1.5 | 78 | 6 |
| | 0.5 | 2 | 86 | 8 |
| | 0.5 | 2.5 | 233 | >28 |

Figure 27A:
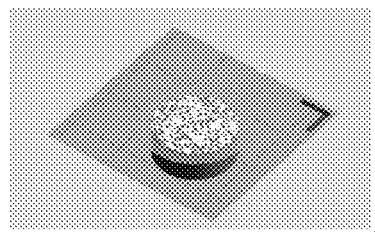
FIGS. 27A-27C are computer object data visualizations describing several combinations of material formulations used in experiments performed according to some embodiments of the present invention to investigate the effect of modulation function on the mechanical properties of three-dimensional printed objects.
Figure 27B:
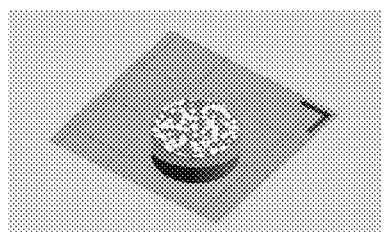
Figure 27C:
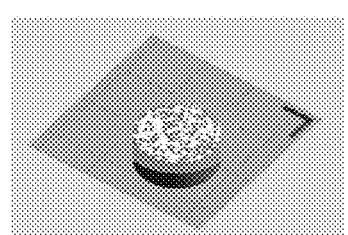

FIGS. 27A-C are computer object data visualizations describing several combinations of material formulations, used to investigate the effect of the modulation function on the mechanical properties of the printed objects. FIG. 27A corresponds to a combination in which the interlaced locations are selected according to a Simplex modulating function, FIG. 27B corresponds to a combination in which the interlaced locations are selected according to a Worley modulating function with a period of 1 mm, and FIG. 27C corresponds to a combination in which the interlaced locations are selected according to a Perlin modulating function. The percentage of the area of a cell that was occupied by the wall portions was about 0.5%, and the cell size was about 1.25 mm. The effect of the modulating function for this this wall portion percentage and this cell size on the mechanical properties of the printed objects is summarized in Table 3.3, below.

TABLE 3.3

| Structure type | Rigid % | Cell size | E [MPa] | Yield Strength [MPa] |
|---|---|---|---|---|
| Simplex | 0.5 | 1.25 | 48 | 17 |
| Worley 1 | 0.5 | 1.25 | 170 | 19 |
| Perlin | 0.5 | 1.25 | 59 | 5.5 |

This example demonstrates that by selecting AM parameters, including wall portion percentage, cell size and type of modulation, the mechanical properties of textured regions, can be controlled and adapted to the mechanical properties of trabecular bone tissue. For example, by increasing size of the cell, the stiffness and strength of the object is also increased.

Example 4

Exemplified Manufactured Objects

Figure 8A:
FIGS. 8A-8L are images (8A-8H and 8J-8L) and computer object data (FIG. 8I) of various shapes of objects according to some embodiments of the present invention.
Figure 8B:
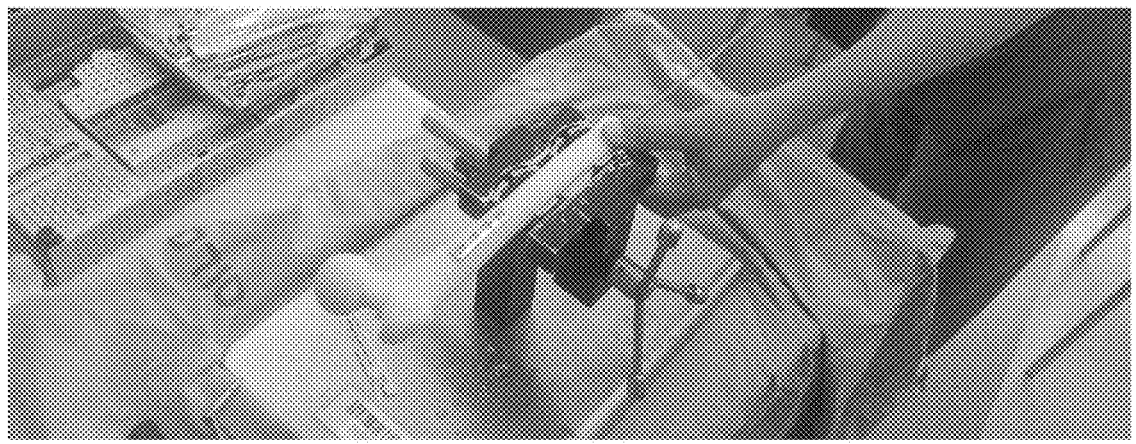
Figure 8C:
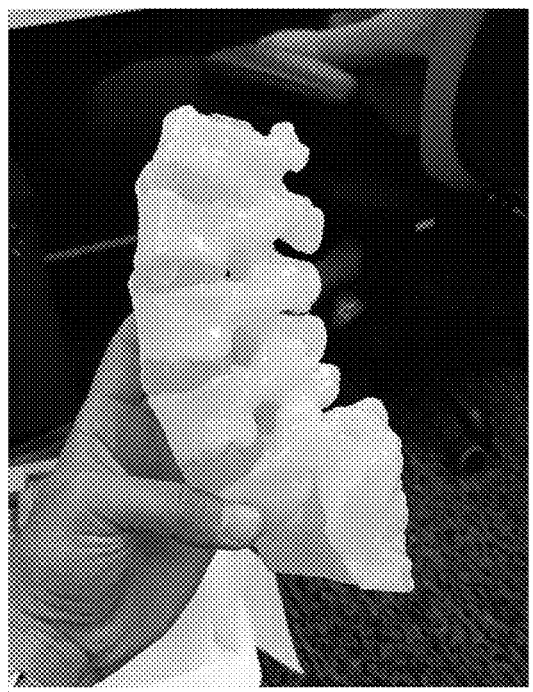
Figure 8D:
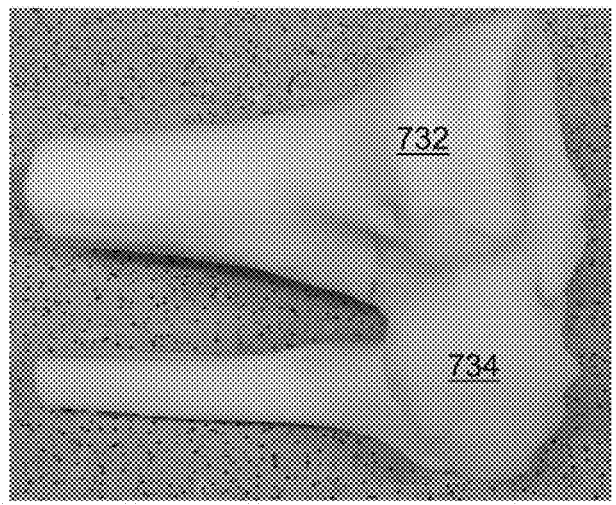
Figure 8E:
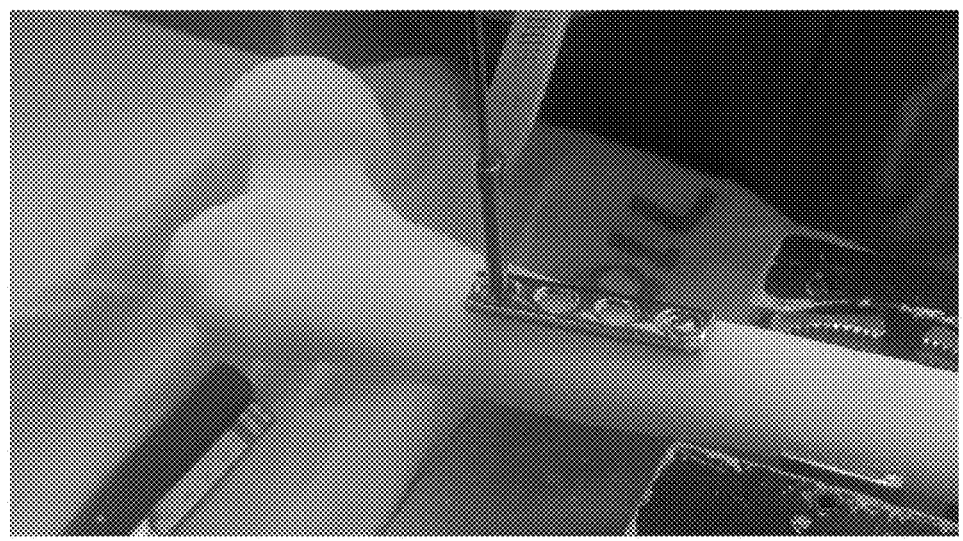
Figure 8F:
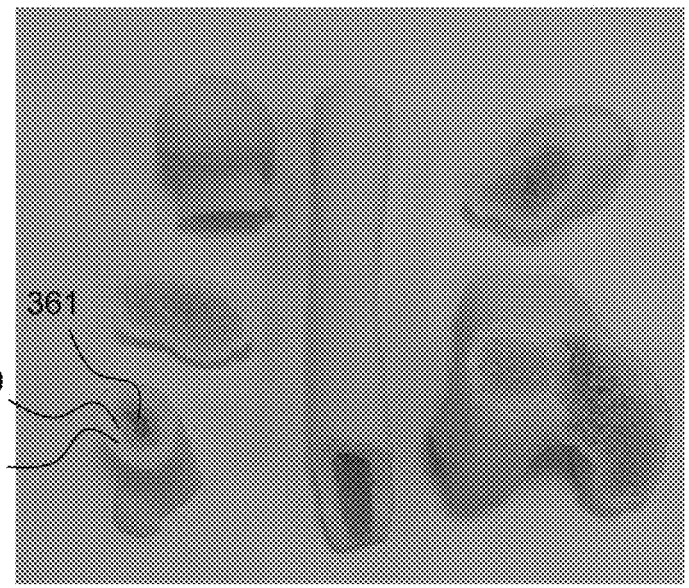
Figure 8G:
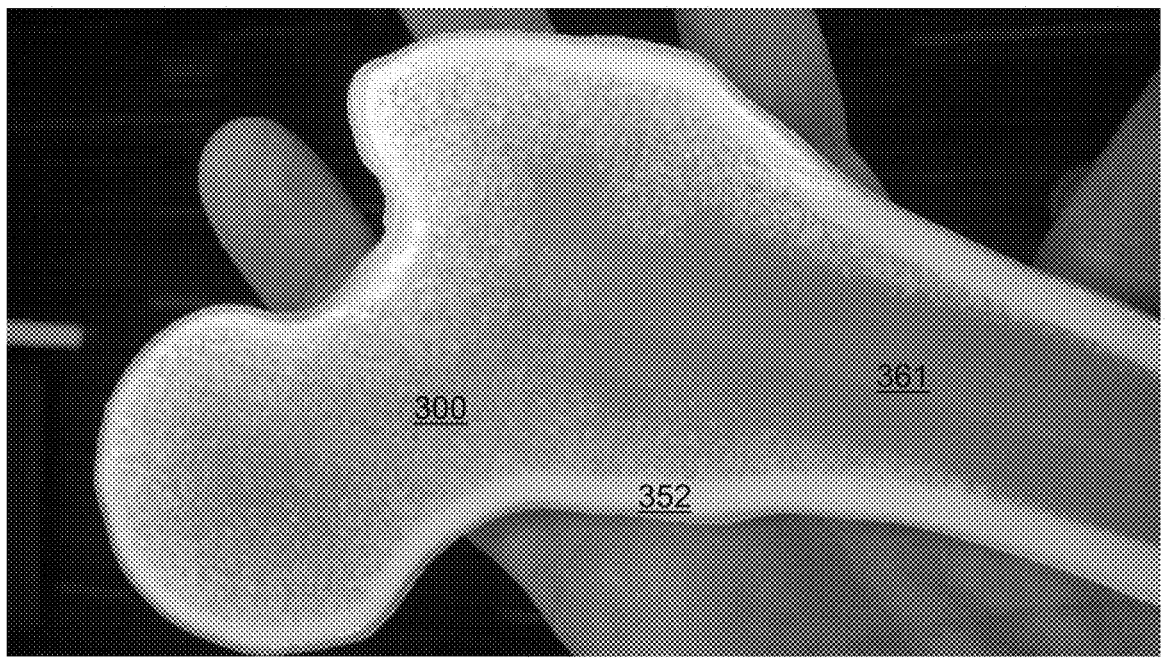
Figure 8H:
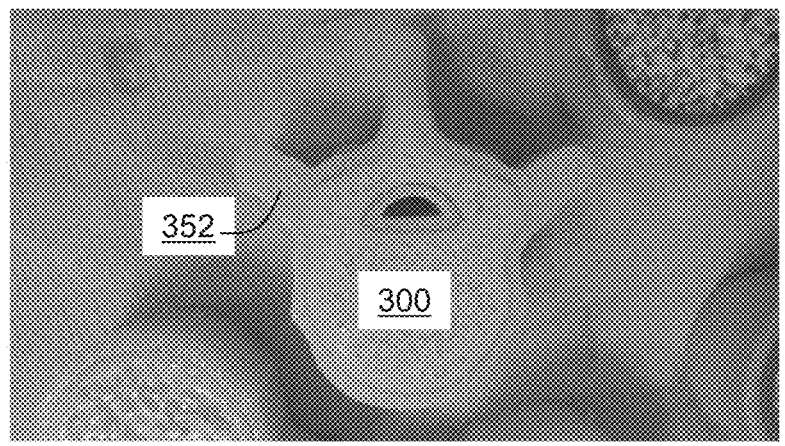
Figure 8I:
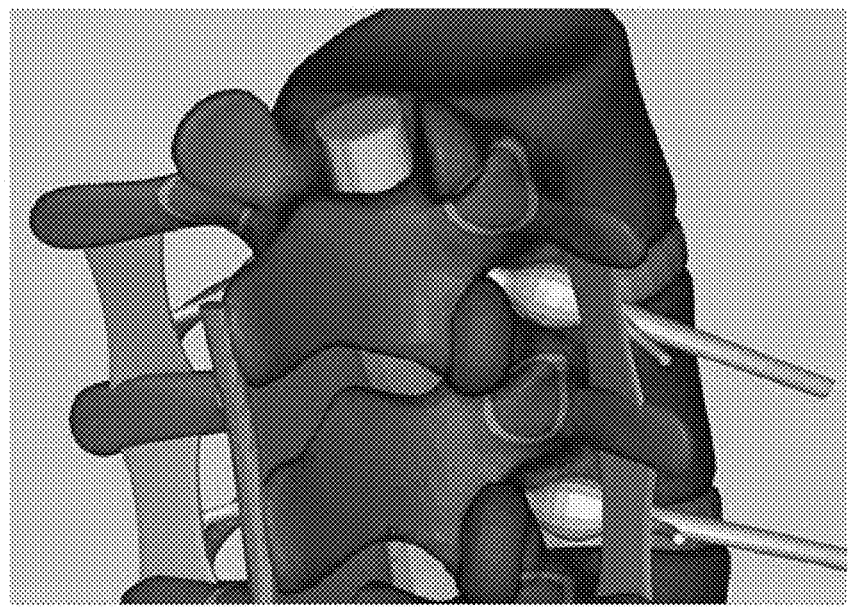
Figure 8J:
Figures 8K, 8L:
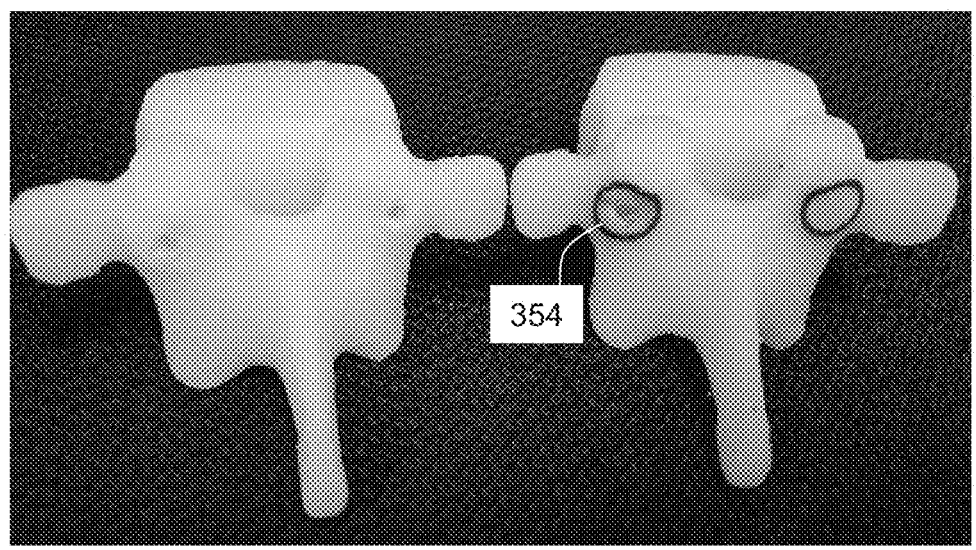

FIGS. 8A-H and 8J-L are images of various shapes of objects manufactured according to the teachings described herein. Specifically, FIG. 8A shows a long bone (femur, in this example), FIG. 8B shows a femur bone object during a screwing operation along a longitudinal direction through a flexible annulus structure (the annulus structure is not shown), FIG. 8C shows a spine section object, FIG. 8D shows a bone object 732 with a bone tumor structure 734, FIG. 8E shows a femur bone object during a screwing operation along a transverse direction through a flexible annulus structure (the annulus structure is not shown), FIG. 8F shows a cut bone object, demonstrating the core 361 mimicking the bone marrow, the textured region 300 mimicking the trabecular bone region, and the shell 352 mimicking cortical bone region, FIG. 8G shows a cross section of a longitudinal long bone object (femur object, in this example), also demonstrating the core 361 mimicking the bone marrow, the textured region 300 mimicking the trabecular bone region, and the shell 352 mimicking cortical bone region, FIG. 8H shows internal structures of a vertebra object demonstrating the textured region 300 mimicking the trabecular bone region and the shell 352 mimicking cortical bone region, FIG. 8J shows a vertebra object post screwing without annulus structure, showing a crack near screw hole, FIG. 8K shows another vertebra object post screwing and FIG. 8L shows an vertebra object post screwing with annulus structure demonstrating that the flexible annulus structure 354 ring halts spreading of cracks.

FIG. 8I is a representation of computer object data for AM of a spine including vertebra, disks, nerves and spinal cords, each shown in a different gray level for clarity of presentation.

Example 5

Distance Field and Modulation Functions

The present example describes a method that includes selecting a voxel from a three-dimensional build space and for the selected voxel, determining a distance field value relative to a three-dimensional part in the three-dimensional build space. The method can be used for preparing computer object data for use in systems 110 and 10 according to some embodiments of the present invention. At least some of the description below is also described in international patent application No. PCT/US2017/019340, filed on Feb. 24, 2017, the contents of which are hereby incorporated by reference.

The distance field value can be used to select at least one material selection rule and a feature of the voxel is applied to the at least one material selection rule to identify a material designation for the voxel. The material designation indicates no material is to be placed at the voxel when the material selection rule identifies no material for the voxel and the material designation indicates at least one material is to be placed at the voxel when the at least one material selection rule identifies the at least one material for the voxel. The material designation for the voxel is then output for use in building the three-dimensional part using an additive manufacturing system.

In some embodiments of the present invention the method includes selecting a voxel in a three-dimensional build space, determining a first distance field value for the voxel relative to a boundary of a first three-dimensional part positioned in the three-dimensional build space, and determining a second distance field value for the voxel relative to a boundary of a second three-dimensional part positioned in the three-dimensional build space. The first distance field value and the second distance field value are then used to set a material designation for the voxel.

To build a part using additive manufacturing, instructions must be provided to the printer to indicate what material, if any, should be placed in each of the available locations of each printing layer. In the past, these instructions were produced by identifying the exterior bounds of each part at each slice using boundary representations. A part material was then designated for each location that was positioned along the boundary of the part. If the part was to be solid, the material set for the part was also designated for each location within the boundaries of the part. In such systems, all material transitions, either from one material to another material, or from a material to open space, had to be described by a boundary representation.

The present inventors have discovered that relying on such boundary representations to control transitions between materials creates several problems. First, performing rounding, lofting and offset modeling operations where boundary representations are shifted inward or outward to produce the print instructions can produce errors or unexpected results due to interference between shifted boundary representations. This typically occurs when the topology of the part is complex. Second, Boolean operations, such as subtraction or union, which are performed between two different parts when generating print instructions, can fail if the boundary representations of the parts do not define an enclosed object. Any opening in the part will cause the Boolean operations to be limited to the boundary representation itself instead of the complete volume of the part. Third, it is extremely difficult to define lattices using boundary representations because the lattices require a huge number of meshes resulting in a large amount of data. Fourth, it is not possible to form material gradients in which a mixture of materials changes over some dimension of the part.

In the embodiments described below, the problems associated with boundary representations are overcome by using distance fields. In one embodiment, a distance field is created by dividing the three-dimensional build space, which contains the part(s) to be manufactured, into a three-dimensional matrix of voxels. The closest distance from each voxel to a part boundary is then determined such that if the voxel is within the part, the distance is set as a positive value, if the voxel is outside of the part, the distance is set as a negative value and if the voxel is on the part boundary, the distance is zero. This produces a three-dimensional matrix of distance field values. Each part has its own associated distance field. As a result, when there are multiple parts in the build space, each voxel has multiple different distance field values, each associated with a separated part.

Once the distance fields are determined, they are used to select at least one material selection rule for each voxel. Each material selection rule identifies a material designation for the voxel using at least one feature of the voxel such as the distance field value of the voxel and the position of the voxel in the build space, for example. In some embodiments, the material selection rule includes a periodic function that is a function of the distance field values and/or the position in the build space such that one range of output values produced by the periodic function is associated with no material being designated for the voxel and another range of output values produced by the periodic function is associated with a material being designated for the voxel. Such periodic functions allow lattices to be defined in the build space.

Figure 9:
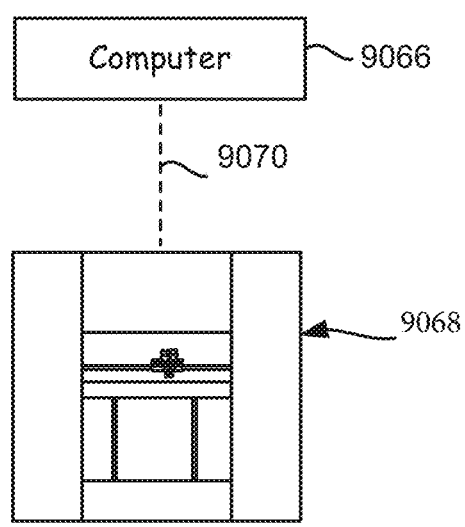
FIG. 9 is an example of a system for printing a 3D part using GPU material assignment based on distance fields.

FIG. 9 shows an example of a simplified system for assigning materials to voxels and manufacturing parts using the assigned materials. In FIG. 9, a computer 9066 acts as a host computer for an additive manufacturing system 9068 and communicates with system 9068 over one or more communication lines 9070. In some embodiments, computer 9066 is internal to system 9068, such as part of an internal controller assembly for system 9068. In other embodiments, computer 9066 is external to additive manufacturing system 9068.

Figure 10:
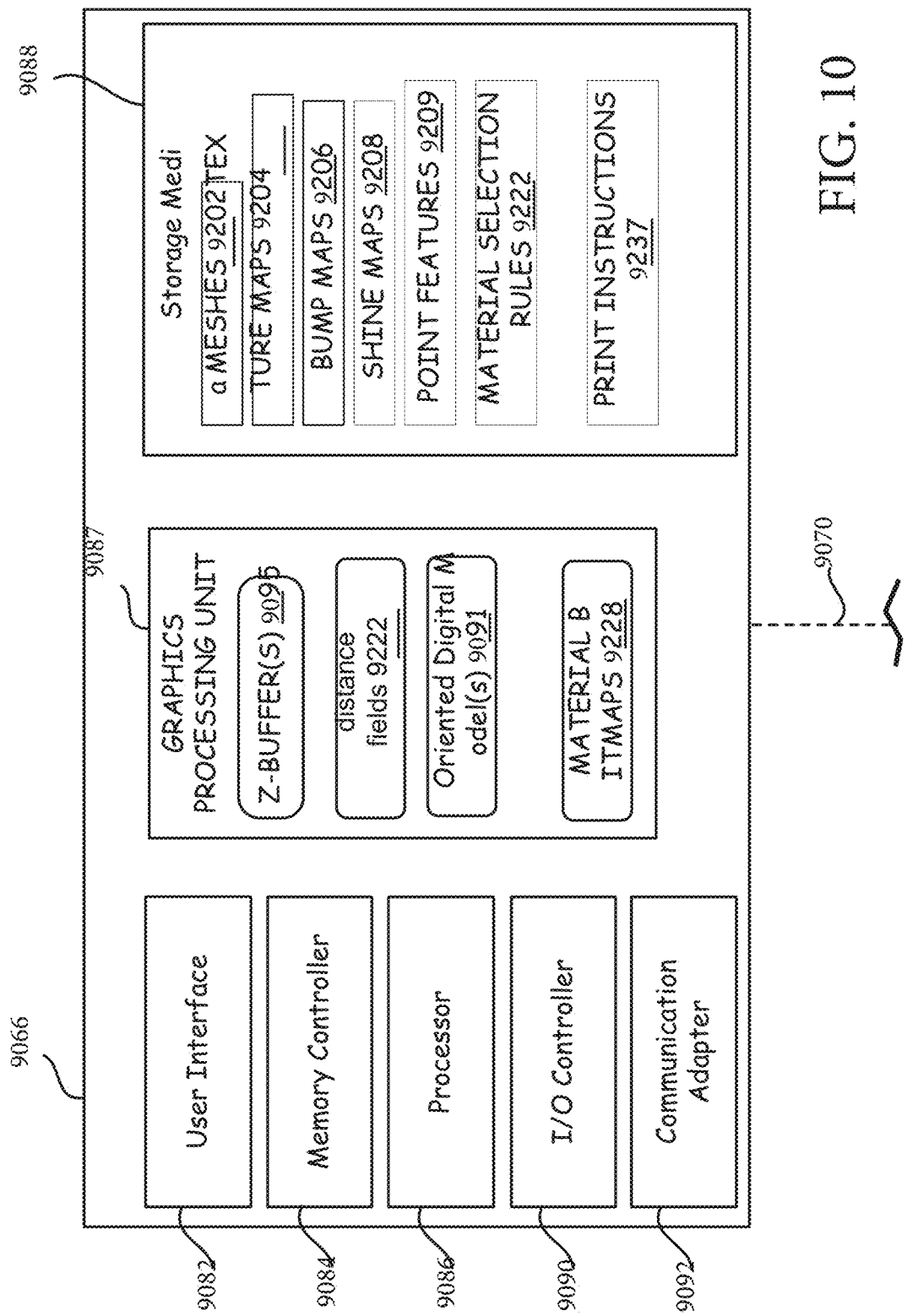
FIG. 10 is a block diagram of an example computer architecture for the computer of FIGS. 1A-D.

FIG. 10 shows a block diagram of an example architecture for computer 9066. As shown, computer 9066 includes suitable computer-based hardware, such as a user interface 9082, a memory controller 9084, a processor 9086, a graphics processing unit 9087, a storage media 9088, an input/output (I/O) controller 9090, and a communication adapter 9092. Computer 9066 may also include a variety of additional components that are contained in conventional computers, servers, media devices, signal processing devices, and/or printer controllers.

User interface 9082 is one or more user-operated interfaces (e.g., keyboards, touch pads, touch-screen displays, display monitors, and other eye, voice, movement, or hand-operated controls) configured to operate computer 9066. Memory controller 9084 is one or more circuit assemblies that interface the components of computer 9066 with one or more volatile random access memory (RAM) modules of storage media 9088. Processor 9086 is one or more computer-processing units configured to operate computer 9066, optionally with memory controller 9084, and preferably with related processing circuitry (e.g., programmable gate arrays, digital and analog components, and the like). For instance, processor 9086 may include one or more microprocessor-based and/or microcontroller-based units, one or more central processing units, and/or one or more front-end processing units.

Graphics processing unit 9087 contains a large number of transistors that are arranged to perform calculations related to 3D computer graphics in a fast an efficient manner. Such calculations include texture mapping and rendering polygons that represent 3D objects.

Storage media 9088 is one or more internal and/or external data storage devices or computer storage media for computer 9066, such as volatile RAM modules, read-only memory modules, optical media, magnetic media (e.g., hard disc drives), solid-state media (e.g., FLASH memory and solid-state drives), analog media, and the like. Storage media 9088 may retain one or more pre-processing and/or post-processing programs (not shown) discussed further below.

I/O controller 9090 is one or more circuit assemblies that interface memory controller 9084, processor 9086, and storage media 9088 with various input and output components of computer 9066, including user interface 9082 and communication adapter 9092. Communication adapter 9092 is one or more wired and/or wireless transmitter/receiver adapters configured to communicate over communication lines 9070.

The commands from computer 9066 to the components of systems 9068 may be performed with one or more of user interface 9082, memory controller 9084, processor 9086, storage media 9088, input/output (I/O) controller 9090, communication adapter 9092, and/or other suitable hardware and software implementations, as is understood by those skilled in the art.

Figure 11:
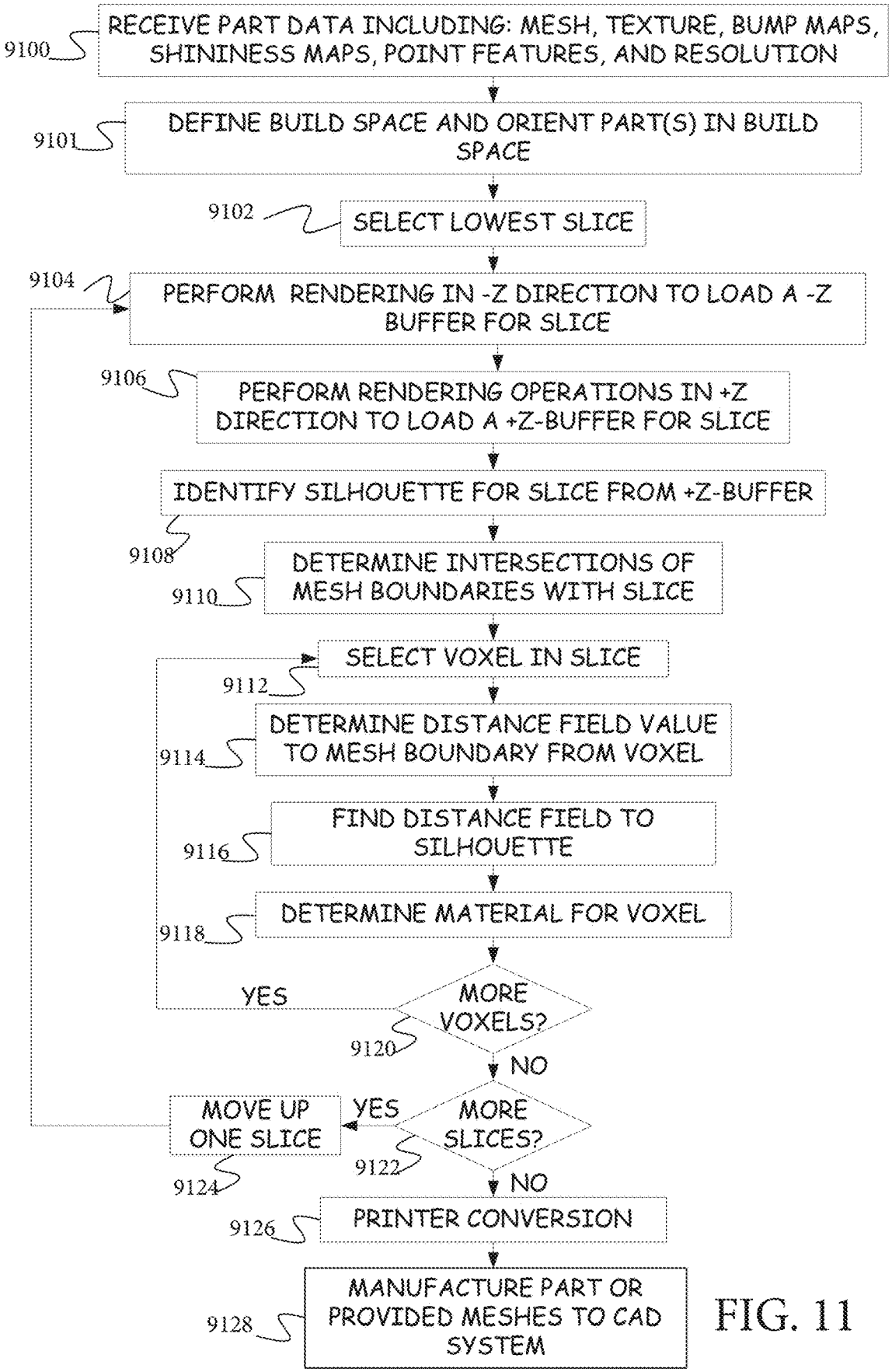
FIG. 11 is a flow diagram of a method of converting a 3D model into print instructions and printing a 3D part.
Figure 12:
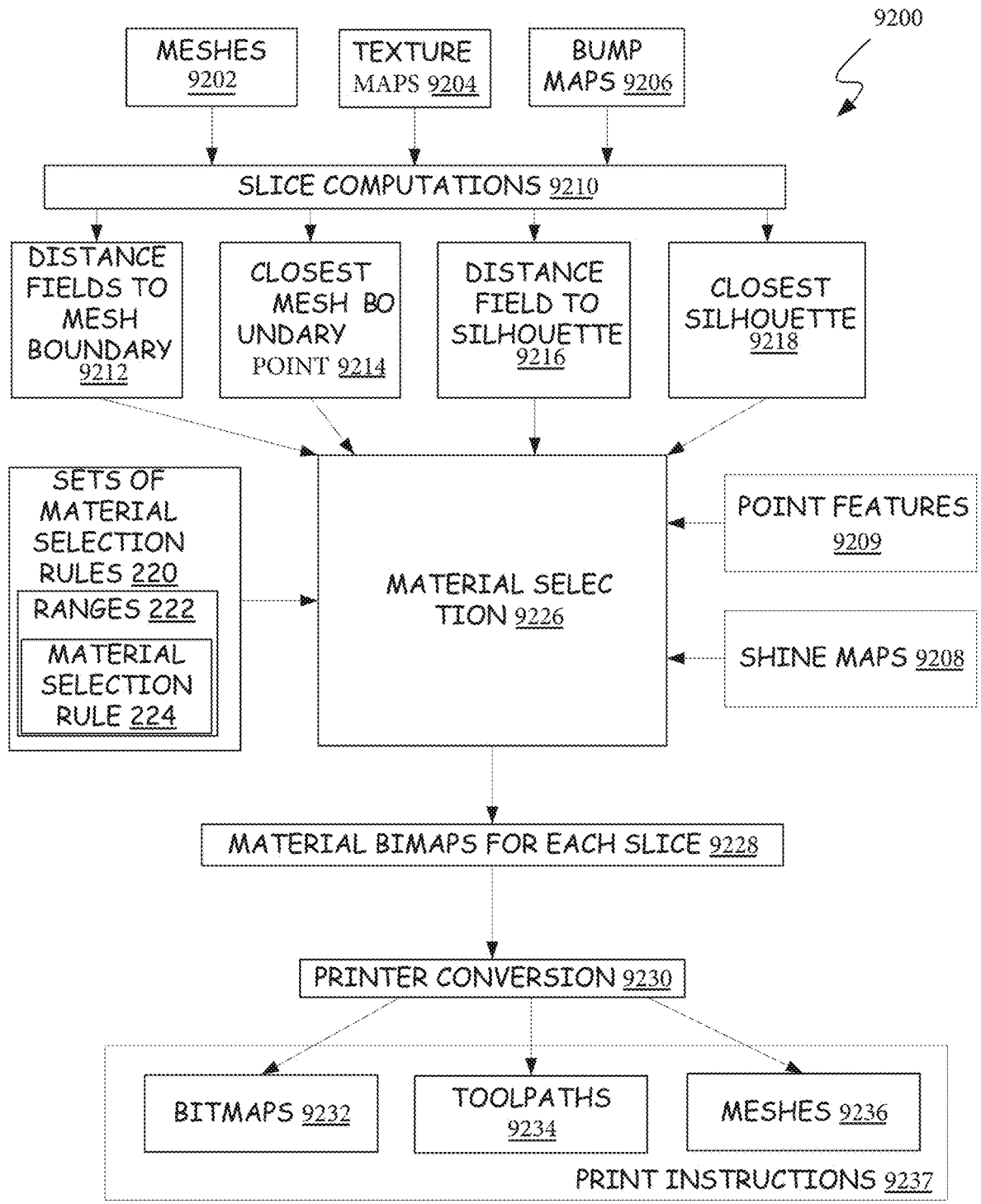
FIG. 12 is a block diagram of elements used in the method of FIG. 11.

FIG. 11 provides a flow diagram of a method of generating print instructions from part models using distance fields. FIG. 12 provides a block diagram of a system 9200 used to implement the method of FIG. 11. In accordance with one embodiment, system 9200 is implemented in computer 9066.

Figure 13:
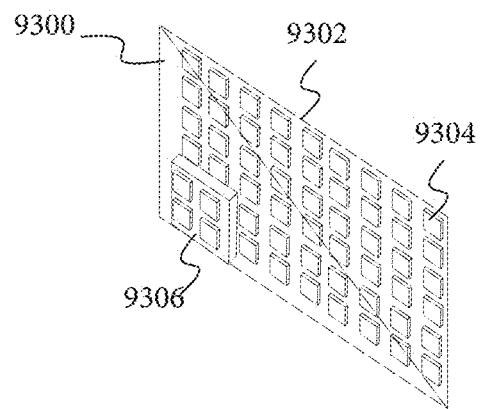
FIG. 13 is a perspective view of a portion of a part showing texture and a bump.

In step 9100, part data is received including meshes 9202, texture maps 9204, bump maps 9206, shine maps 9208, point features 9209 and a part resolution, which are stored in storage media 9088. Meshes 9202 describe planar boundaries of the part and can be defined as interconnected triangles or interconnected quadrilaterals. Texture maps 9204 describe the location and geometry of surface textures to be applied on the outside of each of the surfaces described by meshes 9202. Bump maps 9206 provide descriptions of larger surface features present on particular surfaces of the meshes 9202. FIG. 13 provides an example of a portion of a part showing two surfaces 9300 and 9302 having textures marked by the raised squares 9304 and a surface bump 9306 represented by the large raised square. The small squares 9304 would be described in the texture maps 9204 while the surface bump 9306 would be described in the bump maps 9206. Shininess maps 9208 indicate a desired level of shine for different surfaces of the part.

Point features 9209 describe sets of material selection rules to be used for portions of the part having specific features. Examples of part features that can be used as the basis for assigning sets of material selection rules include identifiers of a body or mesh, surface texture coordinates, and surface normal ranges. Thus, in some embodiments, different portions of a part have different sets of material selection rules such that at the same distance field values, different materials will be used for different areas around the part. A further description of the use of such point features is provided below.

Meshes 9202, texture maps 9204 and bump maps 9206 are provided to a slice computations process 9210 executed by graphics processing unit 9087, which performs step 9101-9116, 9120, 9122 and 9124 of FIG. 11 described further below.

At step 9101, slice computations process 9210 defines a three-dimensional build space and orients the parts described by meshes 9202, texture maps 9204 and bump maps 9206 in the three-dimensional build space to form oriented digital models 9091. In accordance with one embodiment, the build space is defined by first orienting the digital parts and then defining a bounding box around the oriented parts to provide a support structure envelope around the parts.

Figure 14:
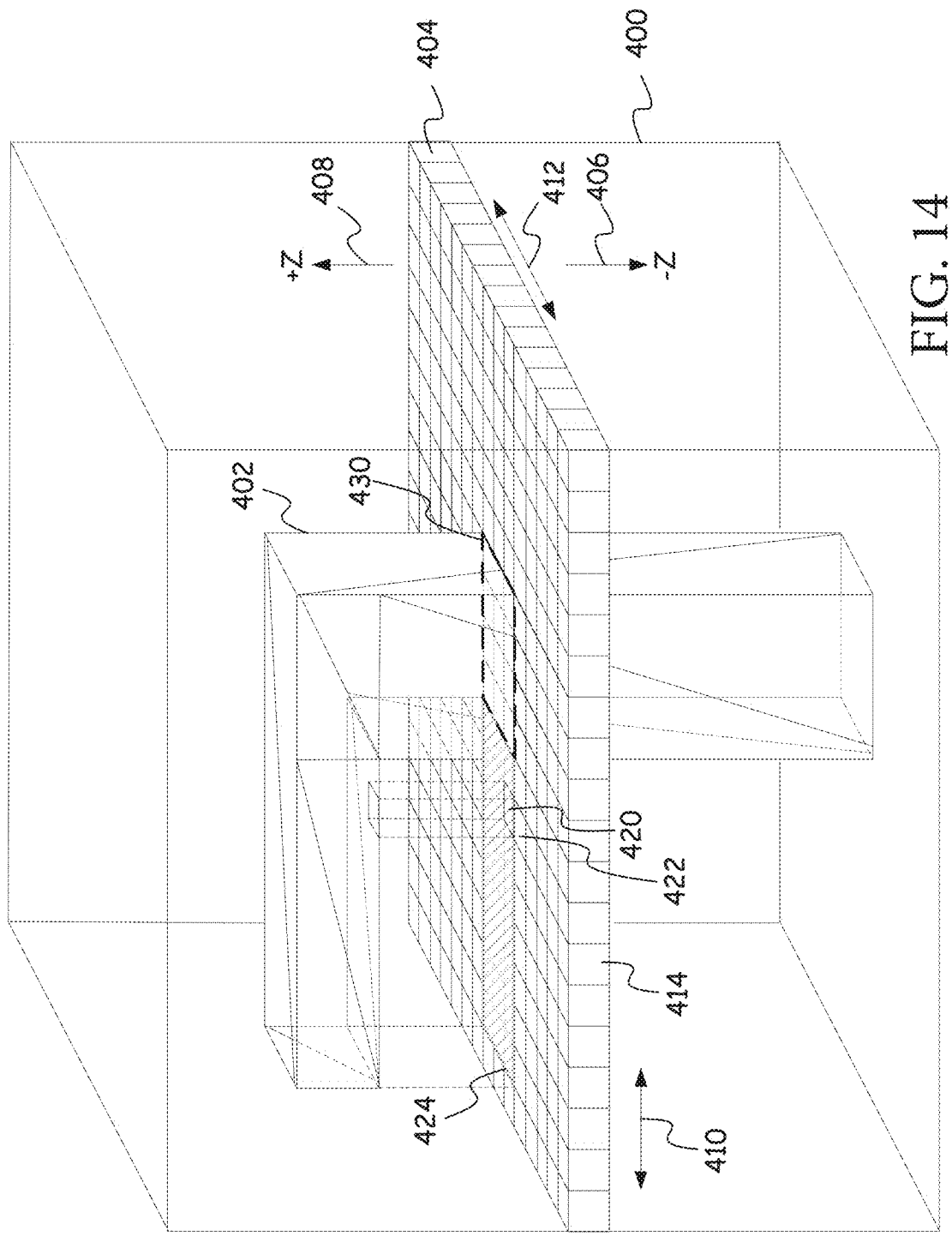
FIG. 14 is a perspective view of a build space with an oriented part.

FIG. 14 provides a three-dimensional view of a three-dimensional part model 402 oriented in a three-dimensional build space 400. In FIG. 14, there is a −Z direction 406, a +Z direction 408, an X direction 410 and a Y direction 412. A slice 400 of build space 400 is shown to include a collection of voxels, such as voxel 414. Although only a single slice is shown in FIG. 14, there are multiple slices in build space 400 such that voxels fill the entirety of build space 400. The dimensions of the voxels are based on the resolution set for the part.

At step 9102, slice computations process 9210 sets values for Z buffer 9095 for each slice in build space 400. The Z buffer for a slice contains a value for each voxel in the slice, where the magnitude of the Z buffer value represents the magnitude of the vertical distance between the voxel and the closest STL boundary of the part. The STL boundary of the part is constructed from the combination of one or more meshes 9202, texture maps 9204 applied to those meshes, and bump maps 9206 applied to those meshes. In step 9102, this distance is determined by looking in −Z direction 406 from the voxel and the Z buffer is therefore referred to as the −Z buffer. The sign of the Z buffer value indicates whether the voxel is inside or outside the part with negative values indicating that the voxel is outside of the part and positive values indicating that the voxel is inside the part. Initially, all of the −Z buffer values for a slice are set to a maximum negative value, which indicates that no portion of the part is visible in −Z direction 406 from any of voxels.

A rendering operation is then performed by GPU 9087 using meshes 9202, texture maps 9204 and bump maps 9206 to construct a description of the STL boundaries of the part in three-dimensional build space 400 and to project that description onto the slice. In particular, each surface in meshes 9202 are rendered one at a time and the texture maps 9204 and bump maps 9206 are applied to the rendered surfaces to produce the STL boundaries for the surface and the resulting STL boundaries for the surfaces are projected onto the slice by identifying the voxels that are directly above the STL boundaries in the three-dimensional build space. For each voxel that is directly above the STL boundaries of a surface, the distance between the STL boundary and the voxel is compared to the current distance stored in the −Z buffer for the voxel. If the distance to the surface currently being projected has a smaller magnitude than the value stored in the −Z buffer, the current surface is considered to be closer to the voxel than any previously rendered surfaces of the part and the −Z buffer is updated with the distance to the current STL boundary.

The sign of the distance value stored in the −Z buffer is set to indicate whether the voxel is inside or outside the part. This can be determined based on the angle between the outward normal of the current surface and the +Z direction 408. In accordance with one embodiment, the identity of the current surface is also stored in an additional buffer for the slice. If the distance between the current STL boundary and the voxel is larger than the magnitude of the Z buffer value for the voxel, the Z buffer value remains unchanged. This will occur when the current surface is obscured from the voxel by another surface of the part, which is closer to the voxel. Thus, after every surface of the part below the current slice has been rendered and projected onto the slice, the Z buffer contains values indicating the shortest distance in the Z direction between the voxel and the STL boundary of the part and a further buffer indicates the identity of those closest surfaces. This is repeated for each slice in build space 400.

The loading of Z buffers using graphical processing units is common in rendering 3D computer models of objects onto 2D planes. However, using such graphical processing units to load Z buffers associated with voxels as part of constructing three-dimensional parts has not been known.

After the −Z buffers have been formed for all of the slices in build space 400 the lowest slice in build space 400 is selected at step 9104. At step 9106, a rendering operation is performed in the +Z direction to load a +Z buffer for the selected slice. This rendering is identical to the rendering performed in the −Z direction with the exception that the view is changed to +Z direction 408. After step 9106, the selected slice has a +Z buffer value for each voxel and a −Z buffer value for each voxel where the +Z buffer value provides the shortest vertical distance between the voxel and the part in +Z direction 408 and the −Z buffer value provides the shortest distance between the voxel and the part in −Z direction 406.

Although steps 9102 and 9106 are described above with reference to one part in build space 400, in other embodiments, multiple parts are present in build space 400. When multiple parts are present in build space 400, a separate −Z buffer and a separate +Z buffer is created for each part for each slice in build space 400.

At step 9108, silhouette boundaries for the selected slice are determined from the +Z buffer(s). In particular, the +Z buffer values for pairs of voxels are examined to identify transitions from a negative value to the greatest magnitude negative value possible. Such transitions represent a boundary between where a portion of a part is above a voxel and no portion of the part is above the voxel's neighbor. An example of such a boundary can be seen in FIG. 14 where voxels 420 and 422 are positioned along such a boundary. Voxel 420 is positioned below part 402 and has a +Z buffer value of −4. Voxel 422, which neighbors voxel 420, is not below any portion of the part and as such has the largest possible negative value, for example −10000, in the +Z-buffer. Repeating this pairwise comparison for every pair produces silhouette boundaries, such as silhouette boundary 424 where voxels within the boundary are considered to be underneath a portion of the part and voxels outside of the silhouette are not below any portions of a part. Note that when multiple parts are present in build space 400, step 9108 is repeated for each +Z buffer for the slice selected at step 9104.

At step 9110, slice computations process 9210 determines the intersections of STL boundaries with the current slice. In FIG. 14, the intersection of the STL boundary and slice 400 is shown as boundary 430, shown in dotted lines. The intersection of the STL boundaries with the slice can be found by examining the +Z buffer and the −Z buffer to identify neighboring pixels where the Z buffer value changes from a negative value to a value of 0 or from a negative value to a positive value. Such changes in the Z-buffer values indicate a transition from being outside of the part to being within the part. Step 9110 is performed for each part's Z buffers.

At step 9112, a single voxel in the current slice is selected. At step 9114, a distance field value to the part's STL boundaries is determined for the voxel. This distance field value is the shortest magnitude distance between the voxel and any portion of the part's STL boundaries. At step 9116, if the current voxel is outside of the part, the distance to the silhouette boundary is determined for the current voxel.

In accordance with one embodiment, steps 9114 and 9116 are performed together using a sampling algorithm. One example of such a sampling algorithm is shown in the flow diagram of FIG. 15, which is explained with reference to FIG. 16. In FIG. 16, a top view of a slice 620 is shown with a matrix of voxels, including current voxel 600. An STL boundary 612 that intersects slice 600 is shown as a solid line and a silhouette boundary 610 is shown as a dotted line.

Figure 15:
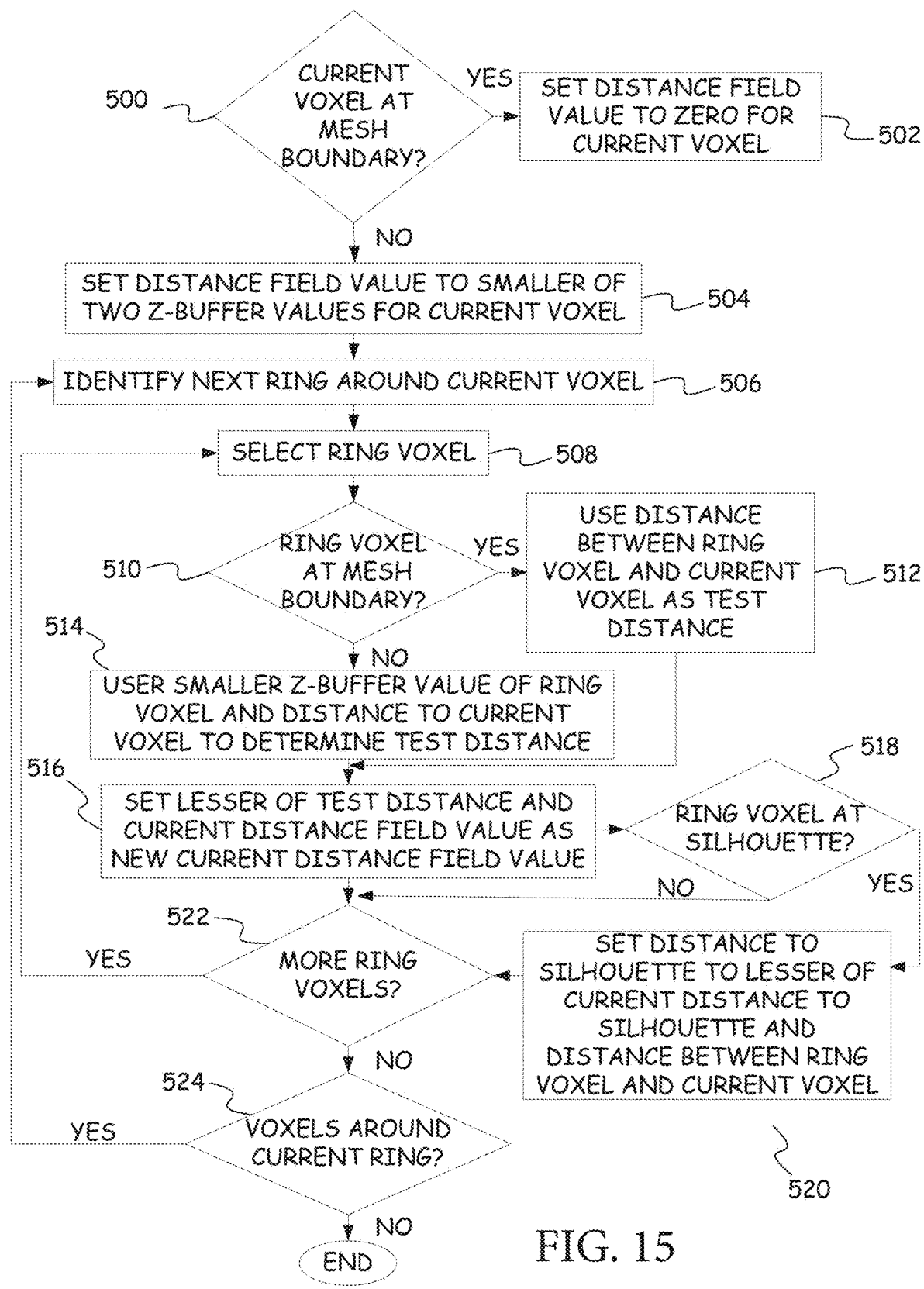
FIG. 15 is a method of determining a distance field value.
Figure 16:
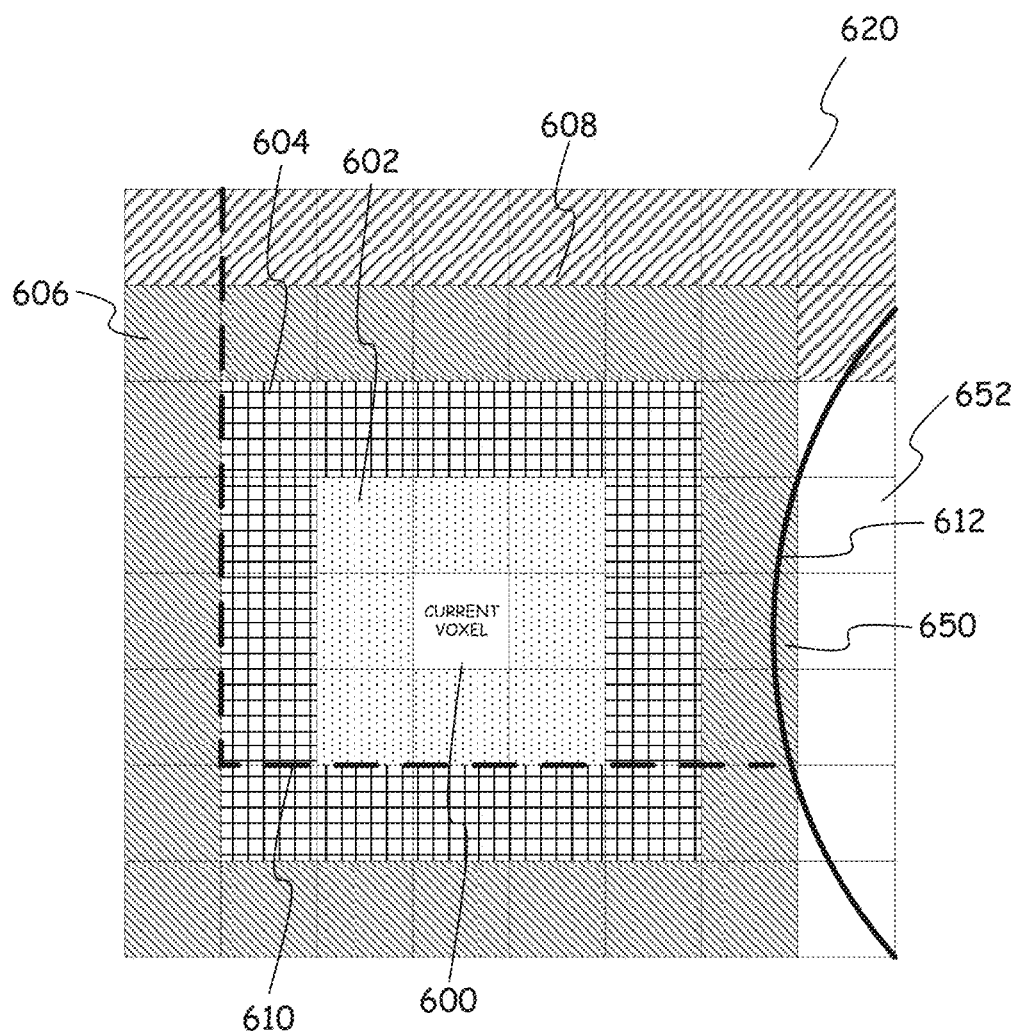
FIG. 16 is a top view of a slice in the build space showing the determination of a distance field value.

At step 500 of FIG. 15, the current voxel, voxel 600 of FIG. 16, is examined to determine if it is at an STL boundary in the current slice. For example, in FIG. 16, voxel 650 would be considered to be at STL boundary 612 since STL boundary 612 intersects with voxel 650. If the current voxel is at the STL boundary at step 500, the distance field value is set to 0 for the current voxel at step 502.

If the current voxel is not at the STL boundary at step 500, as is shown with current voxel 600 of FIG. 16, step 504 of FIG. 15 is performed where the distance field value for current voxel 600 is set to the smaller of the two Z-buffer values for the current voxel. In particular, the magnitudes of the Z distance value in the +Z-buffer and −Z-buffer are compared and the smaller magnitude is set as the distance field value for the current voxel. In addition, the sign of the distance field value is set based upon whether the voxel is inside or outside of the part. If the voxel is inside the part, the distance field value is set as a positive value and if the voxel is outside of the part, the distance field value is set to a negative value.

At step 506, a ring of voxels around the current voxel in the current slice is identified. For example, in FIG. 16, a first ring 602 indicated by the dotted shading surrounds current voxel 600. At step 508, a voxel in the identified ring is selected. If this selected ring voxel is at the STL boundary at step 510, the distance between the selected ring voxel and the current voxel 600 is used as a test distance. If the ring voxel is not at the STL boundary, a combination of the smaller of the two Z-buffer values for the ring voxel and the distance between the ring voxel and the current voxel is used to determine the test distance at step 514. In particular, the Z-buffer values in the +/−Z-buffer for the ring voxel are compared to each other and the smaller magnitude of the two Z-buffer values is selected as a vertical component of the distance to the part. A horizontal component of the distance of the part is computed as the distance between the ring voxel and the current voxel 600. Squaring the vertical component of the distance and the horizontal component of the distance, summing the squares, and taking the square root of the sum provides the distance between the current voxel 600 and the portions of the part above or below the ring voxel. Note that if no portion of the part is above or below the ring voxel, the Z-buffers will each contain large magnitude values.

The test distance value computed in either step 512 or 514 is then compared to the current stored distance field value for the current voxel 600 at step 516. If the test distance is less than the current distance field value, the test distance is set as the new current distance field value. If the magnitude of test distance is not less than the magnitude of the current distance field value, the current distance field value remains the same.

At step 518, the method determines if the ring voxel is at the silhouette boundary, such as silhouette boundary 610 of FIG. 16. If the ring voxel is at the silhouette boundary, a shortest distance to the silhouette boundary for current voxel 600 is set to the lesser of a previously stored distance to the silhouette boundary for current voxel 600 and the distance between the ring voxel and the current voxel at step 520. Thus, if the ring voxel is at the silhouette boundary and the distance between the ring voxel and the current voxel is smaller than previously identified distances between the current voxel and the silhouette boundary, the shortest distance between the current voxel 600 and the silhouette boundary is updated to reflect the distance between the ring voxel and the current voxel 600.

If the ring voxel is not at the silhouette boundary or after the distance to the silhouette boundary has been updated, the process of FIG. 15 determines if there are more ring voxels in the current selected ring. If there are more ring voxels, the process returns to step 508 and the next voxel in the current ring is selected. Steps 510-522 are then repeated. When all of the voxels in a current ring have been processed at step 522, the method determines if there are more voxels around the current ring at step 524. If there are more voxels around the current ring at step 524, the process returns to step 506 and the next ring around the current ring of voxels is selected. For example, after ring 602 is processed, ring 604 is processed, then ring 606, then ring 608. In processing successive rings, the STL boundaries are not crossed. As such, once an STL boundary is reached, voxels on the other side of the boundary are not processed. For example, voxel 652 is not processed as part of ring 608 since STL boundary 612 separates voxel 652 from current voxel 600. The same is true for rings of voxels that are processed within a part. Specifically, when a current voxel is located within a part, voxels outside of the part are not used to determine the distance field for the voxel.

When there are no more voxels around the current ring at step 524, the process ends and the distance field value stored for the current voxel is output as the final distance field 9212 (FIGS. 10 and 12). This distance field value will have a magnitude representing the shortest distance between the current voxel and any STL boundary of the part and a sign that will indicate whether the current voxel is within the part or is exterior to the part. In addition, when the distance field value is updated for the current voxel, one or more features associated with the distance field value are also stored such as the position of the closest point on the STL boundary, identifiers of the body or mesh that the closest point is located on, surface texture coordinates, and the surface normal at the closest point, for example. In accordance with one embodiment, different features of the part have different sets of material selection rules associated with them. As a result, different portions of the part can have different material selection rules associated with it. Similarly, the shortest distance to the silhouette boundary 9216 is output as is the location of the closest silhouette boundary point 9218.

When there are multiple parts in build space 400, the steps of FIG. 15 are repeated for each part to generate a distance field value 9212, a closest STL boundary point 9214, a closest distance to the silhouette 9216 and the closest silhouette boundary point 9218 for the voxel for each part. It is possible for a single voxel to be outside of all parts, to be located in a single part while outside of other parts, or to be located within multiple parts.

Figure 17:
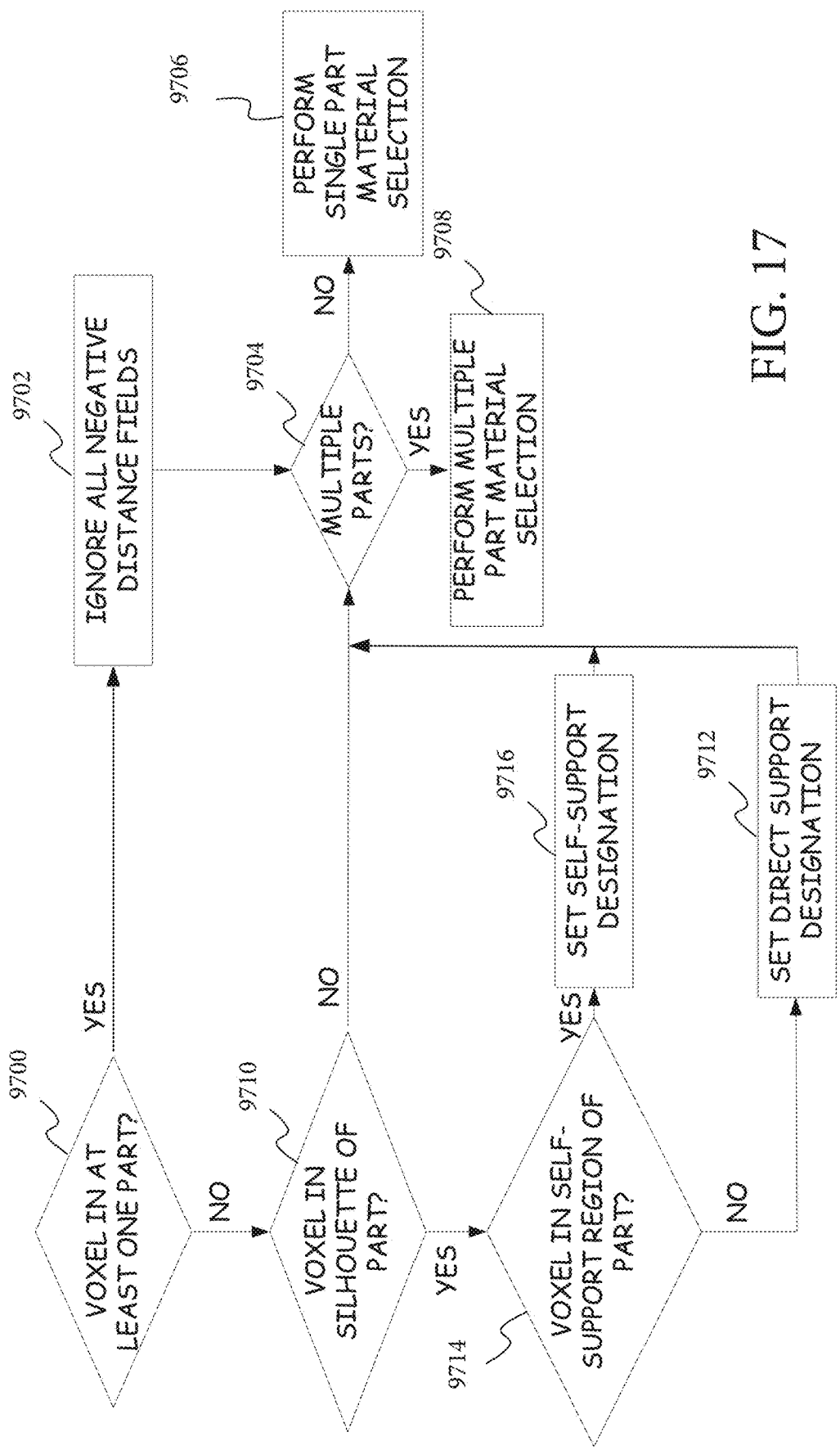
FIG. 17 is a flow diagram of a method of performing initial steps of material selection.

Returning to FIG. 11, after the distance field values and the distance to the silhouette boundary have been determined for the selected voxel at steps 9114 and 9116, respectively, material for the voxel is determined at step 9118 by a material selection unit 9226. FIG. 17 provides a flow diagram showing initial steps in performing the material selection.

At step 9700, the distance fields are examined to determine if the voxel is in at least one part. This determination can be made by determining if there is at least one non-negative distance field value stored for the voxel. If the voxel is in at least one part, all negative distance field values for the voxel are ignored at step 9702. Thus, if a voxel is located within at least one part, the material selection rules 9220 associated with the voxel being inside part(s) control the material selection and the material selection rules 9220 associated with the voxel being outside of other parts are ignored. Note that if there is only one part in the build space, there will be no negative distance fields to ignore at step 9702.

At step 9704, material selection unit 9226 determines if there are multiple parts in the build space. If there is only one part in the build space, a single-part material selection process is performed at step 9706. An example of one such single-part material identification process is discussed further below. If there are multiple parts at step 9704, a multipart material selection process is performed at step 9708. One example of such a multipart material selection process is discussed below.

Returning to step 9700, if the voxel is not in any of the parts in the build space, the voxel's position relative to the silhouette boundary is examined at step 9710 to determine if the voxel is in a direct support region for a part. A direct support region is a region in the build space located within a silhouette of a part. Such direct support regions require sufficient support material to support the part as it is built. Determining whether a voxel is in a direct support region involves looking at the +Z-buffer value(s) for the voxel. If any of the +Z-buffer value(s) is negative and has a magnitude less than the maximum magnitude, the voxel is in a direct support region. If the voxel is in a direct support region, a direct support designation is set at step 9712 for the voxel.

If the voxel is not in a direct support region at step 9710, the voxel's position is examined to determine if it is in an angled support region for the part at step 9714. For some parts, in addition to providing additional support in the direct support regions, additional support is also provided outside of the silhouette of the part so that the additional support has an angled surface and is not completely vertical. To determine if the voxel is in an angled support region for the part, the distance to the closest silhouette boundary for the part is combined with the vertical distance to the part from that closest point on the silhouette boundary to determine an angle between the voxel and the portion of the part above the silhouette boundary relative to the xy plane of the slice. If this angle is greater than some maximum angle set for the angled support region, the voxel is considered to be within the angled support region at step 9714. If the computed angled is less than the maximum angle for the angled support region, the voxel is considered to be outside of the angled support region for the part. If the voxel is within the angled support region at step 9714, a designation that the voxel is in the angled support region is set at step 9716. After step 9714 or step 9716, the process moves to step 9704 to determine if there are multiple parts in the build space.

Figure 18:
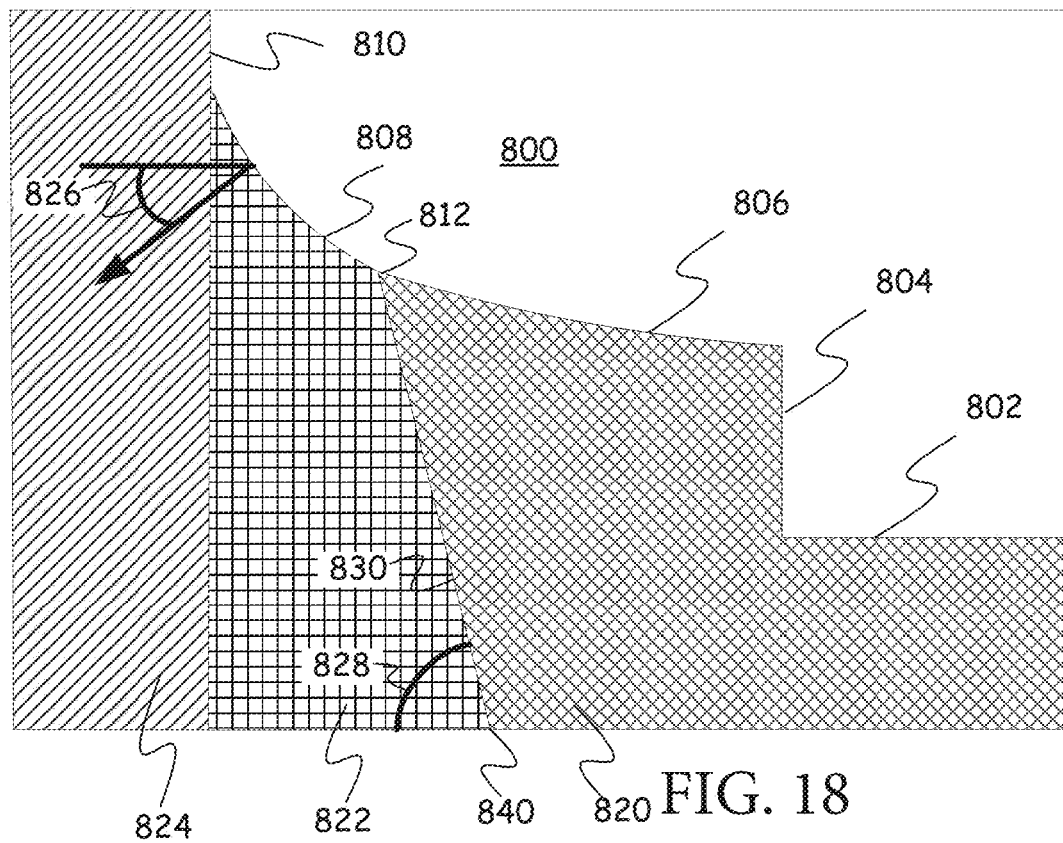
FIG. 18 provides a side view of a part showing different support regions.

FIG. 18 provides a diagram showing a full support region 800, an angular support region 802 and a fill support region 804 for a part 806. Full support region 800 includes areas outside of the part that are within silhouette boundary 810 of the part. Angular support region 802 includes areas that are within an angle 812 of point 814 of the part at silhouette boundary 810. Full support region 800, angular support region 802 and fill support region 804 can each include different materials and/or different modulating functions from each other. In general, full support region 800 will include materials and modulating functions that provide more support than fill support region 804. Angular support region 802 can include the same materials and modulating functions as full support region 800 or may include different materials or modulating functions.

Figure 19:
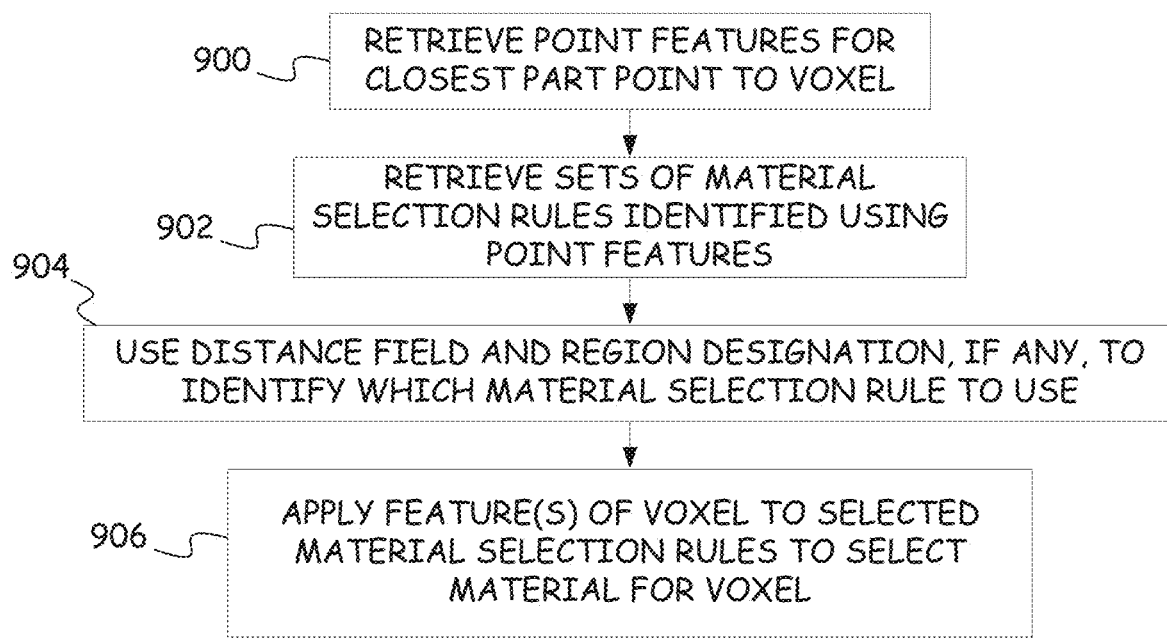
FIG. 19 provides a method of selecting a material for a voxel when there is only one part.

FIG. 19 provides a flow diagram for performing step 9706 of FIG. 17 in which a material identification is performed with respect to a single part in the build space. At step 900 of FIG. 19, point features for the closest portion of the part to the voxel are retrieved from point features 9209 by material selection unit 9226. These point features are used to identify a set of material selection rules 9220 to be used when determining the material for voxels near the part portion. In accordance with one embodiment, the set of material selection rules contains a separate material selection rule 9224 for each of a set of ranges 9222 of distance field values. In accordance with some embodiments, each material selection rule is one of a static rule that assigns a same material at a same density across the entire range of distance field values, and a modulating rule that varies the composition of the voxels across the range of distance field values.

At step 902, material selection unit 9226 retrieves the sets of material selection rules identified in the point features and at step 904 uses the distance field and the region designation (i.e. direct support region, filler region), if any, for the voxel to identify which material selection rule to use.

In accordance with one embodiment, ranges 9222 describe bands of materials relative to the STL boundary where each band has an associated material selection rule 9224. Within a range 9222, the material selection rule 9224 can simply designate a single material to use within the range. For other ranges, the material selection rule 9224 consists of one or more functions that are evaluated to produce output values. Groups of output values are assigned to different material designations. For example, some output values of the functions can be assigned to a first material while other output values are assigned to a second material. Other times, one group of output values is assigned to a material while the remaining output values are assigned to no material, meaning that no material is placed in the voxel. For example, in accordance with one embodiment, the following bands and functions are defined:

for a>D>b
$f(\bar{x}, D)>0 \rightarrow$ material designation 1
$f(\bar{x}, D)<0 \rightarrow$ material designation 2
$f(\bar{x}, D)=0 \rightarrow$ material designation 3
for b>D>0
$g(\bar{x}, D)>0 \rightarrow$ material designation 4
$g(\bar{x}, D)<0 \rightarrow$ material designation 5
$g(\bar{x}, D)=0 \rightarrow$ material designation 6
for D=0
$h(\bar{x})>0 \rightarrow$ material designation 7
$h(\bar{x})<0 \rightarrow$ material designation 8
$h(\bar{x})=0 \rightarrow$ material designation 9
or 0>D>−c and direct support
$k(\bar{x}, D)>0 \rightarrow$ material designation 10
$k(\bar{x}, D)<0 \rightarrow$ material designation 11
$k(\bar{x}, D)=0 \rightarrow$ material designation 12
for 0>D>−c and angled support
$l(\bar{x}, D)>0 \rightarrow$ material designation 13
$l(\bar{x}, D)<0 \rightarrow$ material designation 14
$l(\bar{x}, D)=0 \rightarrow$ material designation 15
for 0>D>−c and nonshine
$m(\bar{x}, D)>0 \rightarrow$ material designation 16
$m(\bar{x}, D)<0 \rightarrow$ material designation 17
$m(\bar{x}, D)=0 \rightarrow$ material designation 18
for 0>D>−c and shine
$n(\bar{x}, D)>0 \rightarrow$ material designation 19
$n(\bar{x}, D)<0 \rightarrow$ material designation 20
$n(\bar{x}, D)=0 \rightarrow$ material designation 21
for −c>D>−d and direct support
$o(\bar{x}, D)>0 \rightarrow$ material designation 21
$o(\bar{x}, D)<0 \rightarrow$ material designation 22
$o(\bar{x}, D)=0 \rightarrow$ material designation 23
for −c>D>−d and angled support
$p(\bar{x}, D)>0 \rightarrow$ material designation 24
$p(\bar{x}, D)<0 \rightarrow$ material designation 25
$p(\bar{x}, D)=0 \rightarrow$ material designation 26
for −c>D>−d and otherwise
$q(\bar{x}, D)>0 \rightarrow$ material designation 27
$q(\bar{x}, D)<0 \rightarrow$ material designation 28
$q(\bar{x}, D)=0 \rightarrow$ material designation 29 where D is the distance field value, a, b, −c and −d are range values for the distance field values, $\bar{x}$ is the three-dimensional location of the voxel in the build space, $f(\bar{x}, D)$, $g(\bar{x}, D)$, $h(\bar{x}, D)$, $k(\bar{x}, D)$, $l(\bar{x}, D)$, $m(\bar{x}, D)$, $n(\bar{x}, D)$, $o(\bar{x}, D)$, $p(\bar{x}, D)$, and $a(\bar{x}, D)$ are modulating functions and material designations 1-29 are possible materials and no materials to be used for the voxel. Although listed as separate materials 1-29, those skilled in the art will recognize that one or more of the material designations may be the same.

The modulating functions can be periodic or aperiodic functions of one or more features of the voxel such as the voxel's position in the build space, or the distance field D for the voxel. For periodic functions, the position in the build space or the distance field or a combination of these two values can be used to control the frequency of the periodic function, a temporal shift in the periodic function and/or the magnitude of the periodic function. The modulating function can also be a noise function based on the voxel's position in the build space or based on the distance field. In further embodiments, the modulating function is a combination of a periodic function and a noisy function. For example, in one embodiment, the periodic function is based on both the position in the build space and the distance field and the output of the periodic function is filtered by a noisy filter based on the voxel's position in the build space. In a still further embodiment, the modulating function is the sum of the distance field value and a base periodic function of the voxel position in the build space.

In the examples above, three ranges of values for the functions have been described with three associated material designations. When the modulating function provides a constant value, only a single material will be identified producing a band of solid material across the range set by the distance field. In other embodiments, other ranges of values for output of the modulating function are used allowing for any number of materials to be used within the range of distance field values set for the modulating function. In further embodiments, one or more of the ranges of values for the modulating function can be associated with empty space resulting in no material being assigned to the voxel. For example, it is possible to assign a material when the output of the modulating function is greater than or equal to 0 and to assign an empty space to the voxel when the output of the modulating function is less than 0. This allows a porous band of material to be constructed with the porosity of the material changing as a function of the distance field and/or the position in the build space.

The frequency of the modulating function can change as a continuous function of the distance field or can be fixed at the value of the distance field at the beginning or the end of the range of distance fields associated with the modulating function. Similarly, the amplitude of the modulating function can similarly vary continuously as a function of the distance field values or can be set to the value of the distance field at the beginning or ending range of distance field values associated with the modulating function.

As shown in the example set of material selection rules above, the selection of a material selection rule can also be based upon whether the voxel is located in a direct support region or an angled support region as designated for the voxel in step 9712 and 9716 above. In addition, shine maps 9208 can be consulted for the portion of the part closest to the voxel to determine whether that portion of the part is to have a particular shine level. This shine level can then be used together with the distance field to select the material selection rule to apply to the voxel.

Returning to FIG. 19, at step 906, the distance field value of the voxel and/or the build space position of the voxel are applied to the selected material selection rule to select a material or no material for the voxel. In some embodiments, as shown above, the material selection rule 9224 is a function of a feature of the voxel, such as the distance field value or the build space position of the voxel, and the distance field value and or the build space position of the voxel are applied to the function to generate an output value that is then used to select the material or lack of material for the voxel.

Figure 20:
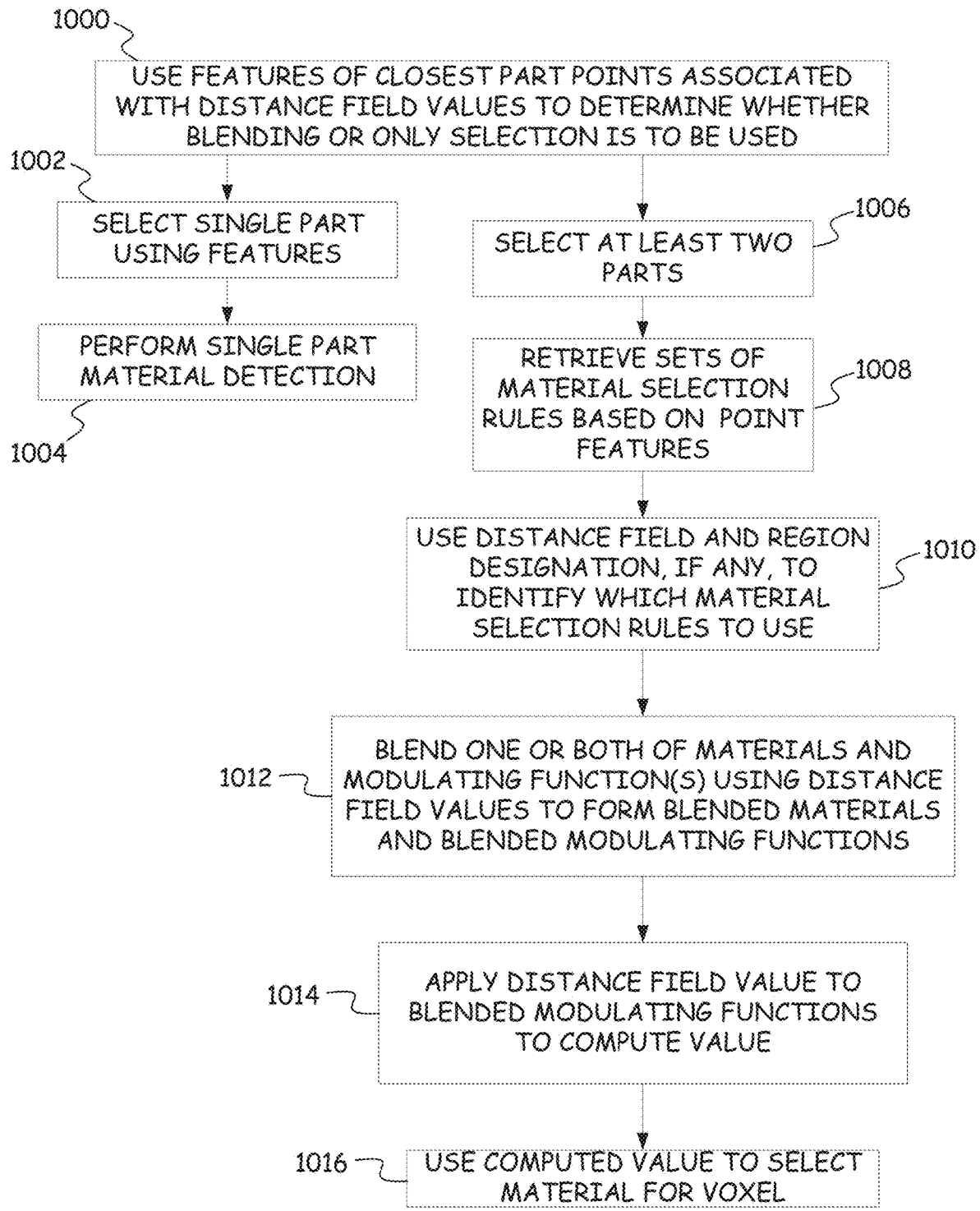
FIG. 20 provides a method of selecting a material for a voxel when there are multiple parts in the build space.

If there is more than one part in the build space, a multipart material selection is performed at step 9708 of FIG. 17. FIG. 20 provides a flow diagram of one method for performing a multipart material selection.

At step 1000, material selection unit 9226 accesses point features 9209 to retrieve the features for the closest STL boundary points 9214 for the multiple parts. These features are then used to determine whether the material selection rules designated for the STL boundary point are to be blended with the material selection rules for STL boundary points of other parts or whether a selection is to be made between the material selection rules of the various parts so that only a single part's material selection rules are used.

If only a single part's material selection rules are to be used, the process continues at step 1002 where one of the parts is selected using the closest STL boundary points of the various parts. In particular, the features 9209 of the closest STL boundary points will indicate which of the parts is to be given priority when selecting a set of material selection rules. After the part with priority has been selected at step 1002, single part material selection is performed at step 1004 using the process described above for FIG. 19.

Figure 21:
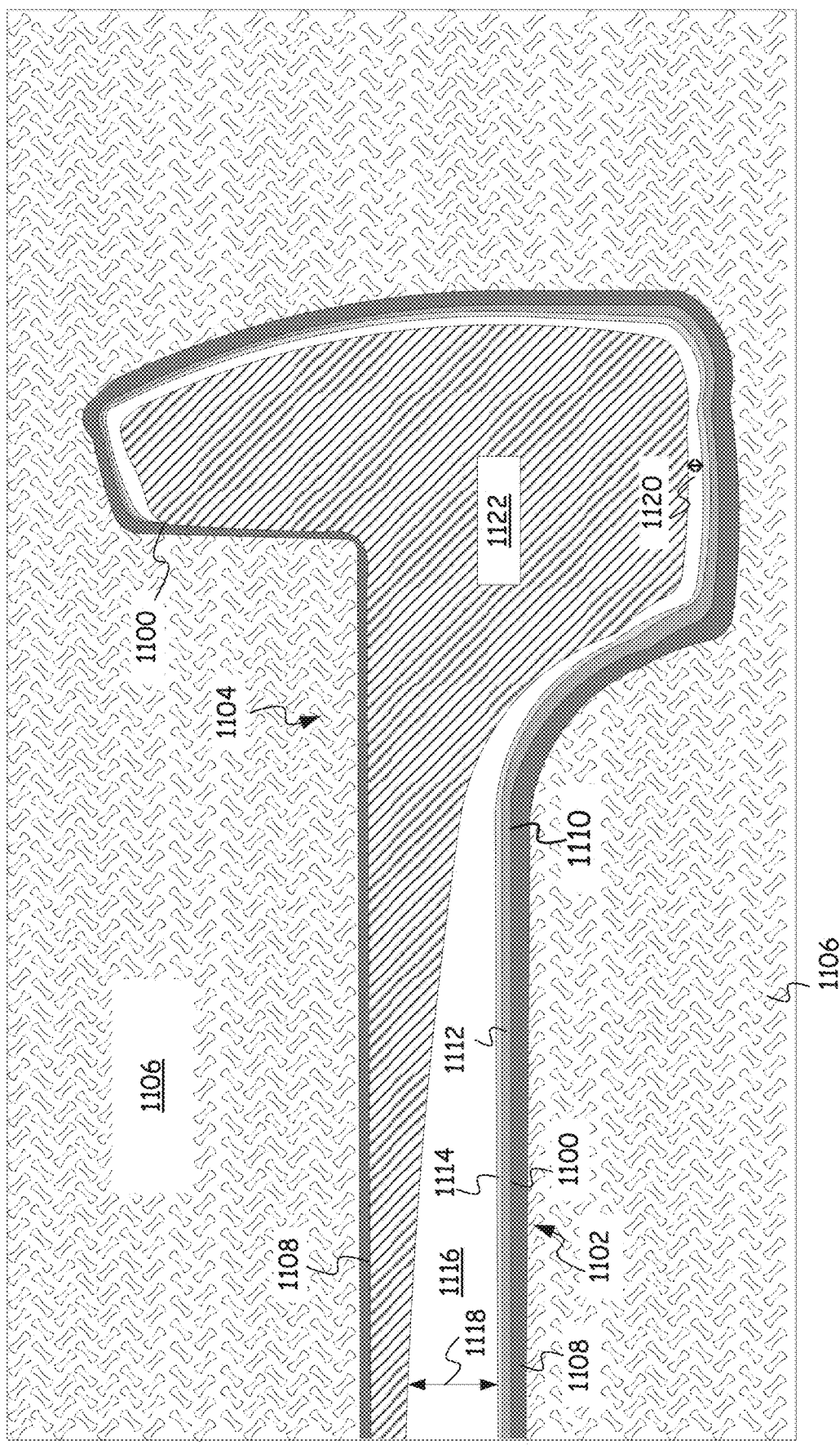
FIG. 21 provides a sectional view of a part constructed through the various embodiments showing a single part in the build space.

FIG. 21 provides an example of a top cross-sectional view of a part constructed using the single part construction process of FIG. 19. In FIG. 21, the part is defined by an STL boundary 1100 that is divided into two regions 1102 and 1104, each having respective features. For region 1102, three bands of material selection rules are defined outside of the part and four bands of material selection rules are defined inside the part. In particular, outside of the STL boundary there is a band 1106 constructed by a modulating function that modulates between producing two different materials resulting in a support area with structure. Band 1108 includes an aperiodic modulating function that provides a constant amount of a single support material. Band 1110 consists of an aperiodic modulating function that assigns an air gap to the voxels in the band. Within the STL boundary, band 1112 is represented by an aperiodic modulating function that provides a constant density coating material. Band 1114 is described by a modulating function that modulates between the coating of band 1112 and a cortical material found in a cortical band 1116. Cortical band 1116 has a varying thickness as indicated by wider thickness 1118 and narrower thickness 1120. Thus the size of cortical band 1116 varies based on what is the closest STL boundary point. Cortical band 1116 is described by an aperiodic modulating function that provides a constant intensity cortical material. Band 1122 is described by a noisy modulating function that modulates between the cortical material of band 1116 and a marrow material. The noisy function increases the amount of marrow material as the distance field increases.

Region 1104 contains bands 1106 and 1108 from the exterior of region 1102 but only includes interior band 1122 from region 1102.

Returning to FIG. 20, when the point features 9209 for the closest part points indicate that the material selection rules of two different parts are to be blended at step 1000, the process continues at step 1006. In step 1006, at least two of the parts in the build space are selected. The number of parts that are selected is based on designations stored in point features 9209 for all of the parts in the build space. Such features can include threshold distance fields that require the voxel to be within a certain distance of the STL boundary in order for the part's material selection rules to be used during blending. In other embodiments, certain point features 9209 will indicate that a part's material selection rules are only to be blended when a certain number of other parts are present in the build space.

At step 1008, material selection rules 9220 associated with the parts selected at step 1006 and identified in point features 9209 are retrieved. At step 1010, the respective distance field of the voxel and region designation, if any, of the voxel relative to each part selected at step 1006 are used to identify which material selection rules are to be selected for blending. At step 1012, one or both of materials and modulating functions of the selected material selection rules are blended or merged. In accordance with one embodiment, blending or merging modulating functions involves weighting the modulating functions using the distance fields and summing or multiplying the weighted modulating functions to form a merged function. The weighting is such that if a voxel is within two parts, the weight for a modulating function of one of the parts increases as the distance field value for that part increases. When the voxel is located outside of two parts, the opposite is true and the weighting for the modulating function relative to a part decreases as the magnitude of the distance field for the part increases. In other embodiments, the blending or merging is performed by using a random function and selecting which material to apply based on whether the output of the random function is above or below a threshold. The threshold is set as a function of the distance field for one of the parts, such that it becomes more likely that a material of a particular part will be selected for the voxel as the distance field for that part increases. This produces a merged area across the overlapping portions of the two parts where the material content of the voxels changes gradually across the merged area.

After the material/modulating functions have been blended at step 1012, the distance fields for one or more of the parts are applied to the blended functions at step 1014 along with the build space region for the voxel to produce a computed value that is then used to select the material for the voxel at step 1016.

Figure 22:
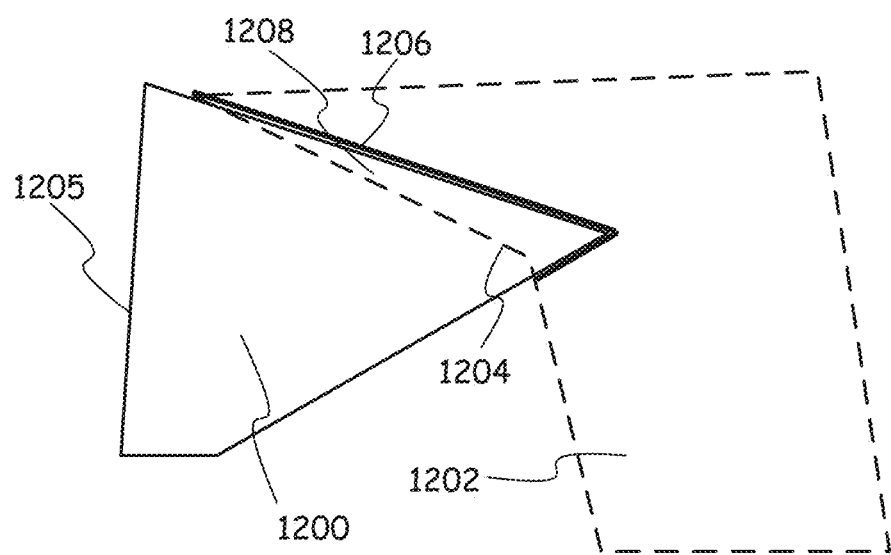
FIG. 22 provides a side view of two parts showing the removal of interference through the selection of a single part's material selection rules.

FIG. 22 provides an example of multiple part material selection in which selecting a single part at step 1002 removes interference between parts. At times, meshes 9202 for different parts will be described such that the parts overlap when the designer intended the parts to be separate. Such interference can be time consuming to remove. Under step 1002, such interference is automatically eliminated by selecting only one of the parts when a voxel is described by meshes 9202 as being in two different part.

In the example of FIG. 22, there are two parts 1200 and 1202. Dotted lines 1204 indicate the STL boundary for part 1202 as described by meshes 202 and solid line 1205 indicates the STL boundary for pat 1200. As shown in FIG. 22, STL boundary 1204 is within part 1200 and as such, the description of the STL boundaries shows an interference between parts 1200 and 1202. By selecting a single part at step 1002, in this case, part 1200, it is possible to remove the interference described in the meshes 202 to provide a new part boundary 1206 (shown in bold) for part 1202. Thus, in interference area 1208 where parts 1200 and 1202 overlap, the selection of part 1200 at step 1002 effectively shifts boundary 1204 to boundary 1206 for part 1202, thereby eliminating the interference between the two parts.

Figure 23:
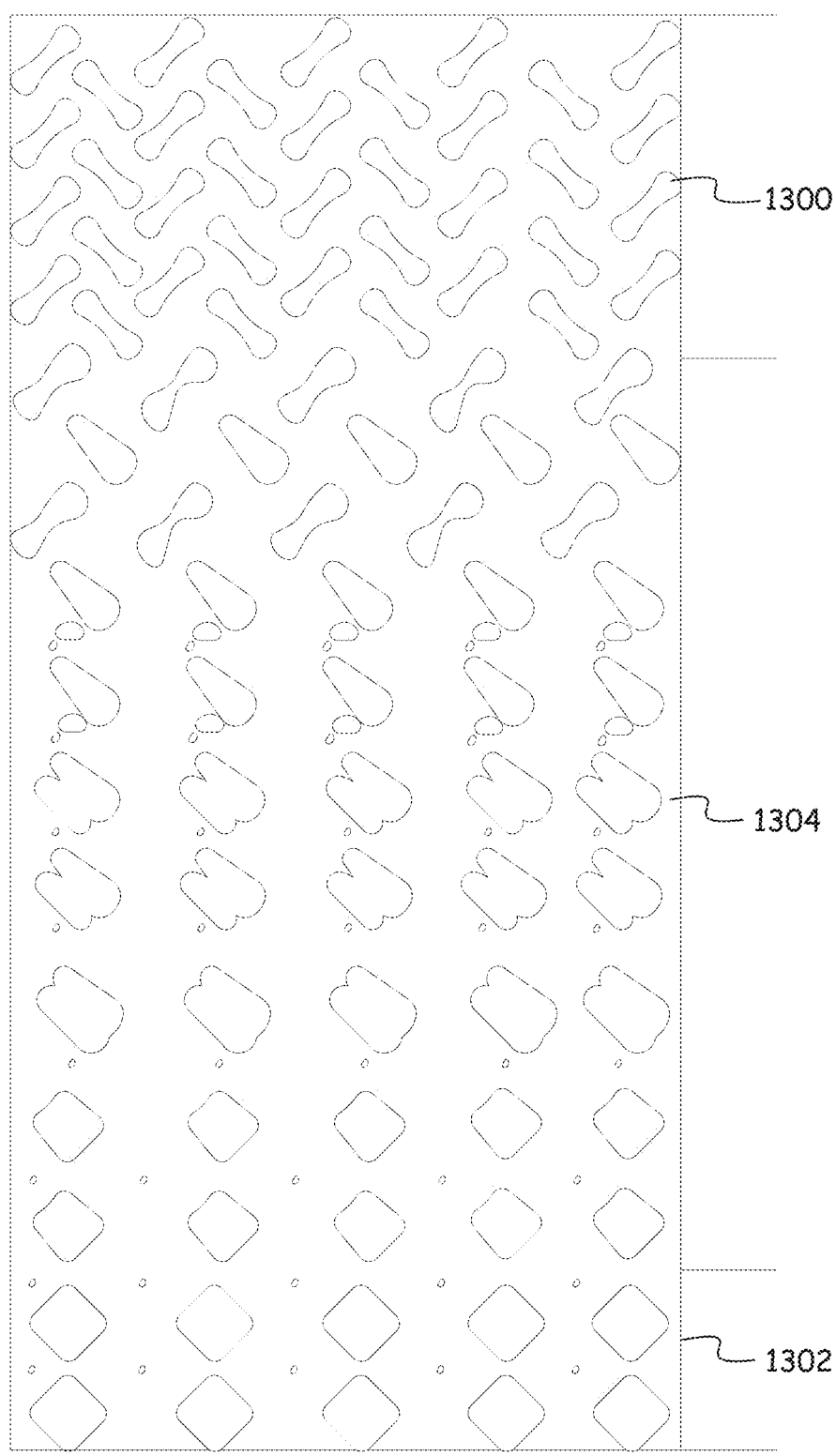
FIG. 23 shows a merged area where two different modulating functions are merged together.

FIG. 23 provides an example of blending two modulating functions using a distance field. In FIG. 23, a gyroid modulating field shown in section 1300 is blended with a Schwartz lattice as shown in section 1302 across a blending area 1304. In the blending of FIG. 23, the two modulating functions are weighted such that as the distance field from the STL boundary defining the gyroid increases, the gyroid modulating function is weighted less and the Schwartz lattice is weighted more. This produces a smooth transition from the gyroid lattice to the Schwartz lattice.

Figure 24:
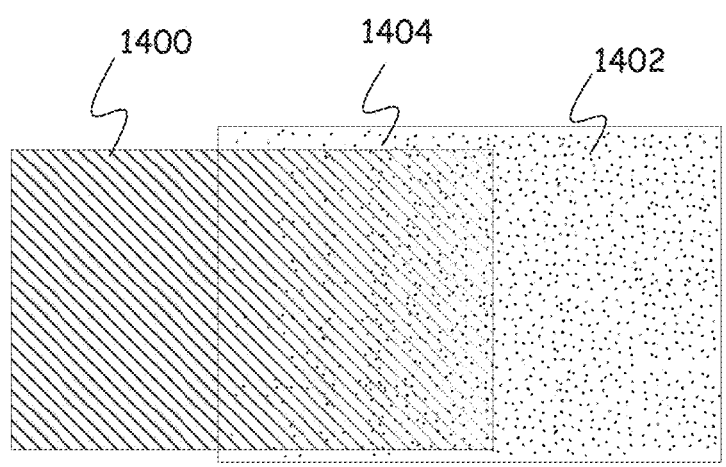
FIG. 24 shows a merged area where two different materials are merged together.

FIG. 24 shows the blending of parts material across an overlapped portion of two parts 1400 and 1402. In blended region 1404, the amount of material associated with part 1400 gradually decreases and the amount of material associated with part 1402 gradually increases along the extent from part 1400 to part 1402. Thus, as the magnitude of the distance field for part 1400 decreases, the amount of part material for part 1400 decreases in the blended region. Similarly, as the distance field for part 1402 decreases along the blended region 1404, the amount of material associated with part 1402 decreases in the blended region.

Returning to FIG. 11, after the material for a voxel has been determined at step 9118, the process determines if more voxels need to be processed at step 9120. If there are more voxels in the current slice, a new voxel is selected by returning to step 9112 and steps 9114, 9116, and 9118 are repeated for the new voxel. When all of the voxels for the current slice have been processed at step 9120, the material bitmap for the slice is complete and is output as material bitmap 9228. At step 9122, the process determines if there are more slices. If there are more slices, slice computations process 9210 moves up one slice at step 9124 and then returns to step 9106 to perform rendering operations in the +Z direction for the new slice. Steps 9108, 9110, 9112, 9114, 9116, 9118, and 9120 are then repeated for the new slice. Note that although the selection of materials for each voxel in a slice has been indicated as being performed before the +Z-buffer is loaded for each slice, and other embodiments, the rendering operation is performed in the +Z direction for each slice before determining materials for the voxels in any of the slices. After the +Z-buffers have been loaded for each slice, each slice is processed in turn by material selection unit 9226 to identify the material for each voxel in the slice.

After material bitmaps 9228 have been formed for each slice, a print conversion unit 9230 performs a print conversion step 9126 to form print instructions 9237. This print conversion step can be as simple as transferring material bitmaps 9228 as bitmaps 9232. In other embodiments, material bitmaps 9228 are converted into toolpaths 9234 that describe how a print head should be moved along a slice to deposit material. In one embodiment, a marching square algorithm is used to identify toolpaths 9234 from bitmaps 9228. In a further embodiment, the material bitmaps 9228 for each slice is converted into meshes 9236 that provide three-dimensional descriptions of part boundaries. Such meshes can be applied as input to other printers or as input to CAD systems. In one embodiment, a marching cubes algorithm is used to identify meshes 9236 from bitmaps 9228. After the material bitmaps 9228 have been converted into print instructions 9237, the print instructions are communicated through communication adapter 9092 so that the part can be manufactured at step 9128.

The embodiments above can thus load a CAD model onto a GPU, use the GPU to compute signed distance fields for every voxel, assign a material to each voxel based on the signed distance fields, and outputs images suitable for printing.

The various embodiments compute several different distance fields for each voxel in a slice, including the 3D Euclidean distance to the closest point of the CAD model, the 2D distance to the closest point on the cross section of the model in the slice, and the 2D distance to the silhouette of the model.

Each distance field may include feature transform information for the voxel, where the feature is the source point on the model used to record the distance reported for that voxel in the distance field. Feature transforms may include identifiers of the body or mesh, surface texture coordinates, surface normal, and position of the source point.

In accordance with one embodiment, the material assignment to each voxel becomes a function of the distance information and user-controlled parameters.

The distance metric may be Euclidean norm or a different norm, such as a $L^p$ or a chamfer norm.

The computations on the GPU use the Z-buffer to produce the depth component of distance in planar projections.

The computations on the GPU use a distance transform to compute 3D distance, 2D sectional distance, or distance from self-supporting regions.

The distance fields can be used to modulate carrier functions, such as implicit lattices and noise functions, to produce structures with varying compliance and porosity.

The distance fields can be used to perform offsetting and boolean operations.

The distance fields can be used to smoothly interpolate from one CAD model to another.

The distance fields can be used to adjust interferences and gaps between parts.

The distance fields can be used to create variable thickness offsets.

The distance fields can be combined with surface and volumetric textures to create layered and rippled textures.

The distance fields can be combined with voxel data, such as CAT scan and MRI data to produce models with volumetrically varying material properties.

The results can be saved as bitmap images for use for printers that use images.

The results can be traced into vector contours for 3D printers that use toolpaths.

The results can be reconstructed into 3D solid models.

The computations on the GPU use convolution or sampling to compute 2D sectional distance, silhouette distance, and the planar components of 3D distance. In accordance with one embodiment, these computations are performed iteratively to recursively compute distances efficiently.

The distance information can be used to modulate explicit and implicit functions, such as those describing lattices, to produce structures with varying bulk material properties such as compliance and porosity. The functions may describe shapes, voids in shapes, textures, varying material properties, and beam-like, honeycomb, and mixed topology lattices.

In the embodiments described below, there are CPU and GPU components. The CPU component:
1. Reads mesh data, textures, and slicing parameter data.
2. Sends the mesh data and related information to the GPU.
3. Provides a user interface to view and interact with the slice data.
4. Saves images created on the GPU to disk.

The GPU component:
1. Produces depth information about the model using the Z-buffer.
2. Combines the depth information into structures with different distance information.
3. Calculates the composition of each voxel using the distance information.

4. Includes libraries for calculating lattices, performing solid modeling operations, calibrating color, etc.

In one embodiment, the various embodiments are implemented using Javascript, Node.js and Electron for the CPU and OpenGL ES for the GPU code. Other embodiments are implemented using C # on .NET or Mono and OpenGL 3.3.

Additional Applications:
1. Recording texture, normal, and other geometric information (collectively, "Surface Information") along with distance information while computing the distance field.
2. Using Surface Information and a bitmap to choose a color to assign to the model.
3. Using Surface Information and a bitmap to choose a material among several possible materials, possibly using dithering.
4. Using Surface Information and a bitmap to offset the model to create a physical displacement map.
5. Using Surface Information and a bitmap to change the glossiness of the printed result.
6. Using Surface Information and a bitmap to change the surface finish of the printed result.
7. Using Surface Information and a bitmap to change the hardness of the material closest to the value of the texture on the surface.
8. Using Surface Information and a bitmap to change the transparency of the material closest to the value of the texture on the surface.
9. Using Surface Information and a bitmap to change the mechanical properties, such as stiffness, of the material closest to the value of the texture on the surface.
10. Using Surface Information and a bitmap to alter the presence of support material on the surface of a part.
11. Using Surface Information and a bitmap to modulate implicit functions used in the volume of the part or in support structures surrounding it.
12. Using Surface Information and several bitmaps to produce several displacement maps that can be combined via Boolean operations to create surface textures that include overhang.
13. Using Surface Information and several bitmaps with transparent material to produce lenticular (animated or 3D) surface effects.
14. Using any combination of 2-9 together.
15. The use of 3D volumetric textures with distance field information to change material location composition, possibly in combination with 2-9.

In FIG. 9, computer 9066 was shown as a host for a single stand-alone additive manufacturing system. Alternatively, computer 9066 may function as a local server for multiple additive manufacturing systems 9068. For example, systems 9068 may be part of an overall production system to manufacture consumer or industrial OEM products. As such, computer 9066 and may perform the steps of FIG. 11 and may also perform one or more additional processing steps, such as run-time estimates, printer queuing, post-processing queuing, and the like. As shown, computer 9066 may optionally include one or more servers 9072 and one or more dedicated host computers 9074 associated with each system 9068, where server 9072 may communicate with host computers 9074 over one or more communication lines 9076 (e.g., network lines).

In yet another embodiment, computer 9066 and systems 9068 may be part of an on-demand service center. In this embodiment, computer 9066 may function as a cloud-based server, for example, where customers may submit digital models (e.g., STL data files) from their personal computers 9078 over the Internet via one or more network or communication lines 9080 to computer 9066 (e.g., to server 9072).

In this application, computer 9066 may perform the steps of FIG. 11 as well as one or more additional processing steps, such as support material volume calculations, price quoting, run-time estimates, printer queuing, post-processing queuing, shipping estimates, and the like. For example, in some embodiments, computer 9066 may generate support material volume calculations, build times, and price quoting as discussed in Nehme et al., U.S. Pat. No. 8,818,544. The service center may also include one or more post-printing stations (e.g., support removal stations, surface finishing stations, shipping stations, and the like, not shown), where computer 9066 may also optionally communicate with the post-printing station(s).

According to some embodiments of the invention there is provided a method comprising: selecting a voxel in a three-dimensional build space; for the selected voxel, determining a distance field value relative to a three-dimensional part in the three-dimensional build space; using the distance field value to select at least one material selection rule; applying a feature of the voxel to the at least one material selection rule to identify a material designation for the voxel, wherein the material designation indicates no material is to be placed at the voxel when the material selection rule identifies no material for the voxel and wherein the material designation indicates at least one material is to be placed at the voxel when the at least one material selection rule identifies the at least one material for the voxel; and outputting the material designation for the voxel for use in building the three-dimensional part using an additive manufacturing system.

According to some embodiments of the invention the method uses the shortest distance to determine the distance field value.

According to some embodiments of the invention the distance field value is in a first range of values if the voxel is outside of the part, is in a second range of values if the voxel is within the part and is a singular value if the voxel is on the boundary of the part.

According to some embodiments of the invention the voxel forms part of a lattice structure.

According to some embodiments of the invention the using the first distance field value and the second distance field value to set a material designation comprises using the first distance field value to identify a first function, using the second distance field value to identify a second function, merging the first function with the second function to form a merged function, and using the merged function to set the material designation.

According to some embodiments of the invention the first function describes a first lattice pattern, the second function describes a second lattice pattern and the merged function describes a transition lattice that transitions from the first lattice pattern to the second lattice pattern over a merge area.

According to some embodiments of the invention the using the first distance field value and the second distance field value to set a material designation comprises using the first distance field value to determine that the voxel is inside the first three-dimensional part, using the second distance field value to determine that the voxel is inside the second three-dimensional part and setting the material designation for the voxel to a material set for the first three-dimensional part instead of a second material set for the second three-dimensional part.

According to some embodiments of the invention the setting the material designation for the voxel to the material set for the first three-dimensional part instead of the second material set for the second three-dimensional part comprises identifying a closest portion of the first three-dimensional part to the voxel, retrieving a feature associated with the closest portion, and using the feature to decide to set the material designation for the voxel to the material set for the first three-dimensional part.

Example 6

Elastomeric Curable Formulations

Herein throughout, the phrase "elastomeric curable formulation" is also referred to herein as "elastomeric modeling material formulation", "elastomeric modeling formulation" or simply as "elastomeric formulation", and describes a formulation which, when hardened, features properties of a rubber or rubbery-like materials, also referred to herein and in the art as elastomers.

Elastomers, or rubbers, are flexible materials that are characterized by low Tg (e.g., lower than room temperature, preferably lower than 10° C., lower than 0° C. and even lower than −10° C.).

Exemplary such formulations are those marketed as Tango™, Tango+™ and Agilus™ families (e.g., Agilus™30).

Exemplary such formulations are described in WO2017/208238, which is incorporated by reference as if fully set forth herein.

Whenever "Agilus" or "Agilus formulation" (e.g., Agilus™30) is indicated, it is meant a formulation of the Agilus™ family (e.g., a formulation as described in WO2017/208238).

According to some of any of the embodiments described herein, the elastomeric curable modeling formulation comprises at least one elastomeric curable material.

The phrase "elastomeric curable material" describes a curable material, as defined herein, which, upon exposure to curing energy, provides a cured material featuring properties of an elastomer (a rubber, or rubber-like material).

Elastomeric curable materials typically comprise one or more polymerizable (curable) groups, which undergo polymerization upon exposure to a suitable curing condition (e.g., curing energy), linked to a moiety that confers elasticity to the polymerized and/or cross-linked material. Such moieties typically comprise alkyl, alkylene chains, hydrocarbon, alkylene glycol groups or chains (e.g., oligo or poly(alkylene glycol) as defined herein, urethane, oligourethane or polyurethane moieties, as defined herein, and the like, including any combination of the foregoing, and are also referred to herein as "elastomeric moieties".

An elastomeric curable material can be a mono-functional or multi-functional material, or a combination thereof.

An elastomeric mono-functional curable material according to some embodiments of the present invention can be a vinyl-containing compound represented by Formula I:

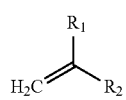

Formula I wherein at least one of $R_1$ and $R_2$ in Formula I is and/or comprises an elastomeric moiety, as described herein.

The (=CH$_2$) group in Formula I represents a polymerizable group, and is, according to some embodiments, a UV-curable group, such that the elastomeric curable material is a UV-curable material.

For example, $R_1$ in Formula I is or comprises an elastomeric moiety as defined herein and $R_2$ is, for example, hydrogen, C(1-4) alkyl, C(1-4) alkoxy, or any other substituent, as long as it does not interfere with the elastomeric properties of the cured material.

In some embodiments, $R_1$ in Formula I is a carboxylate as described herein, $R_2$ is hydrogen, and the compound is a mono-functional acrylate monomer. In some embodiments, $R_1$ in Formula I is a carboxylate as described herein, and $R_2$ is methyl, and the compound is mono-functional methacrylate monomer. Curable materials in which $R_1$ is carboxylate and $R_2$ is hydrogen or methyl are collectively referred to herein as "(meth)acrylates".

In some of any of these embodiments, the carboxylate group is represented by —C(=O)—ORc, and Rc is an elastomeric moiety as described herein.

In some embodiments, $R_1$ in Formula I is amide as described herein, $R_2$ is hydrogen, and the compound is a mono-functional acrylamide monomer. In some embodiments, $R_1$ in Formula I is amide as described herein, $R_2$ is methyl, and the compound is mono-functional methacrylamide monomer. Curable materials in which $R_1$ is amide and $R_2$ is hydrogen or methyl are collectively referred to herein as "(meth)acrylamide".

(Meth)acrylates and (meth)acrylamides are collectively referred to herein as (meth)acrylic materials.

In some embodiments, the amide is presented by —C(=O)—NRdRe, and Rd and Re are selected from hydrogen and an elastomeric moiety, at least one being an elastomeric moiety, as defined herein. When one or both of $R_1$ and $R_2$ in Formula I comprise a polymeric or oligomeric moiety, the mono-functional curable compound of Formula I is an exemplary polymeric or oligomeric mono-functional curable material. Otherwise, it is an exemplary monomeric mono-functional curable material.

In multi-functional elastomeric materials, the two or more polymerizable groups are linked to one another via an elastomeric moiety, as described herein.

In some embodiments, a multifunctional elastomeric material can be represented by Formula I as described herein, in which $R_1$ comprises an elastomeric material that terminates by a polymerizable group, as described herein.

For example, a di-functional elastomeric curable material can be represented by Formula I*:

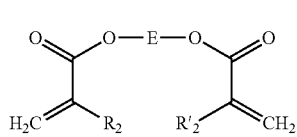

Formula I* wherein E is an elastomeric linking moiety as described herein, and R'$_2$ is as defined herein for $R_2$ in Formula I.

In another example, a tri-functional elastomeric curable material can be represented by Formula II:

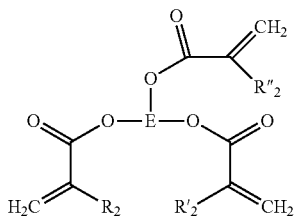

Formula II wherein E is an elastomeric linking moiety as described herein, and $R'_2$ and $R''_2$ are each independently as defined herein for $R_2$ in Formula I.

In some embodiments, a multi-functional (e.g., di-functional, tri-functional or higher) elastomeric curable material can be collectively represented by Formula III:

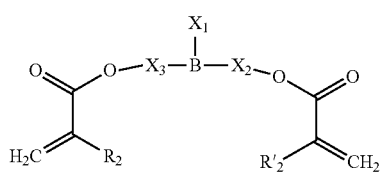

Formula III

Wherein:

$R_2$ and $R'_2$ are as defined herein;

B is a di-functional or tri-functional branching unit as defined herein (depending on the nature of $X_1$);

$X_2$ and $X_3$ are each independently absent, an elastomeric moiety as described herein, or is selected from an alkyl, a hydrocarbon, an alkylene chain, a cycloalkyl, an aryl, an alkylene glycol, a urethane moiety, and any combination thereof; and $X_1$ is absent or is selected from an alkyl, a hydrocarbon, an alkylene chain, a cycloalkyl, an aryl, an alkylene glycol, a urethane moiety, and an elastomeric moiety, each being optionally being substituted (e.g., terminated) by a meth(acrylate) moiety (O—C(═O) CR''$_2$═CH$_2$), and any combination thereof, or, alternatively, $X_1$ is:

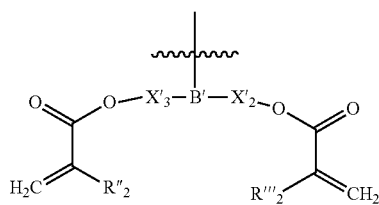

wherein:

the curved line represents the attachment point;

B' is a branching unit, being the same as, or different from, B;

$X'_2$ and $X'_3$ are each independently as defined herein for $X_2$ and $X_3$; and $R''_2$ and $R'''_2$ are as defined herein for $R_2$ and $R'_2$.

provided that at least one of $X_1$, $X_2$ and $X_3$ is or comprises an elastomeric moiety as described herein.

The term "branching unit" as used herein throughout describes a multi-radical, preferably aliphatic or alicyclic, linking moiety. By "multi-radical" it is meant that the linking moiety has two or more attachment points such that it links between two or more atoms and/or groups or moieties.

That is, the branching unit is a chemical moiety that, when attached to a single position, group or atom of a substance, creates two or more functional groups that are linked to this single position, group or atom, and thus "branches" a single functionality into two or more functionalities.

In some embodiments, the branching unit is derived from a chemical moiety that has two, three or more functional groups. In some embodiments, the branching unit is a branched alkyl or a branched linking moiety as described herein.

Multi-functional elastomeric curable materials featuring 4 or more polymerizable groups are also contemplated, and can feature structures similar to those presented in Formula III, while including, for example, a branching unit B with higher branching, or including an $X_1$ moiety featuring two (meth)acrylate moieties as defined herein, or similar to those presented in Formula II, while including, for example, another (meth)acrylate moiety that is attached to the elastomeric moiety.

In some embodiments, the elastomeric moiety, e.g., Rc in Formula I or the moiety denoted as E in Formulae I*, II and III, is or comprises an alkyl, which can be linear or branched, and which is preferably of 3 or more or of 4 or more carbon atoms; an alkylene chain, preferably of 3 or more or of 4 or more carbon atoms in length; an alkylene glycol as defined herein, an oligo(alkylene glycol), or a poly(alkylene glycol), as defined herein, preferably of 4 or more atoms in length, a urethane, an oligourethane, or a polyurethane, as defined herein, preferably of 4 or more carbon atoms in length, and any combination of the foregoing.

In some of any of the embodiments described herein, the elastomeric curable material is a (meth)acrylic curable material, as described herein, and in some embodiments, it is an acrylate.

In some of any of the embodiments described herein, the elastomeric curable material is or comprises a mono-functional elastomeric curable material, and is some embodiments, the mono-functional elastomeric curable material is represented by Formula I, wherein $R_1$ is —C(═O)—ORa and Ra is an alkylene chain (e.g., of 4 or more, preferably 6 or more, preferably 8 or more, carbon atoms in length), or a poly(alkylene glycol) chain, as defined herein.

In some embodiments, the elastomeric curable material is or comprises a multi-functional elastomeric curable material, and is some embodiments, the multi-functional elastomeric curable material is represented by Formula I*, wherein E is an alkylene chain (e.g., of 4 or more, or 6 or more, carbon atoms in length), and/or a poly(alkylene glycol) chain, as defined herein.

In some embodiments, the elastomeric curable material is or comprises a multi-functional elastomeric curable material, and is some embodiments, the multi-functional elastomeric curable material is represented by Formula II, wherein E is a branched alkyl (e.g., of 3 or more, or of 4 or more, or of 5 or more, carbon atoms in length).

In some of any of the embodiments described herein, the elastomeric curable material is an elastomeric acrylate or methacrylate (also referred to as acrylic or methacrylic elastomer), for example, of Formula I, I*, II or III, and in some embodiments, the acrylate or methacrylate is selected such that when hardened, the polymeric material features a Tg lower than 0° C. or lower than −10° C.

Exemplary elastomeric acrylate and methacrylate curable materials include, but are not limited to, 2-propenoic acid, 2-[[(butylamino)carbonyl]oxy]ethyl ester (an exemplary urethane acrylate), and compounds marketed under the trade names SR335 (Lauryl acrylate) and SR395 (isodecyl acrylate) (by Sartomer). Other examples include compounds marketed under the trade names SR350D (a trifunctional trimethylolpropane trimethacrylate (TMPTMA), SR256 (2-(2-ethoxyethoxy)ethyl acrylate, SR252 (polyethylene glycol (600) dimethacrylate), SR561 (an alkoxylated hexane diol diacrylate) (by Sartomer).

It is to be notes that other acrylic materials, featuring, for example, one or more acrylamide groups instead of one or more acrylate or methacrylate groups are also contemplated. In some of any of the embodiments described herein, the elastomeric curable material comprises one or more monofunctional elastomeric curable material(s) (e.g., a monofunctional elastomeric acrylate, as represented, for example, in Formula I) and one or more multi-functional (e.g., di-functional) elastomeric curable materials(s) (e.g., a di-functional elastomeric acrylate, as represented, for example, in Formula I*, II or III) and in any of the respective embodiments as described herein.

In some of any of the embodiments described herein, a total amount of the elastomeric curable material(s) is at least 40%, or at last 50%, or at least 60%, and can be up to 70% or even 80%, of the total weight of an elastomeric modeling material formulation as described herein.

In some of any of the embodiments described herein, the elastomeric curable modeling formulation further comprises silica particles.

In some of any of the embodiments described herein, the silica particles have an average particle size lower than 1 micron, namely, the silica particles are sub-micron particles. In some embodiments, the silica particles are nano-sized particles, or nanoparticles, having an average particle size in the range of from 0.1 nm to 900 nm, or from 0.1 nm to 700 nm, or from 1 nm to 700 nm, or from 1 nm to 500 nm or from 1 nm to 200 nm, including any intermediate value and subranges therebetween.

In some embodiments, at least a portion of such particles may aggregate, upon being introduced to the formulation. In some of these embodiments, the aggregate has an average size of no more than 3 microns, or no more than 1.5 micron.

Any commercially available formulations of sub-micron silica particles is usable in the context of the present embodiments, including fumed silica, colloidal silica, precipitated silica, layered silica (e.g., montmorillonite), and aerosol assisted self-assembly of silica particles.

The silica particles can be such that feature a hydrophobic or hydrophilic surface. The hydrophobic or hydrophilic nature of the particles' surface is determined by the nature of the surface groups on the particles.

When the silica is untreated, namely, is composed substantially of Si and O atoms, the particles typically feature silanol (Si—OH) surface groups and are therefore hydrophilic. Untreated (or uncoated) colloidal silica, fumed silica, precipitated silica and layered silica all feature a hydrophilic surface, and are considered hydrophilic silica.

Layered silica may be treated so as to feature long-chain hydrocarbons terminating by quaternary ammonium and/or ammonium as surface groups, and the nature of its surface is determined by the length of the hydrocarbon chains. Hydrophobic silica is a form of silica in which hydrophobic groups are bonded to the particles' surface, and is also referred to as treated silica or functionalized silica (silica reacted with hydrophobic groups).

Silica particles featuring hydrophobic surface groups such as, but not limited to, alkyls, preferably medium to high alkyls of 2 or more carbon atoms in length, preferably of 4 or more, or 6 or more, carbon atoms in length, cycloalkyls, aryl, and other hydrocarbons, as defined herein, or hydrophobic polymers (e.g., polydimethylsiloxane), are particles of hydrophobic silica.

Silica particles as described herein can therefore by untreated (non-functionalized) and as such are hydrophilic particles.

Alternatively, silica particles as described herein can be treated, or functionalized, by being reacted so as to form bonds with the moieties on their surface.

When the moieties are hydrophilic moieties, the functionalized silica particles are hydrophilic.

Silica particles featuring hydrophilic surface groups such as, but not limited to, hydroxy, amine, ammonium, carboxy, silanol, oxo, and the like, are particles of hydrophilic silica.

When the moieties are hydrophobic moieties, as described herein, the functionalized silica particles are hydrophobic.

In some of any of the embodiments described herein, at least a portion, or all, of the silica particles feature a hydrophilic surface (namely, are hydrophilic silica particles, for example, of untreated silica such as colloidal silica).

In some of any of the embodiments described herein, at least a portion, or all, of the silica particles feature a hydrophobic surface (namely, are hydrophobic silica particles).

In some embodiments, the hydrophobic silica particles are functionalized silica particles, namely, particles of silica treated with one or more hydrophobic moieties.

In some of any of the embodiments described herein, at least a portion, or all, of the silica particles are hydrophobic silica particles, functionalized by curable functional groups (particles featuring curable groups on their surface).

The curable functional groups can be any polymerizable group as described herein. In some embodiments, the curable functional groups are polymerizable by the same polymerization reaction as the curable monomers in the formulation, and/or when exposed to the same curing condition as the curable monomers. In some embodiments, the curable groups are (meth)acrylic (acrylic or methacrylic) groups, as defined herein.

Hydrophilic and hydrophobic, functionalized and untreated silica particles as described herein can be commercially available materials or can be prepared using methods well known in the art.

By "at least a portion", as used in the context of these embodiments, it is meant at least 10%, or at least 20%, or at least 30%, or at least 40%, or at least 50%, or at least 60%, or at least 70%, or at least 80%, or at least 90%, or at least 95%, or at least 98%, of the particles.

The silica particles may also be a mixture of two or more types of silica particles, for example, two or more types of any of the silica particles described herein.

In some of any of the embodiments described herein, an amount of the silica particles in a modeling material formulation comprising same ranges from about 1% to about 20%, or from about 1% to about 15%, or from about 1% to about 10%, by weight, of the total weight of the modeling material formulation.

In some of any of the embodiments described herein, an amount of the silica particles in a formulation system as described herein ranges from about 1% to about 20%, or from about 1% to about 15%, or from about 1% to about 10%, by weight, of the total weight of the formulation system.

In some embodiments, the formulation system comprises one formulation. In some embodiments, the formulation system comprises two or more formulations, and the silica particles are comprised within 1, 2 or all the formulations.

The amount of the silica particles can be manipulated as desired so as to control the mechanical properties of the cured modeling material and/or the object or part therein comprising same. For example, higher amount of silica particles may result in higher elastic modulus of the cured modeling material and/or the object or part thereof comprising same.

In some of any of the embodiments described herein, an amount of the silica particles is such that a weight ratio of the elastomeric curable material(s) and the silica particles in the one or more modeling material formulation(s) ranges from about 50:1 to about 4:1 or from about 30:1 to about 4:1 or from about 20:1 to about 2:1, including any intermediate values and subranges therebetween.

According to some of any of the embodiments described herein, the elastomeric modeling material formulation further comprises one or more additional curable material(s).

The additional curable material can be a mono-functional curable material, a multi-functional curable material, or a mixture thereof, and each material can be a monomer, an oligomer or a polymer, or a combination thereof.

Preferably, but not obligatory, the additional curable material is polymerizable when exposed to the same curing energy at which the curable elastomeric material is polymerizable, for example, upon exposure to irradiation (e.g., UV-vis irradiation).

In some embodiments, the additional curable material is such that when hardened, the polymerized material features Tg higher than that of an elastomeric material, for example, a Tg higher than 0° C., or higher than 5° C. or higher than 10° C.

In some embodiments, the additional curable material is a non-elastomeric curable material, featuring, for example, when hardened, Tg and/or Elastic Modulus that are different from those representing elastomeric materials.

In some embodiments, the additional curable material is a mono-functional acrylate or methacrylate ((meth)acrylate). Non-limiting examples include isobornyl acrylate (IBOA), isobornylmethacrylate, acryloyl morpholine (ACMO), phenoxyethyl acrylate, marketed by Sartomer Company (USA) under the trade name SR-339, urethane acrylate oligomer such as marketed under the name CN 131B, and any other acrylates and methacrylates usable in AM methodologies.

In some embodiments, the additional curable material is a multi-functional acrylate or methacrylate ((meth)acrylate). Non-limiting examples of multi-functional (meth)acrylates include propoxylated (2) neopentyl glycol diacrylate, marketed by Sartomer Company (USA) under the trade name SR-9003, Ditrimethylolpropane Tetra-acrylate (DiTMPTTA), Pentaerythitol Tetra-acrylate (TETTA), and Dipentaerythitol Penta-acrylate (DiPEP), and an aliphatic urethane diacrylate, for example, such as marketed as Ebecryl 230. Non-limiting examples of multi-functional (meth)acrylate oligomers include ethoxylated or methoxylated polyethylene glycol diacrylate or dimethacrylate, ethoxylated bisphenol A diacrylate, polyethylene glycol-polyethylene glycol urethane diacrylate, a partially acrylated polyol oligomer, polyester-based urethane diacrylates such as marketed as CNN91.

Any other curable materials, preferably curable materials featuring a Tg as defined herein, are contemplated as an additional curable material.

In some of any of the embodiments described herein, the elastomeric modeling material formulation further comprises an initiator, for initiating polymerization of the curable materials.

When all curable materials (elastomeric and additional, if present) are photopolymerizable, a photoinitiator is usable in these embodiments.

When all curable materials (elastomeric and additional, if present) are acrylic compounds or otherwise are photopolymerizable by free radical polymerization, a free radical photoinitiator, as described herein, is usable in these embodiments.

A concentration of a photoinitiator in a curable elastomeric formulation containing same may range from about 0.1 to about 5 weight percents, or from about 1 to about 5 weight percents, including any intermediate value and subranges therebetween.

According to some of any of the embodiments described herein, the elastomeric modeling material formulation further comprises one or more additional, non-curable material(s), for example, one or more of a colorant, a dispersant, a surfactant, a stabilizer and an inhibitor, as described herein for a soft modeling material formulation.

In some of any of the embodiments described herein, the elastomeric curable material is a UV curable material, and in some embodiments, it is an elastomeric (meth)acrylate, for example, an elastomeric acrylate.

In some of any of the embodiments described herein, an additional curable component is included in the elastomeric modeling material formulation, and in some embodiments, this component is a UV-curable acrylate or methacrylate.

In some of any of the embodiments described herein, the silica particles are (meth)acrylate-functionalized silica particles.

In some of any of the embodiments described herein, the elastomeric modeling material formulation comprises one or more mono-functional elastomeric acrylate, one or more multi-functional elastomeric acrylate, one or more mono-functional acrylate or methacrylate and one or more multi-functional acrylate or methacrylate.

In some of these embodiments, the elastomeric modeling material formulation further comprises one or more photoinitiators, for example, of the Irgacure® family.

In some of any of the embodiments described herein, all the curable materials and the silica particles the elastomeric modeling formulation are included in a single material formulation.

In some of any of the embodiments described herein, the elastomeric modeling formulation comprises two or more modeling material formulations and forms an elastomeric formulation system comprising an elastomeric curable formulation as described herein.

In some of these embodiments, one modeling material formulation (e.g., a first formulation, or Part A) comprises an elastomeric curable material (e.g., an elastomeric acrylate) and another modeling material formulation (e.g., a second formulation, or Part B) comprises an additional curable material.

Alternatively, each of the two modeling material formulations comprises an elastomeric curable material and one of the formulations further comprises an additional curable material.

Further alternatively, each of the two modeling material formulations in the elastomeric formulation system comprises an elastomeric curable material, yet, the elastomeric materials are different in each formulation. For example, one formulation comprises a mono-functional elastomeric curable material and another formulation comprises a multi-functional elastomeric material. Alternatively, one formulation comprises a mixture of mono-functional and multi-functional elastomeric curable materials at a ratio W and another formulation comprises a mixture of mono-functional and multi-functional elastomeric curable materials at a ratio Q, wherein W and Q are different.

Whenever each of the modeling material formulations comprises an elastomeric material as described herein, one or more of the modeling material formulations in the elastomeric formulation system can further comprise an additional curable material. In exemplary embodiments, one of the formulations comprises a mono-functional additional material and another comprises a multi-functional additional material. In further exemplary embodiments, one of the formulations comprises an oligomeric curable material and another formulation comprises a monomeric curable material.

Any combination of elastomeric and additional curable materials as described herein is contemplated for inclusion in the two or more modeling material formulations forming the elastomeric formulation system. Selecting the composition of the modeling material formulations and the printing mode allows fabrication of objects featuring a variety of properties in a controllable manner, as is described in further detail hereinbelow.

In some embodiments, the one or more modeling material formulations in an elastomeric formulation system are selected such that a ratio of an elastomeric curable material and an additional curable material provides a rubbery-like material as described herein.

In some embodiments, silica particles, one or more photoinitiators, and optionally other components, are included in one or both modeling material formulations.

In exemplary modeling material formulations according to some of any of the embodiments described herein, all curable materials are (meth)acrylates.

In any of the exemplary modeling material formulations described herein, a concentration of a photoinitiator ranges from about 1% to about 5% by weight, or from about 2% to about 5%, or from about 3% to about 5%, or from about 3% to about 4% (e.g., 3, 3.1, 3.2, 3.25, 3.3, 3.4, 3.5, 3.6, 3.7, 3.8, 3.85, 3.9, including any intermediate value therebetween) %, by weight, of the total weight of the formulation or formulation system comprising same.

In any of the exemplary modeling material formulations described herein, a concentration of an inhibitor ranges from 0 to about 2% weight, or from 0 to about 1%, and is, for example, 0, 0.1, 0.2, 0.3, 0.4, 0.5, 0.6, 0.7, 0.8, 0.9 or about 1%, by weight, including any intermediate value therebetween, of the total weight of the formulation or a formulation system comprising same.

In any of the exemplary modeling material formulations described herein, a concentration of a surfactant ranges from 0 to about 1% weight, and is, for example, 0, 0.01, 0.05, 0.1, 0.5 or about 1%, by weight, including any intermediate value therebetween, of the total weight of the formulation or formulation system comprising same.

In any of the exemplary modeling material formulations described herein, a concentration of a dispersant ranges from 0 to about 2% weight, and is, for example, 0, 0.1, 0.5, 0.7, 1, 1.2, 1.3, 1.35, 1.4, 1.5, 1.7, 1.8 or about 2%, by weight, including any intermediate value therebetween, of the total weight of the formulation or formulation system comprising same.

In exemplary modeling material formulations according to some of any of the embodiments described herein, a total concentration of an elastomeric curable material ranges from about 30% to about 90% by weight, or from about 40% to about 90%, by weight, or from about 40% to about 85%, by weight.

By "total concentration" it is meant herein throughout a total weight in all of the (one or more) elastomeric modeling material formulations, or in an elastomeric formulation system as described herein.

In some embodiments, the elastomeric curable material comprises a mono-functional elastomeric curable material and a multi-functional elastomeric curable material.

In some embodiments, a total concentration of the mono-functional elastomeric curable material ranges from about 20% to about 70%, or from about 30% to about 50%, by weight, including any intermediate value and subranges therebetween. In exemplary embodiments, a total concentration of the mono-functional elastomeric curable material ranges from about 50% to about 70%, or from about 55% to about 65%, or from about 55% to about 60% (e.g. 58%), by weight, including any intermediate value and subranges therebetween. In exemplary embodiments, a total concentration of the mono-functional elastomeric curable material ranges from about 30% to about 50%, or from about 35% to about 50%, or from about 40% to about 45% (e.g., 42%), by weight, including any intermediate value and subranges therebetween.

In some embodiments, a total concentration of the multi-functional elastomeric curable material ranges from about 10% to about 30%, by weight. In exemplary embodiments, a concentration of the mono-functional elastomeric curable material ranges from about 10% to about 20%, or from about 10% to about 15% (e.g. 12%), by weight. In exemplary embodiments, a concentration of the mono-functional elastomeric curable material ranges from about 10% to about 30%, or from about 10% to about 20%, or from about 15% to about 20% (e.g., 16%), by weight.

In exemplary modeling material formulations according to some of any of the embodiments described herein, a total concentration of an additional curable material ranges from about 10% to about 40% by weight, or from about 15% to about 35%, by weight, including any intermediate value and subranges therebetween.

In some embodiments, the additional curable material comprises a mono-functional curable material.

In some embodiments, a total concentration of the mono-functional additional curable material ranges from about 15% to about 25%, or from about 20% to about 25% (e.g., 21%), by weight, including any intermediate value and subranges therebetween. In exemplary embodiments, a concentration of the mono-functional elastomeric curable material ranges from about 20% to about 30%, or from about 25% to about 30% (e.g., 28%), by weight, including any intermediate value and subranges therebetween.

In exemplary elastomeric modeling material formulations or formulation systems comprising same according to some of any of the embodiments described herein, the elastomeric curable material comprises a mono-functional elastomeric curable material and a multi-functional elastomeric curable material; a total concentration of the mono-functional elastomeric curable material ranges from about 30% to about 50% (e.g., from about 40% to about 45%) or from about 50% to about 70% (e.g., from about 55% to about 60%) by weight; and a total concentration of the multi-functional elastomeric curable material ranges from about 10% to about 20% by weight; and the one or more formulation(s)

further comprise(s) an additional mono-functional curable material at a total concentration that ranges from about 20% to about 30%, by weight.

According to some of any of the embodiments described herein, the one or more modeling formulation(s) comprise(s) at least one elastomeric mono-functional curable material, at least one elastomeric multi-functional curable material and at least additional mono-functional curable material.

According to some of any of the embodiments described herein, a total concentration of the curable mono-functional material ranges from 10% to 30%, by weight of the total weight of the one or more modeling formulation(s).

According to some of any of the embodiments described herein, a total concentration of the elastomeric mono-functional curable material ranges from 50% to 70%, by weight, of the total weight of the one or more modeling formulation(s).

According to some of any of the embodiments described herein, a total concentration of the elastomeric multi-functional curable material ranges from 10% to 20%, by weight, of the total weight of the one or more modeling formulation(s).

According to some of any of the embodiments described herein, a total concentration of the curable mono-functional material ranges from 10% to 30%, by weight; a total concentration of the elastomeric mono-functional curable material ranges from 50% to 70%, by weight; and a total concentration of the elastomeric multi-functional curable material ranges from 10% to 20%, by weight, of the total weight of the one or more modeling formulation(s).

According to some of any of the embodiments described herein, a total concentration of the curable mono-functional material ranges from 20% to 30%, by weight, of the total weight of the one or more modeling formulation(s).

According to some of any of the embodiments described herein, a total concentration of the elastomeric mono-functional curable material ranges from 30% to 50%, by weight, of the total weight of the one or more modeling formulation(s).

According to some of any of the embodiments described herein, a total concentration of the elastomeric multi-functional curable material ranges from 10% to 30%, by weight, of the total weight of the one or more modeling formulation(s).

According to some of any of the embodiments described herein, a total concentration of the curable mono-functional material ranges from 20% to 30%, by weight; a total concentration of the elastomeric mono-functional curable material ranges from 30% to 50%, by weight; and a total concentration of the elastomeric multi-functional curable material ranges from 10% to 30%, by weight, of the total weight of the one or more modeling formulation.

In the exemplary modeling material formulations described herein, a concentration of each component is provided as its concentration when one modeling material formulations is used or as its total concentration in two or more modeling material formulations.

In some embodiments, an elastomeric modeling material formulation (or the two or more modeling material formulations) as described herein, is characterized, when hardened, by Tear Resistance of at least 4,000 N/m, or at least 4500 N/m or at least 5,000 N/m, whereby the Tear Resistance is determined according to ASTM D 624.

In some embodiments, an elastomeric modeling material formulation (or the two or more modeling material formulations) as described herein, is characterized, when hardened, by Tear Resistance higher by at least 500 N/m, or by at least 700 N/m, or by at least 800 N/m, than that of the same modeling material formulation(s) devoid of said silica particles, when hardened.

In some embodiments, an elastomeric modeling material formulation (or the two or more modeling material formulations) as described herein, is characterized, when hardened, by Tensile Strength of at least 2 MPa.

In some embodiments, an elastomeric modeling material formulation (or the two or more modeling material formulations) as described herein, is such that an object consisting of the cured modeling material and featuring two O-rings and a tube connecting the rings, is characterized by Tear Resistance under constant elongation of at least one hour, or at least one day.

According to some of any of the embodiments described herein, the elastomeric curable material is selected from a mono-functional elastomeric curable monomer, a mono-functional elastomeric curable oligomer, a multi-functional elastomeric curable monomer, a multi-functional elastomeric curable oligomer, and any combination thereof, as described herein for an elastomeric curable material in any of the respective embodiments and any combination thereof.

In some embodiments, the elastomeric curable material comprises one or more materials selected from the materials represented by Formula I, I*, II and III, as described herein in any of the respective embodiments and any combination thereof.

According to some of any of the embodiments described herein, the elastomeric curable material and the silica particles are in the same formulation.

According to some of any of the embodiments described herein, the elastomeric curable formulation system further comprises at least one additional curable material.

According to some of any of the embodiments described herein, the additional curable material is selected from a mono-functional curable monomer, a mono-functional curable oligomer, a multi-functional curable monomer, a multi-functional curable oligomer and any combination thereof, as described herein for an additional curable material in any of the respective embodiments and any combination thereof.

According to some of any of the embodiments described herein, the elastomeric curable material, the silica particles and the additional curable material are in the same formulation.

According to some of any of the embodiments described herein, the elastomeric curable material is a UV-curable elastomeric material.

According to some of any of the embodiments described herein, the elastomeric curable material is an acrylic elastomer.

Example 7

Combination of Computer Object Data

FIGS. 28A-D are schematic illustrations of combination of computer object data, which can be used for fabricating an object with an additional structure. The illustrations are for the case in which the object 350 is a bone and the additional structure is bone tumor 356a, but one of ordinary skills in the art, provided with the details described herein, would know how to adjust the process for other types of objects and additional structure.

Figure 28A:
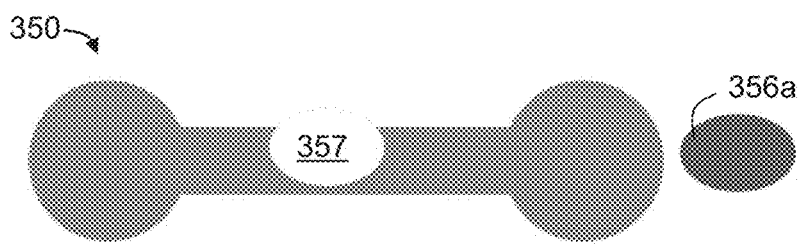
FIGS. 28A-28D are schematic illustrations of combination of computer object data, which can be used for fabricating an object with an additional structure.
Figure 28B:

FIGS. 28A and 28B illustrate the input computer object data. As shown in FIGS. 28A and 28B, two sets of input computer object data are provided separately for the object 350 (left) and the additional structure (right). FIG. 28A illustrates an embodiment in which the computer object data that correspond to object 350 describe the object with a void 357 that is shape-wise and size-wise compatible to the shape and size of structure 356a, and FIG. 28B illustrates an embodiment in which the computer object data that correspond to object 350 describe the object as a complete object, irrespective of the shape and size of the additional structure.

Figure 28C:
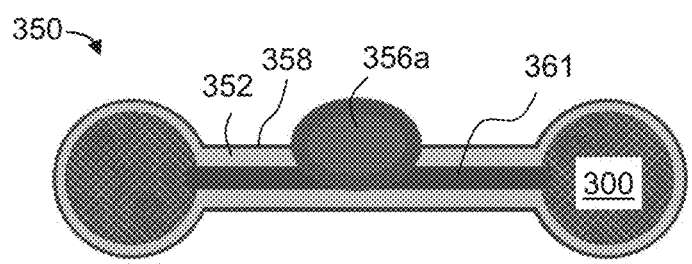
Figure 28D:
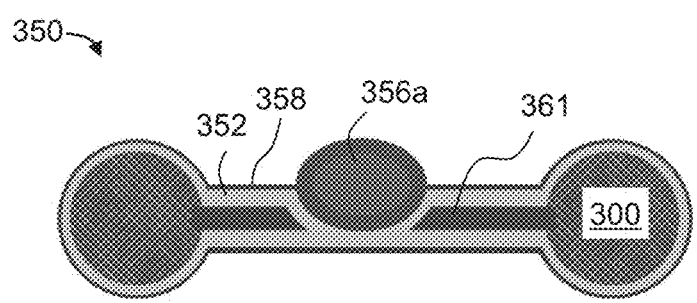

The two sets of data are registered and combined by the computer. The combined data according to some embodiments of the present invention is illustrated in FIG. 28C. As shown, the set of data corresponding to structure 356a override the set of data corresponding to object 350 at the location of structure 356a. The registration and combination of data can result in overlapping portions or portions having the same boundary (within certain range, e.g. about 0.2 mm). In the exemplified illustration, the registration and combination of data results in a removal of some features from object 350 (core 261, shell 352 and coating 358, in the present example) at the location occupied by structure 356a, but optionally and preferably not at other locations. FIG. 28D illustrates an undesired situation in which the combination results of removal of features (core 361 in the present example) also at locations adjacent to structure 356a.

The rules for such data override and feature removal can be predefined, for example, based on the shape, size, color, or type or material assignment. Alternatively, or additionally, the rules for such data override and feature removal can be according to instructions received from the operator, e.g., using the user interface or computer.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for additive manufacturing, comprising:
a three-dimensional fabrication apparatus having a plurality of dispensing heads configured to dispense building materials, and a hardening device configured to harden said building materials, once dispensed; and
a controller having a circuit configured to operate said apparatus to form a multi-layered textured region made of voxel elements containing different materials at interlaced locations, and a shell at least partially surrounding said textured region, wherein said circuit is configured to select said materials such that a hardness of said shell once hardened is higher than a hardness of said textured region once hardened; said voxel elements of said textured region being arranged to form a plurality of texture elements each comprising an interior portion surrounded by a wall portion, wherein said materials and said interlaced locations are selected by said controller such that said textured region exhibits, once hardened, a stress variation of at most ±20% over a strain range of from about 0.1% to about 0.3%.

2. The system of claim 1, wherein said circuit is configured to apply a modulating function for selecting said interlaced locations.

3. The system of claim 2, wherein said modulating function comprises a noise function.

4. The system of claim 3, wherein said modulating function comprises a simplex noise function.

5. The system of claim 3, wherein said modulating function comprises an open simplex noise function.

6. The system of claim 3, wherein said function comprises a Worley noise function.

7. The system of claim 3, wherein said function comprises a Perlin noise function.

8. The system of claim 3, wherein said function comprises a wavelet noise function.

9. The system of claim 2, wherein said modulating function comprises a periodic function.

10. The system of claim 9, wherein said modulating function has a period of 2 or less millimeters.

11. The system of claim 2, wherein said modulating function comprises an aperiodic function.

12. The system of claim 1, wherein said circuit is configured to select said materials such that a hardness of said wall portion once hardened is higher than a hardness of said interior portion, once hardened.

13. The system of claim 1, wherein said circuit is configured to control said apparatus to form a flexible annulus structure in said shell.

14. The system of claim 1, wherein said circuit is configured to control said apparatus to form on said shell a structure having a shape of a soft tissue element.

15. The system of claim 1, wherein said circuit is configured to control said apparatus to form a coating over said shell, and to select said materials such that once said textured region, said shell, and said coating are hardened, a hardness of said coating is higher than a hardness of said shell.

16. The system of claim 15, wherein said circuit is configured to control said apparatus to form on said coating a structure having a shape of a soft tissue element.

17. The system of claim 1, wherein said circuit is configured to control said apparatus to form a core surrounded by said textured region and/or said shell, and to select said materials such that once said textured region and said core are hardened, a hardness of said textured region is higher than a hardness of said core.

18. The system of claim 1, wherein said circuit is configured to control said apparatus to form a section having a shape of a bone tumor, and to select said materials such as to impart to said section mechanical properties that differ from mechanical properties of any voxel adjacent to said section outside said section.

* * * * *